(12) United States Patent
Becker et al.

(10) Patent No.: US 9,284,549 B2
(45) Date of Patent: *Mar. 15, 2016

(54) TAGGED OLIGONUCLEOTIDES AND THEIR USE IN NUCLEIC ACID AMPLIFICATION METHODS

(71) Applicant: Gen-Probe Incorporate, San Diego, CA (US)

(72) Inventors: Michael M. Becker, San Diego, CA (US); Kristin W. Livezey, Encinitas, CA (US); Wai-Chung Lam, Bonsall, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 14/051,104

(22) Filed: Oct. 10, 2013

(65) Prior Publication Data

US 2014/0066330 A1 Mar. 6, 2014

Related U.S. Application Data

(60) Continuation of application No. 13/612,601, filed on Sep. 12, 2012, now Pat. No. 8,580,510, which is a continuation of application No. 13/231,848, filed on Sep. 13, 2011, now Pat. No. 8,278,052, which is a
(Continued)

(51) Int. Cl.
| | |
|---|---|
| *C12P 19/34* | (2006.01) |
| *C12N 15/10* | (2006.01) |
| *C12Q 1/68* | (2006.01) |

(52) U.S. Cl.
CPC ............ *C12N 15/1065* (2013.01); *C12Q 1/689* (2013.01); *C12Q 1/6848* (2013.01); *C12Q 1/6895* (2013.01)

(58) Field of Classification Search
USPC ................................................ 435/6.12, 91.2
See application file for complete search history.

(56) References Cited

U.S. PATENT DOCUMENTS

| 4,683,195 A | 7/1987 | Mullis et al. |
| 5,104,792 A | 4/1992 | Silver et al. |

(Continued)

FOREIGN PATENT DOCUMENTS

| CN | 1427007 | 7/2003 |
| EP | 1201768 A2 | 10/2002 |

(Continued)

OTHER PUBLICATIONS

Voegel et al., "Nonstandard Hydrogen Bonding in Duplex Oligoncucleotides. The Base Pair between an Acceptor-Donor-Donor Pyrimiding Analog and a Donor-Acceptor-Acceptor Purine Analog," J. Am. Chem. Soc., 1994, 116:6929-6930, American Chemical Society, USA.

(Continued)

*Primary Examiner* — Kenneth Horlick
(74) *Attorney, Agent, or Firm* — Jeffrey E. Landes; Charles B. Cappellari

(57) ABSTRACT

The present invention provides nucleic acid amplification systems and methods that desirably reduce or eliminate false positive amplification signals resulting from contaminating biological material, e.g., nucleic acid, that may be present in one or more reagents used in an amplification reaction and/or that may be present in the environment in which an amplification reaction is performed. The invention offers the further advantage of requiring less stringent purification and/or sterility efforts than conventionally needed in order to ensure that enzymes and other reagents used in amplification reactions, and the environment in which an amplification reaction is performed, are free of bacterial or other nucleic acid contamination that may yield false positive results.

20 Claims, 18 Drawing Sheets

Related U.S. Application Data continuation of application No. 12/892,323, filed on Sep. 28, 2010, now Pat. No. 8,034,570, which is a division of application No. 11/810,834, filed on Jun. 6, 2007, now Pat. No. 7,833,716.

(60) Provisional application No. 60/871,442, filed on Dec. 21, 2006, provisional application No. 60/811,581, filed on Jun. 6, 2006.

(56) References Cited

U.S. PATENT DOCUMENTS

| | | |
|---|---|---|
| 5,215,899 A | 6/1993 | Dattagupta |
| 5,422,252 A | 6/1995 | Walker et al. |
| 5,442,252 A | 8/1995 | Golz |
| 5,474,916 A | 12/1995 | Reischl et al. |
| 5,487,985 A | 1/1996 | McClelland et al. |
| 5,561,044 A | 10/1996 | Walker et al. |
| 5,573,906 A | 11/1996 | Bannwarth et al. |
| 5,607,834 A | 3/1997 | Bagwell |
| 5,624,825 A | 4/1997 | Walker et al. |
| 5,643,762 A | 7/1997 | Ohshima et al. |
| 5,674,683 A | 10/1997 | Kool |
| 5,679,553 A | 10/1997 | Van Gemen et al. |
| 5,681,702 A | 10/1997 | Collins et al. |
| 5,733,733 A | 3/1998 | Auerback |
| 5,736,365 A | 4/1998 | Walker et al. |
| 5,763,186 A | 6/1998 | Ludtke et al. |
| 5,866,336 A | 2/1999 | Nazarenko et al. |
| 5,874,260 A | 2/1999 | Cleuziat et al. |
| 5,882,856 A | 3/1999 | Shuber |
| 5,928,869 A | 7/1999 | Nadeau et al. |
| 5,948,618 A | 9/1999 | Oka et al. |
| 5,958,700 A | 9/1999 | Nadeau et al. |
| 5,965,409 A | 10/1999 | Pardee et al. |
| 6,025,133 A | 2/2000 | Stull et al. |
| 6,033,851 A | 3/2000 | Yamane |
| 6,037,130 A | 3/2000 | Tyagi et al. |
| 6,051,377 A | 4/2000 | Mandecki |
| 6,060,245 A | 5/2000 | Sorge et al. |
| 6,090,552 A | 7/2000 | Nazarenko et al. |
| 6,194,155 B1 | 2/2001 | Cohen |
| 6,207,372 B1 | 3/2001 | Shuber |
| 6,207,379 B1 | 3/2001 | Lee et al. |
| 6,207,424 B1 | 3/2001 | Chou et al. |
| 6,218,119 B1 | 4/2001 | Kuiper et al. |
| 6,232,455 B1 | 5/2001 | Kroeger et al. |
| 6,235,889 B1 | 5/2001 | Ulanovsky |
| 6,251,610 B1 | 6/2001 | Gupte et al. |
| 6,251,639 B1 | 6/2001 | Kurn |
| 6,258,546 B1 | 7/2001 | McMillian et al. |
| 6,261,773 B1 | 7/2001 | Segawa et al. |
| 6,280,949 B1 | 8/2001 | Lizardi |
| 6,316,229 B1 | 11/2001 | Lizardi et al. |
| 6,361,945 B1 | 3/2002 | Becker et al. |
| 6,365,729 B1 | 4/2002 | Tyagi et al. |
| 6,379,932 B1 | 4/2002 | Arnold et al. |
| 6,383,752 B1 | 5/2002 | Agrawal et al. |
| 6,403,319 B1 | 6/2002 | Lizardi et al. |
| 6,514,706 B1 | 2/2003 | Von Kalle et al. |
| 6,518,026 B2 | 2/2003 | Harley et al. |
| 6,528,288 B2 | 3/2003 | Senapathy |
| 6,544,736 B1 | 4/2003 | Shimamoto et al. |
| 6,582,938 B1 | 6/2003 | Su et al. |
| 6,618,679 B2 | 9/2003 | Loehrlein et al. |
| 6,638,722 B2 | 10/2003 | Ji et al. |
| 6,660,229 B2 | 12/2003 | Cantor et al. |
| 6,677,121 B2 | 1/2004 | Lizardi et al. |
| 6,686,156 B2 | 2/2004 | Kurn |
| 6,737,253 B2 | 5/2004 | Tillett |
| 6,743,605 B1 | 6/2004 | Rabbani et al. |
| 6,750,014 B2 | 6/2004 | de Barr et al. |
| 6,787,310 B2 | 9/2004 | Chiesa et al. |
| 6,797,470 B2 | 9/2004 | Barany et al. |
| 6,808,888 B2 | 10/2004 | Zhang et al. |
| 6,812,005 B2 | 11/2004 | Fan et al. |
| 6,821,770 B1 | 11/2004 | Hogan |
| 6,828,098 B2 | 12/2004 | Langmore et al. |
| 6,844,155 B2 | 1/2005 | Shuber |
| 6,890,741 B2 | 5/2005 | Fan et al. |
| 6,919,189 B2 | 7/2005 | Bowdish et al. |
| 6,955,901 B2 | 10/2005 | Schouten |
| 6,964,847 B1 | 11/2005 | Englert |
| 7,057,025 B2 | 6/2006 | Livak et al. |
| 7,081,339 B2 | 7/2006 | Slepnev |
| 7,083,929 B2 | 8/2006 | Wong |
| 7,094,536 B2 | 8/2006 | Kurn |
| 7,122,317 B2 | 10/2006 | Clausen et al. |
| 7,129,044 B2 | 10/2006 | Namsaraev et al. |
| 7,138,254 B2 | 11/2006 | Jovanovich et al. |
| 7,141,372 B2 | 11/2006 | Spivack et al. |
| 7,141,650 B2 | 11/2006 | Oda et al. |
| 7,153,658 B2 | 12/2006 | Anderson et al. |
| 7,176,002 B2 | 2/2007 | Lao et al. |
| 7,208,278 B2 | 4/2007 | Chen et al. |
| 7,214,490 B2 | 5/2007 | Su et al. |
| 7,230,092 B2 | 6/2007 | Bortolin et al. |
| 7,297,485 B2 | 11/2007 | Bornarth et al. |
| 7,312,034 B2 | 12/2007 | Virgos et al. |
| 7,319,022 B1 | 1/2008 | Mahoney et al. |
| 7,323,306 B2 | 1/2008 | Dunn et al. |
| 7,348,164 B2 | 3/2008 | Andrus et al. |
| 7,351,557 B2 | 4/2008 | Kurn |
| 7,371,520 B2 | 5/2008 | Zhao et al. |
| 7,374,885 B2 | 5/2008 | Becker et al. |
| 7,432,055 B2 | 10/2008 | Pemov et al. |
| 7,482,119 B2 | 1/2009 | Parker et al. |
| 7,513,656 B2 | 4/2009 | Park et al. |
| 7,537,886 B1 | 5/2009 | Nazarenko et al. |
| RE41,365 E | 6/2010 | Bowdish et al. |
| 7,833,716 B2 | 11/2010 | Becker et al. |
| 2002/0025525 A1 | 2/2002 | Shuber |
| 2002/0031777 A1 | 3/2002 | Starr-Spires |
| 2002/0127569 A1 | 9/2002 | Weisburg et al. |
| 2003/0044780 A1 | 3/2003 | Lapidus et al. |
| 2003/0087251 A1 | 5/2003 | Kurn |
| 2003/0104421 A1 | 6/2003 | Colangelo et al. |
| 2003/0104436 A1 | 6/2003 | Morris et al. |
| 2003/0162199 A1 | 8/2003 | Bonner |
| 2003/0165859 A1 | 9/2003 | Nazarenko et al. |
| 2004/0014129 A1 | 1/2004 | Brown |
| 2004/0086892 A1 | 5/2004 | Crothers et al. |
| 2004/0259116 A1 | 12/2004 | Beckman et al. |
| 2005/0042666 A1 | 2/2005 | Nazarenko et al. |
| 2005/0208530 A1 | 9/2005 | Chesnut et al. |
| 2005/0260573 A1 | 11/2005 | Rabbani et al. |
| 2006/0019274 A1 | 1/2006 | Goel |
| 2006/0046265 A1 | 3/2006 | Becker et al. |
| 2006/0084111 A1 | 4/2006 | Ruan et al. |
| 2006/0088872 A1 | 4/2006 | Ahmadian et al. |
| 2006/0105348 A1 | 5/2006 | Lee et al. |
| 2006/0177842 A1 | 8/2006 | Wangh et al. |
| 2006/0292586 A1 | 12/2006 | Schroth et al. |
| 2007/0256430 A1 | 2/2007 | Anderson et al. |
| 2007/0077570 A1 | 4/2007 | Lao et al. |
| 2007/0178476 A1 | 8/2007 | Shima et al. |
| 2008/0108063 A1 | 5/2008 | Lucero et al. |
| 2008/0131875 A1 | 6/2008 | Hall |
| 2008/0176294 A1 | 7/2008 | Deiman et al. |
| 2008/0227108 A1 | 9/2008 | Morrison et al. |
| 2008/0305482 A1 | 12/2008 | Brentano et al. |

FOREIGN PATENT DOCUMENTS

| | | |
|---|---|---|
| EP | 1275738 A1 | 1/2003 |
| EP | 1598429 A1 | 11/2005 |
| EP | 1942196 A2 | 7/2008 |
| EP | 1 945 821 B1 | 1/2011 |
| GB | 2384308 A | 7/2003 |
| JP | 07-000198 | 1/1995 |
| JP | 09-065880 | 3/1997 |
| JP | 09-266800 | 10/1997 |
| JP | 11-113599 | 4/1999 |
| JP | 2004-187545 | 7/2004 |

(56) References Cited

FOREIGN PATENT DOCUMENTS

| | | |
|---|---|---|
| JP | 2005-192490 | 7/2005 |
| JP | 2005-192551 | 7/2005 |
| JP | 2005-224172 | 8/2005 |
| JP | 2005-318884 | 11/2005 |
| JP | 2005-341865 | 12/2005 |
| JP | 2008-048648 | 3/2008 |
| JP | 2008-048705 | 3/2008 |
| JP | 2009-539379 A | 11/2009 |
| WO | 90/03445 A1 | 4/1990 |
| WO | 91/15601 A1 | 10/1991 |
| WO | 91/17270 A1 | 11/1991 |
| WO | 97/39008 A1 | 10/1997 |
| WO | 0000638 A2 | 1/2000 |
| WO | 00/61807 A1 | 10/2000 |
| WO | 00/79009 A2 | 12/2000 |
| WO | 02/059353 A2 | 8/2002 |
| WO | 2004/068112 A2 | 8/2004 |
| WO | 2005/012548 A2 | 2/2005 |
| WO | 2005019479 A1 | 3/2005 |
| WO | 2006/026388 A2 | 3/2006 |
| WO | 2007/043751 A1 | 4/2007 |
| WO | 2007/067151 A1 | 6/2007 |
| WO | 2008/026582 A1 | 3/2008 |
| WO | 2008/045251 A2 | 4/2008 |

OTHER PUBLICATIONS

Weighardt et al., "A Simple Procedure for Enhancing PCR Specificity," Genome Research PCR Methods and Applications, 1993, pp. 77-80, vol. 3, Cold Spring Harbor Laboratory Press, NY USA.

White et al., "Detection of seven Candida species using the LightCycler system," J. Med. Microbiol., 2003, 52:229-238, London Lippincott Williams and Wilkins, U.K.

Winn-Deen, "Direct Fluorescence Detection of Allele-Specific PCR Products Using Novel Energy-Transfer Labeled Primers," Mol. Diagn., 1998, 3(4):217-222, Adis International, USA.

Zhou et al., "Snapback Primer Genotyping with Saturating DNA Dye and Melting Analysis," Clin. Chem., 2008, 54(10):1-9, American Association for Clinical Chemistry, USA.

PCT Search Report, International Application No. PCT/US07/13553, Oct. 19, 2007.

PCT Written Opinion, International Application No. PCT/US07/13553, Oct. 19, 2007.

International Search Rpt. for WO 2008/080029 dated Aug. 11, 2008.

EPO Office Action, European Patent Application No. 07 795 916.1, Nov. 27, 2008.

PCT International Preliminary Report of Patentability, International Application No. PCT/US07/013553, Dec. 24, 2008.

Extended Search Report, European Patent Application No. 08005731.8, dated Apr. 6, 2009.

EP Communication pursuant to Article 94(3) EPC, European Application 07795916.1, dated Apr. 23, 2009.

EP Communication pursuant to Article 94(3) and Rule 71(1) EPC for EP Application 07795916.1, dated Sep. 15, 2009.

Office Action (Restriction Req.), in Corresponding U.S. Appl. No. 11/810,834, Mar. 10, 2009.

Office Action in Corresponding U.S. Appl. No. 11/810,834, Jul. 6, 2009.

Office Action in Corresponding U.S. Appl. No. 11/810,834, Jan. 13, 2010.

Notice of Allowance in Corresponding U.S. Appl. No. 11/810,834, Jun. 30, 2010.

Issue Notification in Corresponding U.S. Appl. No. 11/810,834, Oct. 27, 2010.

EP Communication pursuant to Article 94(3) EPC in corresponding EP Application 08 005 731.8., Nov. 18, 2009.

EP Communication pursuant to Article 94(3) & Rule 71(1) EPC in corresponding EP Application 08 005 731.8., Feb. 15, 2011.

EP Decision to Grant pursuant to Rule 71(3) EPC in corresponding EP Application 07 795 916.1., Aug. 13, 2010.

EP Extended Search Report, European Patent Application No. 10015034.1, Jun. 8, 2011.

EP Communication under Rule 71(3) EPC, European Patent Application No. 08 005 731.8, Jul. 5, 2011.

EP Decision to Grant pursuant to Rule 71(3) EPC, European Patent Application No. 08 005 731.8, Nov. 10, 2011.

Examiner's first report, Australian Patent Application No. 2007258455, mailed Jan. 27, 2012.

Examiner's Report, Canadian Patent Application No. 2,659,543, mailed Mar. 1, 2012.

Communication pursuant to Article 94(3) EPC, European Patent Application No. 10 015 034.1-2402, 9 pages, dated Jul. 11, 2012.

Notice of Reasons for Rejection, Japanese Patent Application No. 2009-514407, mailed May 21, 2012.

Shuldiner et al., "RNA template-specific polymerase chain reaction (RS-PCR): a novel strategy to reduce dramatically false positives," Gene, 1990, (91):139-142, Elsevier, Amsterdam, NL.

Non-Final Rejection, U.S. Appl. No. 13/612,601, mailed Apr. 2, 2013.

Notice of Allowance and Fees Due, U.S. Appl. No. 13/612,601, mailed Jul. 2, 2013.

Examiner's Report, Canadian Patent Application No. 2,659,543, mailed Mar. 22, 2013.

Notice of Reasons for Rejection, Japanese Patent Application No. 2009-514407, mailed Sep. 14, 2012.

Afonina et al., "Minor Goove Binder-Conjugated DNA Probes for Quantitative DNA Detection by Hybridization-Triggered Fluorescence," BioTechniques, 2002, 32(4):940-949, Informa Healthcare USA, Inc., U.K.

Ayala et al. "New Primer Strategy Improves Precision of Differential Display," BioTechniques, 1995, 18(5):842-844, 846, 848, 850, Informa Healthcare USA, Inc., U.K.

Bonnet et al., "Thermodynamic basis of the chemical specificity of structured DNA probes," Proc. Natl. Acad. Sci. USA, 1999, 96: 6171-6176, National Academy of Sciences, USA.

Caetano-Anolies et al., "DNA Amplification Fingerprinting Using Arbitrary Mini-hairpin Oligonucleotide Primers," Bio/Technology, 1994, 12:619-623, Nature Pub. Co., USA.

Carr et al., "First Reported Case of Endocarditis Caused by Candida dubliniensis," J. Clin. Microbiol., 2005, 43 (6):3023-3026, American Society for Microbiology, USA.

Chou et al., "Prevention of pre-PCR mis-priming and primer dimerization improves low-copy-number amplifications," Nucleic Acids Res., 1992, 20(7):1717-1723, Oxford University Press, U.D.

Cox et al., "Investigation of infectious agents associated with arthritis by reverse transcription PCR of bacterial rRNA," Arthritis Res. Ther, 2003, 5:R1-R8, Open Access article—http://arthritis-research.com/content/5/1/R1.

Dreier et al., "Real-Time Polymerase Chain Reaction in Transfusion Medicine: Applications for Detection of Bacterial Contamination in Blood Products," Transfus Med. Rev., 2007, 21(3):237-254, Grune and Stratton, USA.

Didenko et al., "DNA Probes Using Fluorescence Resonance Energy Transfer (FRET): Designs and Applications," BioTechniques, Nov. 1, 2001, pp. 1106-1121, vol. 31(5), XP-001082961, Informa Life Sciences Publishing, Westborough, MA USA.

Erlich et al., "Recent Advances in the Polymerase Chain Reaction", Science, 1991, 252(5013):1643-1651, American Association for the Advancement of Science,USA.

Fan et al., "Parallel Genotyping of Human SNPs Using Generic High-density Oligonucleotide Tag Arrays," Genome Res., 2000, 10:853-860, Cold Spring Harbor Laboratory Press, USA.

Flindt et al., "Differentiating Vector-Derived mRNA from Contaminating DNA Templates by Inverse RT—PCR," BioTechniques, 2001, 31(6):1296-1299, Informa Healthcare USA, Inc., U.K.

Greisen et al., "PCR Primers and Probes for the 16S rRNA Gene of Most Species of Pathogenic Bacteria, Including Bacteria Found in Cerebrospinal Fluid," J. Clin. Microbiol., 1994, 32(2):335-351, American Society for Microbiology, USA.

Grzeskowiak et al., "Expression profiling of human idiopathic dilated cardiomyopathy," Cardiovasc Res., 2003, 59:400-411, Elsevier B.V., UK.

(56) References Cited

OTHER PUBLICATIONS

Hauser et al., "Transcriptional Profiling on all Open Reading Frames of *Saccharomyces cerevisiae*," Yeast, 1998, 14:1209-1221, John Wiley & Sons, Ltd., UK.

Hummelshoj et al., "Locked nucleic acid inhibits amplification of contaminating DNA in real-time PCR," BioTechniques, 2005, 38(4):605-610, Informa Healthcare USA, Inc., U.K.

Invitrogen, "High-performance real-time PCR detection with LUX Fluorogenic Primers", Expressions, 2002, 9 (6):2-3, Invitrogen Life Technologies, USA.

Jordan et al., "Real-Time Polymerase Chain Reaction for Detecting Bacterial DNA Directly from Blood of Neonates Being Evaluation for Sepsis," J. Mol. Diagn., 2005, 7(5):575-581, American Society for Investigative Pathology and the Association for Molecular Pathology, USA.

Kaderali, "Primer Design for Multiplexed Genotyping," Methods Mol. Biol., 2007, 402:269-285, Humana Press, USA.

Knuchel et al., "PCR-derived ssDNA Probes for Fluorescent In Situ Hybridization to HIV-1 RNA," J Histochem Cytochem, 2000, 48(2):285-293, Histochemical Society, USA.

Kunishima et al., Application of 16S ribosomal RNA gene amplification to the rapid identification of bacteria from blood culture bottles, Transfusion, 2000, 40:1420, Bois-Guillaume Centre Regional De Transfusion Sanguine Et Genetique Humaine, France.

Kutyavin et al., "3-Minor groove binder-DNA probes increase sequence specificity at PCR extension temperatures," Nucleic Acids Res., 2000, 28(2):655-661, Oxford University Press, U.K.

Kwok et al., "Avoiding false positives with PCR," Nature, 1989, 339:237-238, Nature Publishing Group, USA.

Levy et al., "Two-Temperature Tagged (2T-TA) PCR for Elimination of False Positives Due to Amplicon Contamination," Research Disclosure Journal, Nov. 2005, vol. 16(11), XP-007135635, Kenneth Mason Publications Ltd., Oxford, UK.

Li et al., "Primase-based whole genome amplification," Nucleic Acid Res., 2008, 36(13):1-10, Oxford University Press, U.K.

Lin et al., Correction of the N-Terminal Sequences of the Human Plastin Isoforms by Using Anchored Polymerase Chain Reaction: Identification of a Potential Calcium-Binding Domain, Mol. Cell. Biol., Apr. 1990, pp. 1818-1821, vol. 10 (4), American Society for Microbiology, Washington, DC. USA.

Loh et al., "Polymerase Chain Reaction with Single-Sided Specificity: Analysis of T Cell Receptor .delta. Chain," Science, 1989, 248(4888):217-220, American Association for the Advancement of Science, USA.

Maaroufi et al., "Rapid Detection of Candida albicans in Clinical Blood Samples by Using a TaqMan-Based PCR Assay," J. Clin. Microbiol., 2003, 41(7):3293-3298, American Society for Microbiology, USA.

Maiwald et al., "Characterization of contaminating DNA in Taq polymerase which occurs during amplification with a primer set for Legionella 5S ribosomal RNA," Mol. Cell. Probes, 1994, 8:11-14, Academic Press Limited, USA.

Morisset et al., "NAIMA: target amplification strategy allowing quantitative on—chip detection of GMOs," Nucleic Acids Res., 2008, pp. 1-11, Oxford University Press, U.K.

Mullis et al., "Specific Enzymatic Amplification of DNA In Vitro: The Polymerase Chain Reaction," Cold Spring Harbor Symposia on Quantitative Biol., 1986, pp. 263-273, vol. LI, Cold Spring Harbor Laboratory, NY USA.

Mullis et al., "Specific Synthesis of DNA In Vitro via a Polymerase-Catalyzed Chain Reaction," Methods in Enzymology, 1987, pp. 335-350, vol. 155, Academic Press, Inc., St. Louis, MO, USA.

Neilan et al., "A universal procedure for primer labeling of amplicons," Nucleic Acids Res., 1997, 25(14):2938-2939, Oxford University Press, U.K.

Nitsche et al., "Different Real-Time PCR Formats Compared for the Quantitative Detection of Human Cytomegalovirus DNA," Clinical Chemistry., 1999, pp. 1932-1937, vol. 45(11), American Society for Microbiology, Washington, D.C. USA.

Persing et al., Detection of Babesia microti by Polymerase Chain Reaction, J. Clin. Microbiol., 1992, pp. 2097-2103, vol. 30(8), American Society for Microbiology, Washington, DC. USA.

Qiagen, MinElute® Handbook—for minElute PCR Purification Kit, Gel Extraction Kit, and Reaction Cleanup Kit, 2004, pp. 3-36, Qiagen, USA.

Reyes et al., "Contaminating DNA in RNA Amplification by Polymerase Chain Reaction," Clin. Chem., 1992, 38 (6):1187, American Association for Clinical Chemistry, USA.

Roberts et al., "Effects of Prolonged Naloxone Infusion in Septic Shock," The Lancet, 1988, 699-702, The Lancet Ltd., UK.

Rothman et al., "Detection of Bacteremia in Emergency Department Patients at Risk for Infective Endocarditis Using Universal 16S rRNA Primers in a Decontaminated Polymerase Chain Reaction Assay," J. Infect. Dis., 2002, 186:1677-1681, University of Chicago Press, USA.

Rudney et al., "Actinobacillus actinomycetermcomitans, Porphyromonas gingivalis, and Tannerella forsythensis are Components of a Polymicrobial Intracellular Flora within Human Buccal Cells," J. Dent. Res., 2005, 84(1):59-63, International & American Associations for Dental Research, USA.

Rys et al., "Preventing False Positives: Quantitative Evaluation of Three Protocols for Inactivation of Polymerase Chain Reaction Amplification Products," J. Clin. Microbiol., 1991, 31(9):2356-2360, American Society for Microbiology, USA.

Scaramozzino et al., "Comparison of Flavivirus Universal Primer Pairs and Development of a Rapid, Highly Sensitive Heminested Reverse Transcriptase-PCR Assay for Detection of Flaviviruses Targeted to a Conserved Region of the NS5 Gene Sequences," J. Clin. Microbiol., 2001, 39(5):1922-1927, American Society for Microbiology, USA.

Schmidt et al., "Phylogenetic Identification of Uncultured Pathogens Using Ribosomal RNA Sequences," Meth Enzymol., 1994, 235(16):205-222, Academic Press, Inc., USA.

Shuber et al., "A Simplified Procedure for Developing Multiplex PCRs," Genome Research-Simplified Method for Multiplex PCR Development, 1995, pp. 488-493, vol. 5, Cold Spring Harbor Laboratory Press, NY USA.

Smith et al., "Exclusive Amplification of cDNA Template (EXACT) RT-PCR to Avoid Amplifying Contaminating Genomic Pseudogenes," BioTechniques, 2001, 31(4):776-782, Informa Healthcare USA, Inc., U.K.

Stathopoulou et al., "A highly specific real-time RT-PCR method for the quantitative determination of CK-19 mRNA positive cells in peripheral blood of patients with operable breast cancer," Int. J. Cancer, 2006, 119:1654-1659, Wiley-Liss, Inc., USA.

Tran, "Improved Multiplex PCR Using Conserved and Species-Specific 16S rRNA Gene Primers for Simultaneous Detection of Actinobacillus actinomycetemcomitans, Bacteroides forsythus, and Porphyromonas gingivalis," J. Clin. Microbiol., 1999, 37(11):3504-3508, Am. Society for Microbiology, USA.

TAGGED OLIGONUCLEOTIDES AND THEIR USE IN NUCLEIC ACID AMPLIFICATION METHODS

CROSS-REFERENCE TO RELATED APPLICATIONS

This application is a continuation of U.S. Pat. No. 8,580,510, filed Sep. 12, 2012, which is a continuation of U.S. Pat. No. 8,278,052, filed Sep. 13, 2011, which is a continuation of U.S. Pat. No. 8,034,570, filed Sep. 28, 2010, which is a divisional application of U.S. Pat. No. 7,833,716, filed Jun. 6, 2007, which claims priority to U.S. Provisional Application No. 60/811,581, filed Jun. 6, 2006, and U.S. Provisional Application No. 60/871,442, filed Dec. 21, 2006, the contents of each being incorporated herein by reference in their entirety.

FIELD OF THE INVENTION

This invention relates to methods, compositions, reaction mixtures and kits for the selective amplification of multiple copies of a specific nucleic acid sequence or "target sequence" which may be present either alone or as a component of a homogeneous or heterogeneous mixture of nucleic acids. The mixture of nucleic acids may be that found in a sample taken for diagnostic testing, screening of blood products, sterility testing, microbiological detection in food, water, beverage, industrial or environmental samples, research studies, preparing reagents or materials for other processes such as cloning, or for other purposes. The selective amplification of specific nucleic acid sequences, as described herein, is of particular value in any of a variety of detection assays for increasing the accuracy and reliability of such assays while at the same time reducing the preparation, purification and/or sterilization requirements for reagents used in the assays and for the environment in which the assays are performed.

DESCRIPTION OF THE RELATED ART

The detection and/or quantitation of specific nucleic acid sequences is an important technique for identifying and classifying microorganisms, diagnosing infectious diseases, measuring response to various types of treatment, and the like. Such procedures are also useful in detecting and quantitating microorganisms in foodstuffs, water, beverages, industrial and environmental samples, seed stocks, and other types of material where the presence of specific microorganisms may need to be monitored.

Numerous amplification-based methods for the detection and quantitation of target nucleic acids are well known and established in the art. The polymerase chain reaction, commonly referred to as PCR, uses multiple cycles of denaturation, annealing of primer pairs to opposite strands, and primer extension to exponentially increase copy numbers of the target sequence (e.g., Mullis et al., "Process for Amplifying, Detecting and/or Cloning Nucleic Acid Sequences," U.S. Pat. No. 4,683,195; Mullis, "Process for Amplifying Nucleic Acid Sequences," U.S. Pat. No. 4,683,202; Mullis et al., "Process for Amplifying, Detecting and/or Cloning Nucleic Acid Sequences," U.S. Pat. No. 4,800,159; Gelfand et al., "Reaction Mixtures for the Detection of Target Nucleic Acids," U.S. Pat. No. 5,804,375; Mullis et al. (1987) *Meth. Enzymol.* 155, 335-350; and Murakawa et al. (1988) *DNA* 7, 287-295).

In a variation called RT-PCR, reverse transcriptase (RT) is used to make a complementary DNA (cDNA) from RNA, and the cDNA is then amplified by PCR to produce multiple copies of DNA (Gelfand et al., "Reverse Transcription with Thermostable DNA Polymerases—High Temperature Reverse Transcription," U.S. Pat. Nos. 5,322,770 and 5,310,652).

Another well known amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g., Walker, G. et al. (1992), *Proc. Natl. Acad. Sci. USA* 89, 392-396; Walker et al., "Nucleic Acid Target Generation," U.S. Pat. No. 5,270,184; Walker, "Strand Displacement Amplification," U.S. Pat. No. 5,455,166; and Walker et al. (1992) *Nucleic Acids Research* 20, 1691-1696). Thermophilic SDA (tSDA) uses thermophilic endonucleases and polymerases at higher temperatures in essentially the same method (European Pat. No. 0 684 315).

Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278).

Transcription-based amplification methods commonly used in the art include nucleic acid sequence based amplification, also referred to as NASBA (e.g., Malek et al., U.S. Pat. No. 5,130,238); methods which rely on the use of an RNA replicase to amplify the probe molecule itself, commonly referred to as Qβ replicase (e.g., Lizardi, P. et al. (1988) *BioTechnol.* 6, 1197-1202); transcription-based amplification methods (e.g., Kwoh, D. et al. (1989) *Proc. Natl. Acad. Sci. USA* 86, 1173-1177) and self-sustained sequence replication (e.g., Guatelli, J. et al. (1990) *Proc. Natl. Acad. Sci. USA* 87, 1874-1878; Landgren (1993) *Trends in Genetics* 9, 199-202; and HELEN H. LEE et al., NUCLEIC ACID AMPLIFICATION TECHNOLOGIES (1997)).

Another transcription-based amplification method is transcription-mediated amplification, commonly referred to as TMA, which synthesizes multiple copies of a target nucleic acid sequence autocatalytically under conditions of substantially constant temperature, ionic strength, and pH, in which multiple RNA copies of the target sequence autocatalytically generate additional copies (e.g., Kacian et al., "Nucleic Acid Sequence Amplification Methods," U.S. Pat. No. 5,480,784; and Kacian et al., U.S. Pat. No. 5,399,491). TMA is a robust and highly sensitive amplification system with demonstrated efficacy, which overcomes many of the problems associated with PCR-based amplification systems. In particular, temperature cycling is not required.

Amplification assays are particularly well suited for the detection of microorganisms in the context of clinical laboratory testing, bioprocess monitoring, or any other setting in which the detection of microorganisms in a particular sample type is desired, by offering high sensitivity and rapid time-to-result relative to conventional microbiological techniques. In addition, amplification methods can be used in the detection of the vast number of microorganisms that are difficult or impossible to culture on synthetic media. Nevertheless, there are certain limitations associated with first-generation amplification assays that have limited their acceptance in certain settings, such as clinical microbiological laboratories. One inherent problem associated with the high sensitivity of nucleic acid amplification systems is that contaminating nucleic acid introduced into the amplification system (e.g., from one or more reagents used during amplification, from the technician performing the assay, from the environment in which the amplification is performed, etc.) can result in false positive results. For example, even extremely small amounts of nucleic acid contamination present in reagents and/or enzymes used in an amplification reaction, or in the environment in which the amplification reaction is performed, can give rise to a positive amplification signal despite the fact that the sequence of interest is not present in the nucleic acid sample being tested. This requires that significant effort be expended in sample preparation, purification, sterilization, etc., of the reagents used in amplification reactions to avoid or minimize false positive results.

Accordingly, there remains a need in the art for a robust nucleic acid amplification system that can selectively amplify one or more target nucleic acid sequences of interest while reducing or eliminating false positive results that can arise as a result of contaminating biological material, such as contaminating nucleic acid. There also remains a need for amplification systems that have reduced reagent purification and/or sterility requirements. As described further herein, the present invention meets these needs and offers other related advantages.

SUMMARY OF THE INVENTION

The present invention is directed generally to nucleic acid amplification methods and reaction mixtures that desirably reduce or eliminate false positive amplification signals resulting from contaminating biological material, e.g., nucleic acid, that may be present in one or more reagents, components or materials that are used in an amplification reaction or that are present in the environment in which an amplification reaction is performed. The invention further offers the advantage of requiring less stringent purification and/or sterility efforts than conventionally needed in order to ensure that enzymes and other reagents and components used in amplification reactions are free of bacterial and other nucleic acid contamination that may yield false positive results. Such components or materials include, but are not limited to, water, buffers, salts, solid supports (e.g., magnetically charged particles or beads), and receptacles (e.g., glassware or plasticware). Accordingly, the methods and reaction mixtures of the invention are useful in detecting and/or quantitating microorganisms in clinical samples, foodstuffs, water, industrial and environmental samples, seed stocks, and other types of material where the presence of microorganisms may need to be detected and/or monitored. The methods and reaction mixtures of the invention have particular advantages for the testing raw materials used in the production of products for the biotech, pharma, cosmetics and beverage industries, for release testing of final products, and for sterility screening to test for a class of organisms or total viable organisms in a material of interest (bacterial, fungal or both). In the clinical setting, the methods and reaction mixtures of the invention would be particularly useful for sepsis testing, especially septicemia, which is caused by pathogenic organisms and/or their toxins in the bloodstream.

According to one embodiment of the present invention, there are provided methods for the selective amplification of at least one target nucleic acid sequence, such as a DNA sequence or an RNA sequence, where the method comprises the steps of: (a) treating a target nucleic acid sequence in a nucleic acid sample, e.g., where the target nucleic acid is immobilized on a solid support, with a heterologous tag sequence to produce a tagged target nucleic acid sequence; (b) reducing in said sample the effective concentration of heterologous tag sequences which have not formed part of said tagged target nucleic acid sequence and are in a form capable of producing a tagged target nucleic acid sequence with said target nucleic acid sequence; and (c) subjecting said tagged target nucleic acid sequence to reagents and conditions sufficient for detectable amplification of the target nucleic acid sequence, where the subjecting step exposes the nucleic acid sample to a known contaminating source of the target nucleic acid sequence after step (b), and where detectable amplification of the target nucleic acid sequence is substantially limited to amplification of target nucleic acid sequence contributed by the tagged target nucleic acid sequence of step (a) and not by the target nucleic acid sequence contributed by the known contaminating source.

The methods of the invention are particularly useful where one or more reagents or components used are produced with a material known to be a contaminating source of a target nucleic acid sequence being amplified. In one example, one or more reagents used in the methods, such as nucleic acid polymerases, are produced using a microorganism containing the target nucleic acid sequence. In another example, components used in the methods, such as reaction vessels, pipette tips and solid supports for binding the tagged target nucleic acid sequences, may be a known contaminating source of the target nucleic acid sequence. In addition, the methods are useful where the environmental conditions in which amplification is performed include a known contaminating source of a target nucleic acid sequence, such as the ambient air, operator or analytical instrumentation.

In a more particular aspect of this embodiment, the tagged target nucleic acid sequence is immobilized on a solid support during step (b).

In another particular aspect, step (b) comprises diluting or removing heterologous tag sequences which have not formed part of the tagged target nucleic acid sequence from the nucleic acid sample. In an alternative aspect, step (b) comprises inactivating heterologous tag sequences which have not formed part of said tagged target nucleic acid sequence to produce an inactivated heterologous tag sequence. In a related aspect, the method further comprises removing the inactivated heterologous tag sequence from said nucleic acid sample during step (b). The heterologous tag sequence may be inactivated by blocking its ability to complex with the target nucleic acid sequence, using an enzyme to digest a component or cleave a site of a complexed portion of the heterologous tag sequence, chemically altering the heterologous tag sequence, or altering by other means the ability of the heterologous tag sequence to complex with the target nucleic acid sequence in an amplification reaction mixture.

In another aspect, the heterologous tag sequence is contained in a tagged oligonucleotide, where the tagged oligonucleotide comprises first and second regions, the first region comprising a target hybridizing sequence which hybridizes to a 3'-end of the target nucleic acid sequence and the second region comprising a tag sequence situated 5' to the target hybridizing sequence, and where the tag sequence does not stably hybridize to a target nucleic acid containing the target nucleic acid sequence.

In yet another aspect, the heterologous tag sequence has an active form during step (a) which permits the heterologous tag sequence to produce the tagged target nucleic acid sequence, and where the heterologous tag sequence which has not produced the tagged target nucleic acid sequence is converted to an inactive form in step (b) which blocks the heterologous tag sequence from producing a tagged target nucleic acid sequence during step (c).

The target hybridizing sequence, in certain aspects, is a universal oligonucleotide, such as a universal bacterial or fungal oligonucleotide.

Step (c) comprises producing amplification products in a nucleic acid amplification reaction using first and second oligonucleotides, the first oligonucleotide comprising a sequence which hybridizes to a 3'-end of the complement of the target nucleic acid sequence and the second oligonucleotide comprising a sequence which hybridizes to a complement of the tag sequence but which does not stably hybridize to the target nucleic acid sequence, wherein each of the amplification products comprises a base sequence which is substantially identical or complementary to the base sequence of the target nucleic acid sequence and further comprises a base sequence which is substantially identical or complementary to all or a portion of the tag sequence.

Various amplification methods are suitable for use in the present invention. For example, in one aspect, the amplification reaction is a PCR reaction. In another aspect, the target nucleic acid sequence is amplified by a transcription-based amplification reaction, preferably a TMA reaction, performed under isothermal conditions.

The target nucleic acid sequence amplified according to the methods can be any target nucleic acid sequence of interest, but will generally be a nucleic acid sequence obtained from a microorganism. Further, the method can be selective for the amplification of a target nucleic acid sequence contained in the nucleic acid of a single strain or species of microorganisms or in multiple species of microorganisms. Alternatively, the method can be selective for the amplification of multiple target nucleic acid sequences contained in the nucleic acid of multiple species of microorganisms, where, for example, the target hybridizing sequence of a tagged oligonucleotide hybridizes to a target region present in each of the multiple target nucleic acid sequences in step (a).

For example, in a particular aspect, the method is selective for the amplification of a target nucleic acid sequence contained in each of a plurality of target nucleic acids, and wherein the heterologous tag sequence produces a tagged target nucleic acid sequence with the target nucleic acid sequence of each of the plurality of target nucleic acids present in the nucleic acid sample in step (a). In a more particular aspect, the target nucleic acid sequence contained in each of the plurality of target nucleic acids is the same nucleic acid sequence.

In another particular aspect, the method is selective for the amplification of multiple bacterial or fungal target nucleic acid sequences, e.g., wherein the multiple bacterial or fungal target nucleic acid sequences are ribosomal nucleic acid sequences.

In another particular aspect, the method is selective for the amplification of target nucleic acid sequences obtained from members of a group of bacterial species including *Staphylococci* spp. (e.g., *Staphylococcus aureus*, *Staphylococcus epidermis* and *Staphylococcus haemolyticus*), *Steptococci* spp. (e.g., *Streptococcus pneumoniae*, *Streptococcus pyogenes*, *Streptococcus agalactiae*, *Streptococcus mitis*, *Viridans streptococci* and beta-hemolytic *streptococci*), *Enterococcus* spp. (e.g., *Enterococcus faecium* and *Enterococcus faecalis*), *Escherichia* spp. (e.g., *Escherichia coli*), *Klebsiella* spp. (e.g., *Klebsiella pneumoniae* and *Klebsiella oxytoca*), *Pseudomonas* spp. (e.g., *Pseudomonas aeruginosa*), *Enterobacter* spp. (e.g., *Enterobacter cloacae* and *Enterobacter aerogenes*), *Proteus* spp. (e.g., *Proteus mirabilis*), *Bacterioides* spp., *Clostridium* spp., *Serratia* spp. (e.g., *Serratia marcescens*), *Acinetobacter* spp. (e.g., *Acinetobacter baumannii*) and *Stenotrophomonas* spp. (e.g., *Stenotrophomonas maltophilia*). At least a portion of these microorganisms would be appropriate for detection in a sepsis test.

In another aspect, the method is selective for the amplification of target nucleic acid sequences obtained from members of a group of fungal species including *Candida* spp. (e.g., *Candida albicans*, *Candida tropicalis*, *Candida glabrata*, *Candida parapsilosis*, *Candida lusitaniae*, *Candida krusei*, *Candida zeylanoides*, *Candida guilliermondi*, *Candida pseudotropicalis* and *Candida famata*), *Histoplama capsulatum*, *Cryptococcus* spp. (e.g., *Cryptococcus neoformans*, *Cryptococcus albidus* and *Cryptococcus laurentii*) *Coccidioides* spp. (e.g., *Coccidioides immitis*), *Trichosporon* spp. (e.g., *Trichosporon cutaneum*), *Malassezia* spp. (e.g., *Malassezia furfur*), *Rhodotorula* spp., *Nocardia* spp. (e.g., *Nocardia asteroides*), *Fusarium* spp. and *Asperigillus* spp. (e.g., *Asperigillus fumigatus*). At least a portion of these microorganisms would be appropriate for detection in a sepsis test.

In yet another aspect, at least a portion of a nucleic acid sample used in the methods is obtained from a clinical, water, industrial, environmental, seed, beverage or food source.

The methods are particularly well suited, in certain aspects, for use in sterility testing or diagnostic testing for sepsis.

According to another embodiment of the invention, there is provided a method for the selective amplification of at least one target nucleic acid sequence from a nucleic acid sample, the method comprising the steps of: (a) treating a nucleic acid sample comprising a target nucleic acid sequence with a tagged oligonucleotide comprising first and second regions, the first region comprising a target hybridizing sequence which hybridizes to a 3'-end of the target nucleic acid sequence and the second region comprising a tag sequence situated 5' to the target hybridizing sequence, where the second region does not stably hybridize to a target nucleic acid containing the target nucleic acid sequence; (b) reducing in said nucleic acid sample the effective concentration of unhybridized tagged oligonucleotide having an active form in which a target hybridizing sequence of said unhybridized tagged oligonucleotide is available for hybridization to said target nucleic acid sequence; and (c) producing amplification products in a nucleic acid amplification reaction using first and second oligonucleotides, where the first oligonucleotide comprises a hybridizing sequence which hybridizes to a 3'-end of the complement of the target nucleic acid sequence and the second oligonucleotide comprises a hybridizing sequence which hybridizes to the complement of the tag sequence, where the second oligonucleotide does stably hybridize to the target nucleic acid, and where each of the amplification products comprises a base sequence which is substantially identical or complementary to the base sequence of the target nucleic acid sequence and further comprises a base sequence which is substantially identical or complementary to all or a portion of the tag sequence.

In one aspect of the above methods, at least one target nucleic acid sequence is immobilized on a solid support during step (b). In another aspect, step (b) does not include the use of an enzyme having a nuclease activity.

The effective concentration of unhybridized tagged oligonucleotide in an active form prior to amplification is preferably reduced by diluting the nucleic acid sample or by inactivating and/or removing the unhybridized tagged oligonucleotide. In one aspect, step (b) comprises inactivating unhybridized tagged oligonucleotide so that the unhybridized tagged oligonucleotide does not stably hybridize to the target nucleic acid sequence during step (c). In one example of inactivation, a tagged oligonucleotide has an active form during step (a) which permits the target hybridizing sequence to hybridize to the target nucleic acid sequence, and where unhybridized tagged oligonucleotide is converted to an inactive form in step (b) which blocks or prevents the tagged oligonucleotide from hybridizing to the target nucleic acid sequence during step (c). The tagged oligonucleotide may be inactivated by blocking the target hybridizing sequence from hybridizing to the target nucleic acid sequence, using an enzyme to digest a component or cleave a site of a duplex formed between the target hybridizing sequence and the target nucleic acid sequence, chemically altering the target hybridizing sequence, or altering by other means the ability of the tagged oligonucleotide to hybridize to the target nucleic acid sequence in an amplification reaction mixture.

In a related embodiment, the conditions of steps (b) and (c) are less stringent than the conditions of step (a). In another related embodiment, the temperature of the nucleic acid sample is lowered between steps (a) and (b).

In another example where step (b) comprises inactivating unhybridized tagged oligonucleotide, unhybridized tagged oligonucleotide from step (a) is converted from a single-stranded form to a duplexed form in step (b). The duplexed form may be a hairpin tag molecule comprising a tag closing sequence joined to a 5'-end of the tagged oligonucleotide, where the tag closing sequence hybridizes to the target hybridizing sequence under the conditions of step (b), thereby blocking hybridization of unhybridized tagged oligonucleotide from step (a) to the target nucleic acid sequence in steps (b) and (c). In another aspect, the tag closing sequence is joined to the tagged oligonucleotide by a non-nucleotide linker. For example, a 5'-end of the tag closing sequence may be joined to a 5'-end of the tagged oligonucleotide.

The tagged oligonucleotide can also further comprise a third region containing a promoter for an RNA polymerase, the third region being situated 5' to the second region.

In another aspect, the tag closing sequence is modified to prevent the initiation of DNA synthesis therefrom.

According to another aspect, a 3'-terminal base of the target hybridizing sequence is hybridized to a 5'-terminal base of the tag closing sequence. In another aspect, a 3'-end of the tag closing sequence is joined to a 5'-end of the tagged oligonucleotide.

In still another aspect, the target hybridizing sequence is hybridized to a tag closing oligonucleotide in step (b), the tagged oligonucleotide and the tag closing oligonucleotide being distinct molecules. The tag closing oligonucleotide may be modified, if desired, to prevent the initiation of DNA synthesis therefrom.

Further, in certain aspects, a 3'-terminal base of the target hybridizing sequence is hybridized to a 5'-terminal base of the tag closing oligonucleotide.

In certain other aspects, the tagged oligonucleotide and the tag closing oligonucleotide are both present in the nucleic acid sample during step (a), and where the target hybridizing sequence favors hybridization to the target nucleic acid sequence over the tag closing oligonucleotide in step (a).

As noted above, the methods of the invention can employ any of a variety of amplification techniques. In certain instances it may be preferred that an isothermal amplification reaction is used, such as a transcription-based amplification reaction, preferably TMA or real-time TMA.

In a particular aspect, the first oligonucleotide comprises a promoter for an RNA polymerase which is situated 5' to the hybridizing sequence. In another aspect, the second oligonucleotide comprises a promoter for an RNA polymerase which is situated 5' to the hybridizing sequence, and where the tagged oligonucleotide further comprises a promoter for an RNA polymerase which is situated 5' to the second region.

The target nucleic acid sequence amplified according to the methods can be any target nucleic acid sequence of interest, but will generally be a nucleic acid sequence obtained from a microorganism. Further, the method can be selective for the amplification of a target nucleic acid sequence contained in the nucleic acid of a single strain or species of microorganisms or in multiple species of microorganisms. Alternatively, the method can be selective for the amplification of multiple target nucleic acid sequences contained in the nucleic acid of multiple species of microorganisms, where, for example, the target hybridizing sequence of a tagged oligonucleotide hybridizes to a target region present in each of the multiple target nucleic acid sequences in step (a).

In another aspect, the method is selective for the amplification of a target nucleic acid sequence contained in each of a plurality of target nucleic acids, and wherein the target hybridizing sequence hybridizes to a 3'-end of the target nucleic acid sequence of each of the plurality of target nucleic acids present in the nucleic acid sample in step (a). In another aspect, the target nucleic acid sequence contained in each of said plurality of target nucleic acids is the same nucleic acid sequence.

In a particular embodiment, the method is selective for the amplification of multiple bacterial or fungal target nucleic acid sequences, e.g., wherein the multiple bacterial or fungal target nucleic acid sequences are ribosomal nucleic acid sequences.

In a more particular embodiment, the method is selective for the amplification of target nucleic acid sequences obtained from members of a group of bacterial species including *Staphylococci* spp. (e.g., *Staphylococcus aureus, Staphylococcus epidermis* and *Staphylococcus haemolyticus*), *Steptococci* spp. (e.g., *Streptococcus pneumoniae, Streptococcus pyogenes, Streptococcus agalactiae, Streptococcus mitis, Viridans streptococci* and beta-hemolytic *streptococci*), *Enterococcus* spp. (e.g., *Enterococcus faecium* and *Enterococcus faecalis*), *Escherichia* spp. (e.g., *Escherichia coli*), *Klebsiella* spp. (e.g., *Klebsiella pneumoniae* and *Klebsiella oxytoca*), *Pseudomonas* spp. (e.g., *Pseudomonas aeruginosa*), *Enterobacter* spp. (e.g., *Enterobacter cloacae* and *Enterobacter aerogenes*), *Proteus* spp. (e.g., *Proteus mirabilis*), *Bacterioides* spp., *Clostridium* spp., *Serratia* spp. (e.g., *Serratia marcescens*), *Acinetobacter* spp. (e.g., *Acinetobacter baumannii*) and *Stenotrophomonas* spp. (e.g., *Stenotrophomonas maltophilia*). At least a portion of these microorganisms would be appropriate for detection in a sepsis test.

In another particular embodiment, the method is selective for the amplification of target nucleic acid sequences obtained from members of a group of fungal species including *Candida* spp. (e.g., *Candida albicans, Candida tropicalis, Candida glabrata, Candida parapsilosis, Candida lusitaniae, Candida krusei, Candida zeylanoides, Candida guilliermondi, Candida pseudotropicalis* and *Candida famata*), *Histoplama capsulatum, Cryptococcus* spp. (e.g., *Cryptococcus neoformans, Cryptococcus albidus* and *Cryptococcus laurentii*) *Coccidioides* spp. (e.g., *Coccidioides immitis*), *Trichosporon* spp. (e.g., *Trichosporon cutaneum*), *Malassezia* spp. (e.g., *Malassezia furfur*), *Rhodotorula* spp., *Nocardia* spp. (e.g., *Nocardia asteroides*), *Fusarium* spp. and

*Asperigillus* spp. (e.g., *Asperigillus fumigatus*). At least a portion of these microorganisms would be appropriate for detection in a sepsis test.

In certain aspects, the target hybridizing sequence hybridizes to a 3'-end of each of multiple target nucleic acid sequences present in the nucleic acid sample in step (a). Further, the first oligonucleotide hybridizes to a 3'-end of the complement of each of the multiple target nucleic acid sequences present in the nucleic acid sample in step (c).

The method can also comprise a plurality of first oligonucleotides, each of the plurality of first oligonucleotides hybridizing to a 3'-end of the complement of at least one but less than all of the multiple target nucleic acid sequences present in the nucleic acid sample in step (c).

The tagged oligonucleotide, in a particular embodiment of the invention, is a universal bacterial oligonucleotide or a universal fungal oligonucleotide. Such tagged oligonucleotides are particularly well suited to methods for sterility testing, such as methods for analyzing bioprocess materials or which are diagnostic for sepsis.

In a more particular aspect, the target hybridizing sequence hybridizes to a 3'-end of the target nucleic acid of each of the plurality of target nucleic acids present in the nucleic acid sample in step (a), the plurality of target nucleic acids belonging to a class of microorganisms selected from the group consisting of Eubacteria, Gram-positive bacteria, Gram-negative bacteria and fungi. In another aspect, each of plurality of target nucleic acids is a ribosomal nucleic acid.

In another aspect of the invention, the multiple target nucleic acid sequences include members belonging to a class of bacterial microorganisms selected from the group consisting of *Staphylococci* spp. (e.g., *Staphylococcus aureus, Staphylococcus epidermis* and *Staphylococcus haemolyticus*), *Steptococci* spp. (e.g., *Streptococcus pneumoniae, Streptococcus pyogenes, Streptococcus agalactiae, Streptococcus mitis, Viridans streptococci* and beta-hemolytic *streptococci*), *Enterococcus* spp. (e.g., *Enterococcus faecium* and *Enterococcus faecalis*), *Escherichia* spp. (e.g., *Escherichia coli*), *Klebsiella* spp. (e.g., *Klebsiella pneumoniae* and *Klebsiella oxytoca*), *Pseudomonas* spp. (e.g., *Pseudomonas aeruginosa*), *Enterobacter* spp. (e.g., *Enterobacter cloacae* and *Enterobacter aerogenes*), *Proteus* spp. (e.g., *Proteus mirabilis*), *Bacterioides* spp., *Clostridium* spp., *Serratia* spp. (e.g., *Serratia marcescens*), *Acinetobacter* spp. (e.g., *Acinetobacter baumannii*) and *Stenotrophomonas* spp. (e.g., *Stenotrophomonas maltophilia*). At least a portion of these microorganisms would be appropriate for detection in a sepsis test.

In a further aspect of the invention, the multiple target nucleic acid sequences include members belonging to a class of fungal microorganisms selected from the group consisting of *Candida* spp. (e.g., *Candida albicans, Candida tropicalis, Candida glabrata, Candida parapsilosis, Candida lusitaniae, Candida krusei, Candida zeylanoides, Candida guilliermondi, Candida pseudotropicalis* and *Candida famata*), *Histoplama capsulatum, Cryptococcus* spp. (e.g., *Cryptococcus neoformans, Cryptococcus albidus* and *Cryptococcus laurentii*) *Coccidioides* spp. (e.g., *Coccidioides immitis*), *Trichosporon* spp. (e.g., *Trichosporon cutaneum*), *Malassezia* spp. (e.g., *Malassezia furfur*), *Rhodotorula* spp., *Nocardia* spp. (e.g., *Nocardia asteroides*), *Fusarium* spp. and *Asperigillus* spp. (e.g., *Asperigillus fumigatus*). At least a portion of these microorganisms would be appropriate for detection in a sepsis test.

The nucleic acid sample is often exposed to a known contaminating source of the target nucleic acid sequence after step (b), and, accordingly, the described methods provide that the production of amplification products is substantially limited to amplification of target nucleic acid sequence contributed by the nucleic acid sample and not by the contaminating source of the target nucleic acid sequence. For example, one or more reagents or components used in the amplification reaction is a known contaminating source of the target nucleic acid sequence. Alternatively, or in addition, one or more reagents are produced with a material known to be a contaminating source of the target nucleic acid sequence, such as nucleic acid polymerases produced using microorganisms known to contain the target nucleic acid sequence. Further, the environmental conditions in which the method is performed may include a known contaminating source of the target nucleic acid sequence. In a particular aspect, at least a portion of said nucleic acid is obtained from a clinical, water, industrial, environmental, seed, beverage or food source.

According to another embodiment of the present invention, the target nucleic acid sequence is an RNA target sequence, and step (c) comprises: extending the tagged oligonucleotide hybridized to the target nucleic acid sequence in a primer extension reaction with a DNA polymerase to produce a first primer extension product comprising a region complementary to the target nucleic acid sequence; separating the first primer extension product from the target nucleic acid using an enzyme which selectively degrades that portion of the target nucleic acid hybridized to the first primer extension product; treating the first primer extension product with the first oligonucleotide, the first oligonucleotide being a promoter oligonucleotide comprising first and second regions, the first region comprising a hybridizing sequence which hybridizes to a region of the first primer extension product that is complementary to a 5'-end of the target nucleic acid sequence to form a promoter oligonucleotide:first primer extension product hybrid, and the second region comprising a promoter for an RNA polymerase which is situated 5' to the first region; transcribing from the promoter oligonucleotide:first primer extension product hybrid multiple copies of a first RNA product complementary to at least a portion of the first primer extension product using an RNA polymerase which recognizes the promoter and initiates transcription therefrom, where the base sequence of the first RNA product is substantially identical to the base sequence of the target nucleic acid sequence and the complement of the tag sequence; treating the first RNA product with the second oligonucleotide, the second oligonucleotide being a priming oligonucleotide which hybridizes to the complement of the tag sequence to form a priming oligonucleotide:first RNA product hybrid such that a primer extension reaction can be initiated from the priming oligonucleotide; extending the priming oligonucleotide in a primer extension reaction with a DNA polymerase to produce a second primer extension product complementary to the first RNA product, the second primer extension product having a 3'-end which is complementary to a 5'-end of the first RNA product; separating the second primer extension product from the first RNA product using an enzyme which selectively degrades said first RNA product; treating the second primer extension product with the promoter oligonucleotide to form a promoter oligonucleotide:second primer extension product hybrid; extending a 3'-end of the second primer extension product in the promoter oligonucleotide:second primer extension product hybrid to add a sequence complementary to the second region of the promoter oligonucleotide; and transcribing from the promoter oligonucleotide:second primer extension product hybrid multiple copies of a second RNA product complementary to the second primer extension product using the RNA polymerase, wherein the base sequence of the second RNA product is substantially identical to the base sequence of the target nucleic acid sequence and the complement of the tag sequence.

In another aspect of this embodiment of the invention, step (a) further comprises treating the nucleic acid sample with a binding molecule which binds to the target nucleic acid adjacent to or near a 5'-end of the target nucleic acid sequence, and where the first primer extension product has a 3'-end which is determined by the binding molecule and which is complementary to the 5'-end of the target nucleic acid sequence.

In another aspect, step (c) of the above embodiment further comprises extending a 3'-end of the first primer extension product in the promoter oligonucleotide:first primer extension product hybrid to add a sequence complementary to the promoter. In yet another aspect, the promoter oligonucleotide is modified to prevent the initiation of DNA synthesis therefrom.

The promoter oligonucleotide hybridized to the first primer extension product is extended with a DNA polymerase to produce a primer extension product complementary to the first primer extension product; and the promoter oligonucleotide hybridized to said second primer extension product is extended with a DNA polymerase to produce a primer extension product complementary to the second primer extension product.

The separating steps of the described methods may be performed with a ribonuclease activity provided by the DNA polymerase. Alternatively, the separating steps are performed with a ribonuclease activity provided by an enzyme other than said DNA polymerase.

According to another embodiment of the present invention, the target nucleic acid sequence is an RNA target sequence, and step (c) comprises: extending the tagged oligonucleotide hybridized to the target nucleic acid sequence in a primer extension reaction with a DNA polymerase to produce a first primer extension product comprising a region complementary to the target nucleic acid sequence, where the tagged oligonucleotide further comprises a third region situated 5' to the second region, the third region comprising a promoter for an RNA polymerase; separating the first primer extension product from the target nucleic acid using an enzyme which selectively degrades that portion of the target nucleic acid hybridized to the first primer extension product; treating the first primer extension product with the first oligonucleotide, the first oligonucleotide being a priming oligonucleotide which hybridizes to a region of the first primer extension product that is complementary to a 5'-end of the target nucleic acid sequence to form a priming oligonucleotide:first primer extension product hybrid such that a primer extension reaction can be initiated from the priming oligonucleotide; extending the priming oligonucleotide in a primer extension reaction with a DNA polymerase to produce a second primer extension product complementary to the first primer extension product; and using the second primer extension product as a template to transcribe multiple copies of a first RNA product complementary to at least a portion of the second primer extension product using an RNA polymerase which recognizes the promoter and initiates transcription therefrom, where the base sequence of the first RNA product is substantially identical to the base sequence of the tag sequence and the complement of the target nucleic acid sequence.

In another aspect of this embodiment, step (c) further comprises: treating the first RNA product with the priming oligonucleotide to form a priming oligonucleotide:first RNA product hybrid such that a primer extension reaction can be initiated from the priming oligonucleotide; extending the priming oligonucleotide in a primer extension reaction with a DNA polymerase to produce a third primer extension product complementary to the first RNA product, the third primer extension product having a 3'-end which is complementary to a 5'-end of the first RNA product; separating the third primer extension product from the first RNA product using an enzyme which selectively degrades the first RNA product; treating the third primer extension product with the second oligonucleotide, the second oligonucleotide being a promoter oligonucleotide comprising first and second regions, the first region comprising a hybridizing sequence which hybridizes to the complement of the tag sequence to form a promoter oligonucleotide:third primer extension product hybrid such that a primer extension reaction can be initiated from the promoter oligonucleotide, and the second region comprising a promoter for an RNA polymerase which is situated 5' to the first region; extending the promoter oligonucleotide in a primer extension reaction with the DNA polymerase to produce a fourth primer extension product complementary to the third primer extension product; extending the third primer extension product to add a sequence complementary to the promoter; transcribing from the promoter oligonucleotide:third primer extension product hybrid multiple copies of a second RNA product complementary to the third primer extension product using an RNA polymerase which recognizes the promoter and initiates transcription therefrom, where the base sequence of the second RNA product is substantially identical to the base sequence of the tag sequence and the complement of the target nucleic acid sequence.

In another aspect of this embodiment, the separating steps are performed with a ribonuclease activity provided by the DNA polymerase. Alternatively, the separating steps are performed with a ribonuclease activity provided by an enzyme other than the DNA polymerase.

According to another embodiment of the present invention, the target nucleic acid sequence is a DNA target sequence, and step (c) comprises: extending the tagged oligonucleotide hybridized to the target nucleic acid sequence in a primer extension reaction with a DNA polymerase to produce a first primer extension product comprising a region complementary to the target nucleic acid sequence; treating the first primer extension product with the first oligonucleotide, the first oligonucleotide being a promoter oligonucleotide comprising first and second regions, the first region comprising a hybridizing sequence which hybridizes to a region of the first primer extension product that is complementary to a 5'-end of the target nucleic acid sequence to form a promoter oligonucleotide:first primer extension product hybrid, and the second region being a promoter for an RNA polymerase which is situated 5' to the first region; transcribing from the promoter oligonucleotide:first primer extension product hybrid multiple copies of a first RNA product complementary to at least a portion of the first primer extension product using an RNA polymerase which recognizes the promoter and initiates transcription therefrom, where the base sequence of the first RNA product is substantially identical to the base sequence of the target nucleic acid sequence and the complement of the tag sequence; treating the first RNA product with the second oligonucleotide, the second oligonucleotide being a priming oligonucleotide which hybridizes to the complement of the tag sequence to form a priming oligonucleotide:first RNA product hybrid such that a primer extension reaction can be initiated from the priming oligonucleotide; extending the priming oligonucleotide in a primer extension reaction with a DNA polymerase to give a second primer extension product comprising the complement of the first RNA product, the second primer extension product having a 3'-end which is complementary to a 5'-end of the first RNA product; separating the second primer extension product from the first RNA product using an enzyme which selectively degrades the first RNA product; treating the second primer extension product with the promoter oligonucleotide to form a promoter oligonucleotide:second primer extension product hybrid; extending a 3'-end of the second primer extension product in the promoter oligonucleotide:second primer extension product hybrid to add a sequence complementary to the promoter; and transcribing from the promoter oligonucleotide:second primer extension product hybrid multiple copies of a second RNA product complementary to the second primer extension product using the RNA polymerase, where the base sequence of the second RNA product is substantially identical to the base sequence of the target nucleic acid sequence and the complement of the tag sequence.

In one aspect of this embodiment, the promoter oligonucleotide is modified to prevent the initiation of DNA synthesis therefrom.

In another aspect, step (a) further comprises: treating the nucleic acid sample with a displacer oligonucleotide which hybridizes to the target nucleic acid upstream from the tagged oligonucleotide such that a primer extension reaction can be initiated from the displacer oligonucleotide; and extending the displacer oligonucleotide in a primer extension reaction with a DNA polymerase to produce a third primer extension product that displaces said first primer extension product from the target nucleic acid.

In yet another embodiment, step (a) further comprises treating the nucleic acid sample with a binding molecule which binds to the target nucleic acid adjacent to or near a 5'-end of the target nucleic acid sequence, where the first primer extension product has a 3'-end which is determined by said binding molecule and which is complementary to the 5'-end of the target nucleic acid sequence.

In a more particular aspect, step (c) further comprises extending a 3'-end of the first primer extension product in the promoter oligonucleotide:first primer extension product hybrid to add a sequence complementary to the promoter sequence.

In another particular aspect, step (c) further comprises: extending the promoter oligonucleotide hybridized to the first primer extension product with a DNA polymerase to produce a primer extension product complementary to the first primer extension product; and extending the promoter oligonucleotide hybridized to the second primer extension product with a DNA polymerase to produce a primer extension product complementary to the second primer extension product.

The separating steps, in one embodiment, are performed by a ribonuclease activity provided by said DNA polymerase. Alternatively, the separating steps are performed by a ribonuclease activity provided by an enzyme other than said DNA polymerase.

Another embodiment of the present invention provides a kit for use in the selective amplification of at least one target nucleic acid sequence from a nucleic acid sample, the kit comprising: a tagged oligonucleotide comprising a first region comprising a target hybridizing sequence which hybridizes to a 3'-end of a target nucleic acid sequence under a first set of conditions so that the first region can be extended in a template-dependent manner in the presence of a DNA polymerase, and a second region comprising a tag sequence situated 5' to the first region, where the second region does not stably hybridize to a target nucleic acid containing the target nucleic acid sequence under the first set of conditions; a tag closing sequence which hybridizes to the target hybridizing sequence under a second set of conditions, thereby blocking hybridization of the tagged oligonucleotide to the target nucleic acid sequence, where the tag closing sequence does not stably hybridize to the target hybridizing sequence under the first set of conditions; and a first priming oligonucleotide which hybridizes to the complement of the tag sequence under the second set of conditions so that the first priming oligonucleotide can be extended in a template-dependent manner in the presence of a DNA polymerase.

In a more particular aspect of this embodiment, the tagged oligonucleotide further comprises a third region containing a promoter for an RNA polymerase, the third region being situated 5' to the second region.

In another aspect, the 3'-terminal base of the target hybridizing sequence hybridizes to a 5'-terminal base of the tag closing sequence when the target hybridizing sequence is not hybridized to the target nucleic acid sequence under the second set of conditions.

In yet another aspect, the 5'-end of the tag closing sequence includes a moiety for stabilizing a duplex formed between the tag closing sequence and the target hybridizing sequence when the target hybridizing sequence is not hybridized to the target nucleic acid sequence under the second set of conditions.

In another aspect, the tagged oligonucleotide and the tag closing sequence constitute distinct molecules, the tag closing sequence being a tag closing oligonucleotide. Alternatively, the tagged oligonucleotide and the tag closing sequence are contained in the same molecule.

The tag closing sequence may be joined to the tagged oligonucleotide by a non-nucleotide linker, for example a non-nucleotide linker comprising at least one of abasic nucleotides and polyethylene glycol.

In another aspect, a 3'-end of the tag closing sequence is joined to a 5'-end of the tagged oligonucleotide. Alternatively, a 5'-end of the tag closing sequence is joined to a 5'-end of the tagged oligonucleotide.

In yet another aspect, the tag closing sequence hybridizes to the target hybridizing sequence to form an antiparallel duplex when the target hybridizing sequence is not hybridized to the target nucleic acid sequence under the second set of conditions.

In another aspect, the tag closing sequence is modified to prevent the initiation of DNA synthesis therefrom, for example by including a blocking moiety situated at its 3'-terminus.

In another aspect, the tag closing sequence hybridizes to the target hybridizing sequence to form a parallel duplex when the target hybridizing sequence is not hybridized to the target nucleic acid sequence under the second set of conditions.

In yet another aspect, the duplex comprises a 3'-terminal base of the target hybridizing sequence hybridized to a 3'-terminal base of the tag closing sequence.

The tag closing sequence, in this aspect, may be modified to prevent the initiation of DNA synthesis therefrom, for example by including a blocking moiety situated at its 3'-terminus.

In another aspect of this embodiment, the first priming oligonucleotide does stably hybridize to the target nucleic acid and, thereby, participates in detectable amplification of the target nucleic acid sequence under the second set of conditions.

In another aspect, the kit further comprises a second priming oligonucleotide which hybridizes to the complement of a 5'-end of the target nucleic acid sequence under the second set of conditions so that the second priming oligonucleotide can be extended in a template-dependent manner in the presence of a DNA polymerase.

In yet another aspect, a kit of the invention further comprises a promoter oligonucleotide comprising first and second regions, the first region comprising a hybridizing sequence which hybridizes to the complement of a 5'-end of the target nucleic acid sequence under the second set of conditions, and the second region comprising a promoter for an RNA polymerase which is situated 5' to the first region.

The promoter oligonucleotide, in this aspect, may be modified to prevent the initiation of DNA synthesis therefrom, for example by including a blocking moiety situated at its 3'-terminus.

In yet another aspect, the promoter oligonucleotide can be extended in a template-dependent manner in the presence of a DNA polymerase when the hybridizing sequence is hybridized to the complement of the 5'-end of the target nucleic acid sequence under the second set of conditions.

The kits of the invention, in certain aspects, may also further comprise one or more reagents or components selected from any one or more of a DNA polymerase (such as a reverse transcriptase), an RNA polymerase, nucleoside triphosphates, a solid support for binding a complex comprising the target nucleic acid and the tagged oligonucleotide. In another aspect, the tagged oligonucleotide is free in solution.

In another aspect, the kit does not include a restriction enzyme capable of cleaving a duplex formed between the tag closing sequence and the target hybridizing sequence under the second set of conditions.

In yet another aspect, the target hybridizing sequence hybridizes to a 3'-end of multiple target nucleic acid sequences under the first set of conditions.

In another embodiment, the tagged oligonucleotide is a universal bacterial or a universal fungal oligonucleotide. For example, in one aspect, the target hybridizing sequence hybridizes to target region at a 3'-end of one or more target nucleic acid sequences, the target region being present in a plurality of microorganisms belonging to a class of microorganisms selected from the group consisting of Eubacteria, Gram-positive bacteria, Gram-negative bacteria and fungi under the first set of conditions. In another embodiment, said one or more target nucleic acid sequences are ribosomal nucleic acid sequences.

In a more particular aspect, the microorganisms belong to a class of bacterial microorganisms selected from the group consisting *Staphylococci* spp. (e.g., *Staphylococcus aureus, Staphylococcus epidermis* and *Staphylococcus haemolyticus*), *Steptococci* spp. (e.g., *Streptococcus pneumoniae, Streptococcus pyogenes, Streptococcus agalactiae, Streptococcus mitis, Viridans streptococci* and beta-hemolytic streptococci), *Enterococcus* spp. (e.g., *Enterococcus faecium* and *Enterococcus faecalis*), *Escherichia* spp. (e.g., *Escherichia coli*), *Klebsiella* spp. (e.g., *Klebsiella pneumoniae* and *Klebsiella oxytoca*), *Pseudomonas* spp. (e.g., *Pseudomonas aeruginosa*), *Enterobacter* spp. (e.g., *Enterobacter cloacae* and *Enterobacter aerogenes*), *Proteus* spp. (e.g., *Proteus mirabilis*), *Bacterioides* spp., *Clostridium* spp., *Serratia* spp. (e.g., *Serratia marcescens*), *Acinetobacter* spp. (e.g., *Acinetobacter baumannii*) and *Stenotrophomonas* spp. (e.g., *Stenotrophomonas maltophilia*). At least a portion of these microorganisms would be appropriate for detection in a sepsis test.

In another particular aspect, the microorganisms belong to a fungal group of microorganisms selected from the group consisting of *Candida* spp. (e.g., *Candida albicans, Candida tropicalis, Candida glabrata, Candida parapsilosis, Candida lusitaniae, Candida krusei, Candida zeylanoides, Candida guilliermondi, Candida pseudotropicalis* and *Candida famata*), *Histoplama capsulatum, Cryptococcus* spp. (e.g., *Cryptococcus neoformans, Cryptococcus albidus* and *Cryptococcus laurentii*) *Coccidioides* spp. (e.g., *Coccidioides immitis*), *Trichosporon* spp. (e.g., *Trichosporon cutaneum*), *Malassezia* spp. (e.g., *Malassezia furfur*), *Rhodotorula* spp., *Nocardia* spp. (e.g., *Nocardia asteroides*), *Fusarium* spp. and *Asperigillus* spp. (e.g., *Asperigillus fumigatus*). At least a portion of these microorganisms would be appropriate for detection in a sepsis test.

According to another embodiment of the invention, there is provided reaction mixture for amplifying a target nucleic acid sequence, the reaction mixture comprising: a tagged oligonucleotide comprising first and second regions, the first region comprising a target hybridizing sequence hybridized to a 3'-end of a target nucleic acid sequence and the second region comprising a tag sequence situated 5' to the target hybridizing sequence; a first oligonucleotide comprising a hybridizing sequence which hybridizes to a 3'-end of the complement of the target nucleic acid sequence; and a second oligonucleotide comprising a hybridizing sequence which hybridizes to the complement of the tag sequence, where unhybridized tagged oligonucleotide in the reaction mixture has an inactive form which blocks or prevents the unhybridized tagged oligonucleotide from hybridizing to the target nucleic acid sequence.

In a more particular aspect according to this embodiment, the inactive form of the tagged oligonucleotide comprises a tag closing sequence hybridized to the target hybridizing sequence.

In another aspect, the tagged oligonucleotide and said tag closing sequence are distinct molecules, the tag closing sequence being a tag closing oligonucleotide.

In another aspect, the tagged oligonucleotide and the tag closing sequence are contained in the same molecule.

In yet another aspect, the tagged oligonucleotide is not attached to a solid support.

Certain other embodiments of the invention relate to the use of the methods described herein as a means for monitoring bioprocess samples, streams, and the like. In one embodiment, for example, there is provided a method for monitoring a bioprocess for the presence of contaminating nucleic acid comprising the steps of (a) treating a first bioprocess sample with a tagged oligonucleotide, wherein said tagged oligonucleotide comprises first and second regions, the first region comprising a target hybridizing sequence capable of hybridizing to a target nucleic acid sequence of an organism of interest and the second region comprising a tag sequence, situated 5' to said target hybridizing sequence, which does not stably hybridize to the target nucleic acid sequence; under conditions wherein the tagged oligonucleotide stably hybridizes to the target nucleic acid sequence present in said first sample; (b) removing or inactivating unhybridized tagged oligonucleotide from the first bioprocess sample; and (c) exposing a second bioprocess sample, the second bioprocess sample comprising the first bioprocess sample and further comprising additional bioprocess samples, to amplification reagents and conditions sufficient for amplification of the target nucleic acid sequence using: (i) a first oligonucleotide which hybridizes to a complement of the tag sequence and (ii) a second oligonucleotide sequence which hybridizes to a complement of the target nucleic acid sequence, where detectable amplification resulting from the first and second oligonucleotides is contributed by the target nucleic acid sequence of an organism of interest in the first bioprocess sample and not by the target nucleic acid sequence contributed by the additional bioprocess samples.

In another embodiment, the present invention provides a method for monitoring a bioprocess for the presence of contaminating nucleic acid comprising the steps of (a) treating a first bioprocess sample with a first tagged oligonucleotide, where the first tagged oligonucleotide comprises first and second regions, the first region comprising a target hybridizing sequence capable of hybridizing to a target nucleic acid sequence of an organism of interest and the second region comprising a first tag sequence, situated 5' to the target hybridizing sequence, which does not stably hybridize to the target nucleic acid sequence; under conditions where the first tagged oligonucleotide stably hybridizes to the target nucleic acid sequence present in said first sample; (b) treating a second bioprocess sample with a second tagged oligonucleotide, where the second tagged oligonucleotide comprises first and second regions, the first region comprising a target hybridizing sequence capable of hybridizing to the target nucleic acid sequence of the organism of interest and the second region comprising a second tag sequence, situated 5' to the target hybridizing sequence and different from the first tag sequence, which does not stably hybridize to the target nucleic acid sequence; under conditions where the second tagged oligonucleotide stably hybridizes to the target nucleic acid sequence present in the second sample; and (c) performing a nucleic acid amplification reaction on a third bioprocess sample, the third bioprocess sample comprising the first and the second bioprocess samples, using: (i) a first oligonucleotide which hybridizes to a complement of the first tag sequence; (ii) a second oligonucleotide sequence which hybridizes to a complement of the second tag sequence; and (iii) a third oligonucleotide which hybridizes to a complement of the target nucleic acid sequence; where the detection of amplification product resulting from the first and second oligonucleotides is indicative of the presence of the target nucleic acid sequence of the organism of interest in the first bioprocess sample, and where detection of amplification product resulting from the first and third oligonucleotides is indicative of the presence of the target nucleic acid sequence of the organism of interest in the second bioprocess sample.

In a further embodiment of the invention, a pre-amplification reaction mixture is provided for the selective amplification of one or more target nucleic acid sequences, where the reaction mixture comprises: a tagged oligonucleotide comprising first and second regions, said first region comprising a target hybridizing sequence hybridized to a target region contained at a 3'-end of one or more target nucleic acid sequences present in the reaction mixture and the second region comprises a tag sequence situated 5' to the target hybridizing sequence; a first oligonucleotide comprising a hybridizing sequence which hybridizes to a 3'-end of the complement of one or more of the target nucleic acid sequences; and a second oligonucleotide comprising a hybridizing sequence which hybridizes to the complement of the tag sequence, where the second oligonucleotide preferably does not stably hybridize to a target nucleic acid containing the target nucleic acid such that it can be enzymatically extended in the presence of a nucleic acid polymerase added to the reaction mixture to produce a primer extension product complementary to one or more of the target nucleic acid sequences, where the reaction mixture is substantially free of an active form of the tagged oligonucleotide which is not hybridized to the target region contained in the one or more target nucleic acid sequences present in the reaction mixture, where the active form of the tagged oligonucleotide has an available target hybridizing sequence for hybridization to the target region present in a non-target nucleic acid added to the reaction mixture, and where the reaction mixture does not include a nucleic acid polymerase capable of extending any of the oligonucleotides in a template-dependent manner. The "non-target" nucleic is from a source outside of the reaction mixture and may contain a sequence identical to that of the target nucleic acid sequence. The source of the non-target nucleic acid may be environmental or it may be a component or reagent added to the reaction mixture, such a nucleic acid polymerase. The tagged oligonucleotide can be a tagged priming oligonucleotide or a tagged promoter oligonucleotide having a promoter recognized by an RNA polymerase situated 5' to the second region.

In one aspect of this embodiment, the tagged priming oligonucleotide does not include a promoter for RNA polymerase, while the first oligonucleotide includes an RNA promoter situated 5' to the hybridizing sequence of the first oligonucleotide. In a preferred aspect, the first oligonucleotide further includes a blocking moiety situated at its 3'-terminus. In another aspect that is useful for amplifying an *E. coli* target sequence, the target hybridizing sequence of the tagged oligonucleotide consists of SEQ ID NO:19, its RNA equivalent or a complement thereof, and the first hybridizing sequence of the first oligonucleotide consists of SEQ ID NO:20, its RNA equivalent or a complement thereof.

In another aspect of this embodiment, the tagged oligonucleotide and the first oligonucleotide may each include a promoter for an RNA polymerase situated 5' to the tag sequence and the hybridizing sequence, respectively. In this aspect, the first oligonucleotide can include a blocking moiety situated at its 3'-terminus.

In yet another aspect of this embodiment, the tagged oligonucleotide includes a tag closing sequence joined to its 3'-end, thereby forming a unitary molecule referred to as a "tag molecule." Depending on the nature of the amplification reaction, the tag molecule may or may not include a promoter for an RNA polymerase situated 5' to the tag sequence. In one embodiment, tag molecules that have not hybridized to the target region of at least one target nucleic acid sequence remain "free" in the reaction mixture (i.e., the tag molecules do not form hybrid duplexes other than through self-hybridization). Self-hybridized tag molecules are referred to as "hairpin tag molecules," which is an inactive form of the tag molecule that prevents it from hybridizing to any complementary nucleic acids that are subsequently added to the reaction mixture, such as through a contaminated enzyme preparation or reagent containing non-target nucleic acids. In still another aspect of this embodiment, substantially all of the tag molecules in the reaction mixture are in a hybridized state (hybridized either to the target region of a target nucleic acid sequence or to themselves in the form of hairpin tag molecules). At least a portion of the tag molecules which have not hybridized to the target region of a target nucleic acid sequence (i.e., hairpin tag molecules) are removed from the reaction mixture by, for example, subjecting the reaction mixture to a target capture and washing procedure.

In a still further aspect of this embodiment, there are substantially no tagged oligonucleotides that exist in an unhybridized state when the reaction mixture is exposed to an enzyme preparation for amplifying the one or more target nucleic acid sequences. Thus, in this aspect, the reaction mixture is substantially depleted of unhybridized tagged oligonucleotides specific for the one or more target nucleic acid sequences provided by the sample of interest. This may be accomplished with, for example, a target capture and washing procedure that separates hybridized tagged oligonucleotides from unhybridized tagged oligonucleotides, and then selectively removes the unhybridized tagged oligonucleotides from the reaction mixture.

In yet another aspect of this embodiment, the tagged oligonucleotide does not include either a tag closing sequence or a tag closing oligonucleotide. Accordingly, in this aspect the tagged oligonucleotide cannot be characterized as being a "tag molecule."

In still another aspect of this embodiment, a probe is included for detecting an amplification product synthesized in an in vitro reaction that involves enzymatic extension of the tagged oligonucleotide and the second oligonucleotide. The amplification product includes copies of one or more of the target nucleic acid sequences and/or their complements.

In yet another embodiment, a reaction mixture is provided for the selective amplification of one or more target nucleic acid sequences, where the reaction mixture comprises: a tagged oligonucleotide comprising first and second regions, where the first region comprises a target hybridizing sequence hybridized to a 3'-end of a target nucleic acid sequence and the second region comprises a tag sequence situated 5' to the target hybridizing sequence; a first oligonucleotide comprising a hybridizing sequence which hybridizes to a 3'-end of the complement of the target nucleic acid sequence; and a second oligonucleotide comprising a hybridizing sequence which hybridizes to the complement of the tag sequence, where the second oligonucleotide preferably does not stably hybridize to a target nucleic acid containing the target nucleic acid such that it can be enzymatically extended in the presence of a nucleic acid polymerase added to or present in the reaction mixture to produce a primer extension product complementary to one or more of the target nucleic acid sequences, and where substantially all unhybridized tagged oligonucleotide in the reaction mixture has an inactive form which blocks or prevents said unhybridized tagged oligonucleotide from hybridizing to the target nucleic acid sequence.

The inactive form of the tagged oligonucleotide can comprise a tag closing sequence hybridized to the target hybridizing sequence. The tag closing sequence can be a distinct molecule when not hybridized to the target hybridizing sequence or it can be contained in a molecule including the tagged oligonucleotide, in which case the tag closing sequence is preferably joined to the 5'-end of the tagged oligonucleotide by a non-nucleotide linker (i.e., the constituents of the linker cannot be copied by a nucleic acid polymerase). The tagged oligonucleotide may or may not be joined to a solid support and is preferably not directly attached to solid support (e.g., particles or beads). If joined to a solid support, either directly or indirectly, the tagged oligonucleotide may further function as a capture probe for binding and immobilizing a target nucleic acid sequence.

The tagged oligonucleotides of the above reaction mixture embodiments may possess the characterizing features of any of the various tagged oligonucleotides embodiments described infra. And, unless specifically excluded, the reaction mixtures may further include the reagents and components needed to conduct an amplification reaction.

These and other features and advantages of the present invention will become apparent upon reference to the following detailed description, the attached drawings and the claims. All references disclosed herein are hereby incorporated by reference in their entirety as if each was incorporated individually.

DETAILED DESCRIPTION OF THE INVENTION

Figure 1:
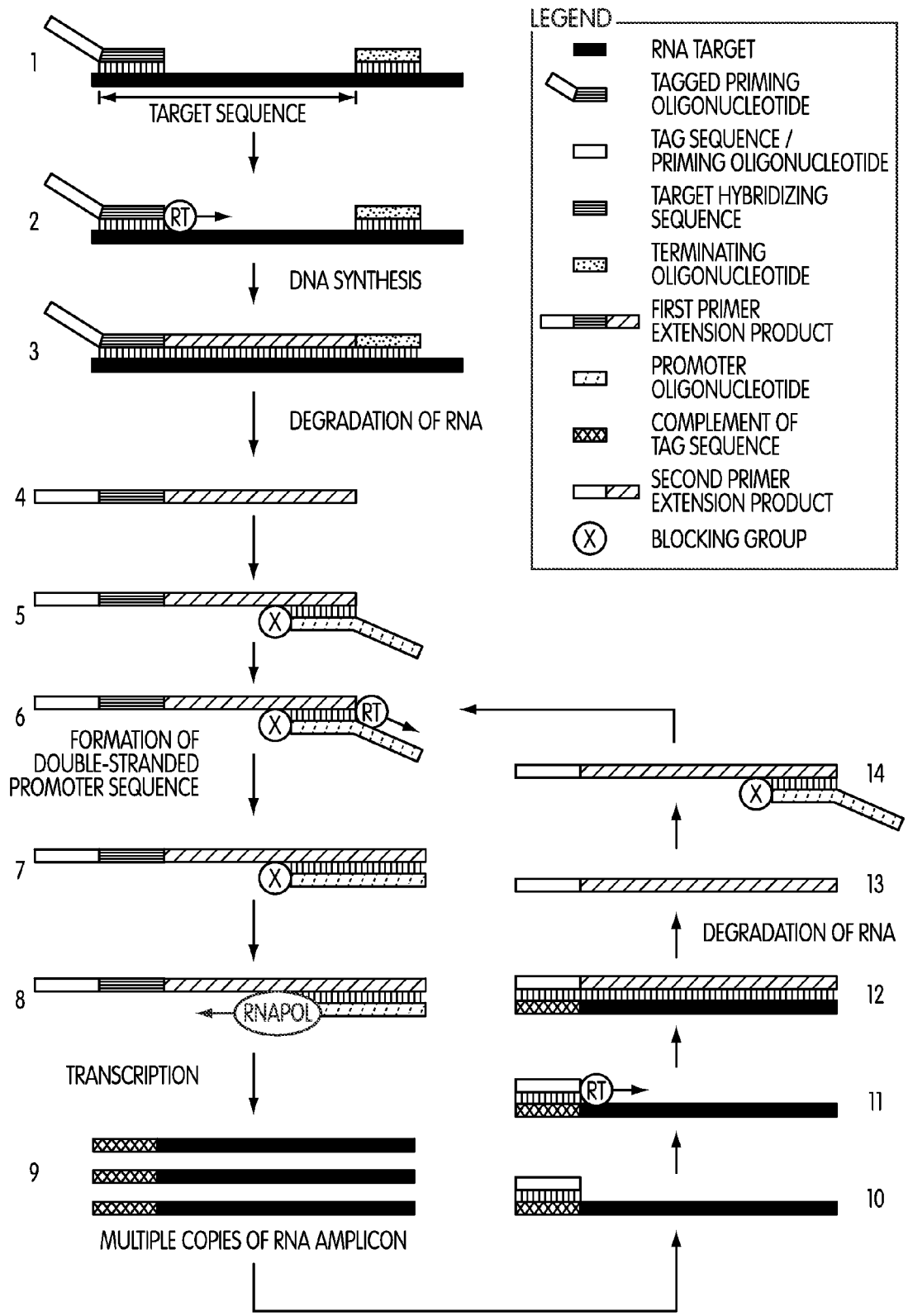
FIG. 1 illustrates the steps of a transcription-based amplification reaction initiated with a tagged priming oligonucleotide that hybridizes to a 3'-end of an RNA target sequence. A first extension product formed with the tagged priming oligonucleotide has a 3'-end which is determined by a terminating oligonucleotide hybridized adjacent to or near the 5'-end of the RNA target sequence. A blocked promoter oligonucleotide hybridizes to a 3'-end of the first extension product and is used to generate RNA transcripts that are cycled into the amplification reaction.
Figure 2:
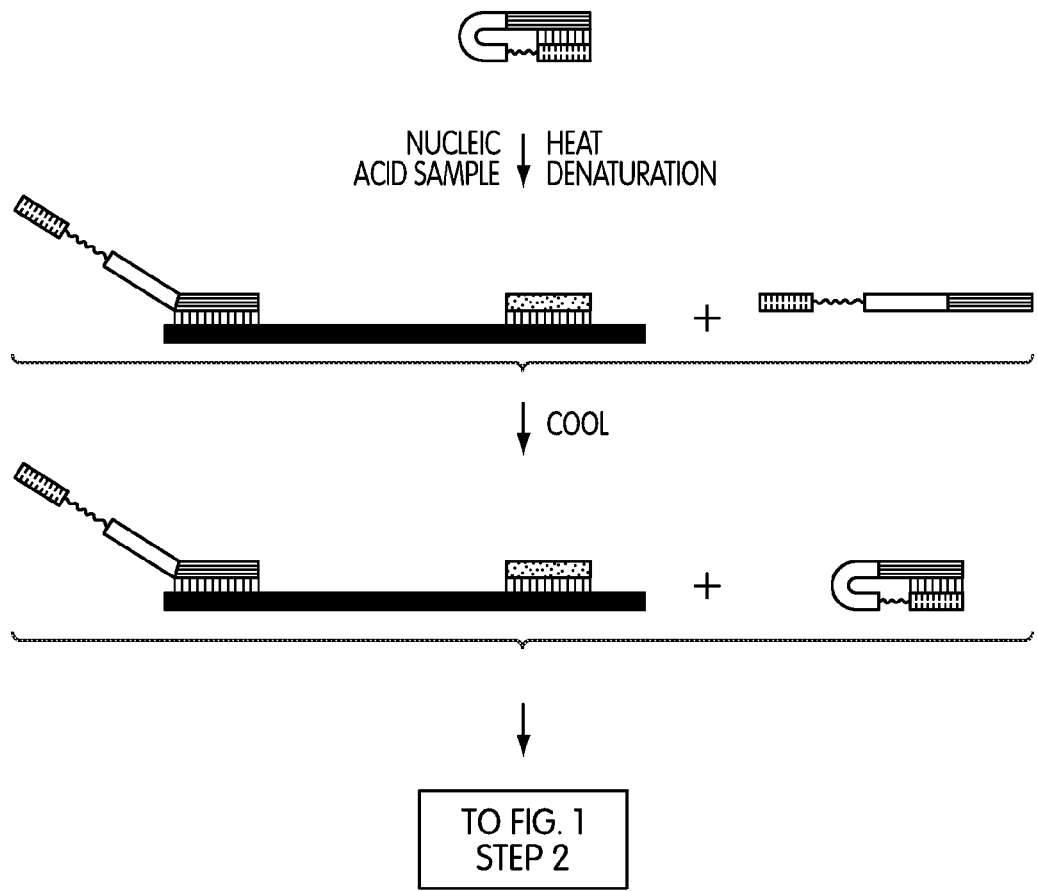
FIG. 2 illustrates the use of a hairpin tag molecule in the amplification reaction of FIG. 1.

In accordance with the present invention, nucleic acid amplification methods are provided that desirably reduce or eliminate false positive amplification signals resulting from contaminating biological material that may be present in a reagent or component of an amplification reaction. The provided methods also allow for less stringent purification and/or sterility efforts than have been conventionally needed in order to ensure that enzymes and other reagents or components used in amplification reactions, and the environment in which amplification reactions are performed, are free of contamination by microorganisms or components thereof, such as nucleic acid material, that may yield false positive results.

The practice of the present invention will employ, unless otherwise indicated, conventional techniques of molecular biology, recombinant DNA, and chemistry, which are within the skill of the art. Such techniques are explained fully in the literature. See, e.g., *Molecular Cloning A Laboratory Manual,* 2nd Ed., Sambrook et al., ed., Cold Spring Harbor Laboratory Press: (1989); *DNA Cloning,* Volumes I and II (D. N. Glover ed., 1985); *Oligonucleotide Synthesis* (M. J. Gait ed., 1984); Mullis et al., U.S. Pat. No. 4,683,195; *Nucleic Acid Hybridization* (B. D. Hames & S. J. Higgins eds. 1984); B. Perbal, *A Practical Guide To Molecular Cloning* (1984); the treatise, *Methods In Enzymology* (Academic Press, Inc., N.Y.); and in Ausubel et al., *Current Protocols in Molecular Biology,* John Wiley and Sons, Baltimore, Md. (1989).

Definitions

The following terms have the following meanings unless expressly stated to the contrary. It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

Nucleic Acid

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, viral genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid. The term "polynucleotide" may be used herein to denote a nucleic acid chain. Throughout this application, nucleic acids are designated as having a 5'-terminus and a 3'-terminus. Standard nucleic acids, e.g., DNA and RNA, are typically synthesized "3'-to-5'," i.e., by the addition of nucleotides to the 5'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" is a unit that does not significantly participate in hybridization of a polymer. Such units must not, for example, participate in any significant hydrogen bonding with a nucleotide, and would exclude units having as a component one of the five nucleotide bases or analogs thereof.

Target Nucleic Acid/Target Sequence

A "target nucleic acid" is a nucleic acid present in a nucleic acid sample comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include viral genomes, bacterial genomes, fungal genomes, plant genomes, animal genomes, rRNA, tRNA, or mRNA from viruses, bacteria or eukaryotic cells, mitochondrial DNA, or chromosomal DNA.

Target nucleic acids may be isolated from any number of sources based on the purpose of the amplification assay being carried out. Sources of target nucleic acids include, but are not limited to, clinical specimens (e.g., blood, either whole blood or platelets, urine, saliva, feces, semen, or spinal fluid), environmental samples (e.g., water or soil samples), food samples, beverages, industrial samples (e.g., products and process materials, including water), seed stocks, cDNA libraries, or total cellular RNA. By "isolated" it is meant that a sample containing a target nucleic acid is taken from its natural milieu; however, the term does not connote any particular degree of purification. If necessary, target nucleic acids of the present invention are made available for interaction with the various oligonucleotides of the present invention. This may include, for example, cell lysis or cell permeabilization to release the target nucleic acid from cells, which then may be followed by one or more purification steps, such as a series of isolation and wash steps. See, e.g., Clark et al., "Method for Extracting Nucleic Acids from a Wide Range of Organisms," U.S. Pat. No. 5,786,208; and Hogan, "Polynucleotide Matrix-Based Method of Identifying Microorganisms, U.S. Pat. No. 6,821,770. This may be particularly important where the sample source or cellular material released into the sample can interfere with the amplification reaction. Methods to prepare target nucleic acids from various sources for amplification are well known to those of ordinary skill in the art. Target nucleic acids of the present invention may be purified to some degree prior to the amplification reactions described herein, but in other cases, the sample is added to the amplification reaction without any further manipulations.

The term "target sequence" refers to the particular nucleotide sequence of the target nucleic acid which is to be amplified. The "target sequence" includes the complexing sequences to which oligonucleotides (e.g., tagged oligonucleotides, priming oligonucleotides and/or promoter oligonucleotides) complex during the processes of the present invention. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids. As will be understood by those of ordinary skill in the art, "unique" sequences are judged from the testing environment. At least the sequences recognized by the target hybridizing sequence of a tagged oligonucleotide and the associated detection probe or probes (as described in more detail elsewhere herein) should be unique in the environment being tested, but need not be unique within the universe of all possible sequences. Furthermore, even though the target sequence should contain a "unique" sequence for recognition by a tagged oligonucleotide or detection probe, it is not always the case that the priming oligonucleotide and/or promoter oligonucleotide are recognizing "unique" sequences. In some embodiments, it may be desirable to choose a target sequence which is common to a class of organisms, for example, a sequence which is common to all *E. coli* strains that might be in a sample. In other situations, a very highly specific target sequence, or a target sequence having at least a highly specific region recognized by the detection probe, would be chosen so as to distinguish between closely related organisms, for example, between pathogenic and non-pathogenic *E. coli*. A target sequence of the present invention may be of any practical length. A minimal target sequence includes a region which hybridizes to the target hybridizing sequence of a tagged oligonucleotide, the complement of a region which hybridizes to a priming oligonucleotide or the hybridizing region of a promoter oligonucleotide, and a region used for detection, e.g., a region (or complement thereof) which hybridizes to a detection probe, as described in more detail elsewhere herein. The region which hybridizes with the detection probe may overlap with or be contained within the region which hybridizes with the priming oligonucleotide (or its complement) or the hybridizing region of the promoter oligonucleotide (or its complement). In addition to the minimal requirements, the optimal length of a target sequence depends on a number of considerations, for example, the amount of secondary structure, or self-hybridizing regions in the sequence. Determining the optimal length is easily accomplished by those of ordinary skill in the art using routine optimization methods. Typically, target sequences of the present invention range from about 100 nucleotides in length to from about 150 to about 250 nucleotides in length. The optimal or preferred length may vary under different conditions, which can easily be tested by one of ordinary skill in the art according to the methods described herein. The terms "amplicon" refers to a nucleic acid molecule generated during an amplification procedure that is substantially complementary or identical to a sequence contained within the target sequence. The term "amplification product" refers to an amplicon or some other product indicative of an amplification reaction.

Oligonucleotides

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-ME) substitution to the ribofuranosyl moiety. See Becker et al., "Method for Amplifying Target Nucleic Acids Using Modified Primers," U.S. Pat. No. 6,130,038. Other sugar modifications include, but are not limited to 2'-amino, 2'-fluoro, (L)-alpha-threofuranosyl, and pentopuranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," U.S. Pat. No. 5,539,082.) Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). See Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

While design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

As used in this disclosure, the phrase "an oligonucleotide having a nucleic acid sequence 'comprising,' 'consisting of' or 'consisting essentially of' a sequence selected from" a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "an oligonucleotide substantially corresponding to a nucleic acid sequence" means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that "substantially corresponding" oligonucleotides of the invention can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

Tagged Oligonucleotide/Heterologous Tag Sequence

A "tagged oligonucleotide" as used herein refers to an oligonucleotide that comprises at least a first region and a second region, where the first region comprises a "target hybridizing sequence" which hybridizes to the 3'-end of a target nucleic acid sequence of interest, and where the second region comprises a "tag sequence" situated 5' to the target hybridizing sequence and which does not stably hybridize or bind to a target nucleic acid containing the target nucleic acid sequence. Hybridization of the target hybridizing sequence to the target nucleic acid sequence produces a "tagged target nucleic acid sequence." The features and design considerations for the target hybridizing sequence component would be the same as for the priming oligonucleotides discussed infra.

The "tag sequence" or "heterologous tag sequence" may be essentially any heterologous sequence provided that it does not stably hybridize to the target nucleic acid sequence of interest and, thereby, participate in detectable amplification. The tag sequence preferably does not stably hybridize to any sequence derived from the genome of an organism being tested or, more particularly, to any target nucleic acid under reaction conditions. A tag sequence that is present in a tagged oligonucleotide is preferably designed so as not to substantially impair or interfere with the ability of the target hybridizing sequence to hybridize to its target sequence. Moreover, the tag sequence will be of sufficient length and composition such that once a complement of the tag sequence has been incorporated into an initial DNA primer extension product, a tag-specific priming oligonucleotide can then be used to participate in subsequent rounds of amplification as described herein. A tag sequence of the present invention is typically at least 10 nucleotides in length, and may extend up to 15, 20, 25, 30, 35, 40, 50 or more nucleotides in length. Skilled artisans will recognize that the design of tag sequences and tagged oligonucleotides for use in the present invention can follow any of a number of suitable strategies, while still achieving the objectives and advantages described herein.

In certain embodiments, the tagged oligonucleotide is a "tagged priming oligonucleotide" comprising a tag sequence and a target hybridizing sequence. In other embodiments, the tagged oligonucleotide is a "tagged promoter oligonucleotide" comprising a tag sequence, a target hybridizing sequence and a promoter sequence situated 5' to the tag sequence and effective for initiating transcription therefrom.

Inactivating

The term "inactivating" means that a heterologous tag sequence is altered so that it does not stably bind to a target nucleic acid sequence under amplification conditions. In the case of an unhybridized tagged oligonucleotide, the term "inactivating" means that the tagged oligonucleotide is altered from an "active" confirmation which permits the target hybridizing sequence to hybridize to the target nucleic acid sequence to an "inactive" confirmation which blocks or otherwise prevents the target hybridizing sequence from hybridizing to the target nucleic acid sequence. For example, an inactive confirmation may be formed under stringency conditions permitting the tag closing sequence to form a stable hybrid with the target hybridizing sequence (e.g., under less stringent conditions than the conditions for forming an active confirmation of the tagged oligonucleotide). Unless further altered, the tag closing sequence:target hybridizing sequence hybrid remains closed under amplification conditions. Alternatively, a duplex formed between the tag closing sequence and the target hybridizing sequence may be altered by an enzyme, such as a DNAse, an S1 nuclease, an endonuclease, such as a restriction enzyme which cleaves a double-stranded restriction site formed between the tag closing sequence and the target hybridizing sequence, a ribonuclease activity (e.g., RNAse H activity) for digesting the RNA component (e.g., target hybridizing sequence) of a DNA:RNA hybrid, or an exonuclease having a 3'-to-5' or 5'-to-3' activity for removing nucleotides from the target hybridizing sequence hybridized to the tag closing sequence. However, to avoid exposing a sample to a potentially contaminating source of the target nucleic acid sequence, the use of enzymes to inactivate tagged oligonucleotides which have not hybridized to the target nucleic acid sequence is generally not preferred. Other inactivating means include chemicals for altering the target hybridizing sequence so that it is incapable of hybridizing to a target nucleic acid sequence under amplification conditions.

Moieties can be included in the tag hybridizing sequence to further stabilize hybrids formed between the target closing sequence and the target hybridizing sequence of tagged oligonucleotides, especially where it is anticipated that at least some of the inactive tagged oligonucleotides will be introduced into the amplification reaction mixture. Suitable moieties include modified nucleotides, including LNAs, 2'-O-ME ribonucleotides, 2,6 diamino purine. 5-methyl cytosine, and C-5 propynyl cytosine or uracil. Those skilled in the art will be able to readily select the number and positions of such modified nucleotides to limit breathing at the 5'- and 3'-ends of the tag closing sequence and to achieve a desired melting temperature of the hybrid without engaging undue experimentation. Other suitable moieties include minor groove binders and pendant groups, such as purine, DABCYL, pyrine and 5'-trimethoxy stilbene CAP.

Removing

As used herein, the term "removing" refers to the physical separation of tagged target nucleic acid sequences from unhybridized tagged oligonucleotides. Tagged target nucleic acid sequences can be physically separated from unhybridized tagged oligonucleotides (or heterologous tag sequences) present in a nucleic acid sample by a variety of techniques known to those skilled in the art. By way of example, tagged target nucleic acid sequences can be bound to a solid support and immobilized in a nucleic acid sample while unbound material is removed. To remove unbound material, the solid support can be subjected to one or more wash/rinse steps. The wash steps are intended to remove remaining unhybridized tagged oligonucleotides and potentially interfering cellular or sample material. A rinse step is typically included where the wash solution contains a component that is inhibitory to amplification when present at a sufficiently high concentration, such as a detergent. The solid support preferably binds specifically to target nucleic acids or tagged target nucleic acid sequences to prevent unhybridized tagged oligonucleotide (or unbound heterologous tag sequences) from entering into the amplification reaction. Exemplary means for capturing, immobilizing and purifying target nucleic acids are discussed below, an example of which is disclosed by Weisburg et al., "Two-Step Hybridization and Capture of a Polynucleotide," U.S. Pat. No. 6,534,273.

Tag Closing Sequence/Tag Closing Oligonucleotide

The phrases "tag closing sequence" and "tag closing oligonucleotide" refer to an oligonucleotide that is complementary to a portion of the target hybridizing sequence of a tagged oligonucleotide. The length and sequence of the tag closing sequence are selected so that the tag closing sequence does not stably hybridize to the target hybridizing sequence of the tagged oligonucleotide under a first set of conditions permitting stable hybridization of the target hybridizing sequence to a target sequence. The tag closing sequence may include abasic nucleotides or base mismatches with the target hybridizing sequence. Provided the tagged oligonucleotide is not hybridized to the target sequence, the tag closing sequence stably hybridizes to the target hybridizing sequence under a second set of less stringent conditions, thus "inactivating" or blocking the tagged oligonucleotide from hybridizing to the target sequence. The tag closing sequence may be in the form of a discrete oligonucleotide or it may be joined to the 5'-end of a tagged oligonucleotide ("tag molecule"), so that it forms a hairpin structure with the tagged oligonucleotide under the second set of conditions ("hairpin tag molecule"). If part of a tag molecule, the tag closing sequence is preferably joined to the tagged oligonucleotide via a non-nucleotide linker region (e.g., abasic nucleotides or polyethylene glycol) of sufficient length for the tag closing sequence to hybridize to the target hybridizing sequence under the second set of conditions. The tag closing sequence may be modified to prevent the initiation of DNA synthesis therefrom, which can include a blocking moiety situated at its 3'-terminus. The tag closing sequence is at least 3 but no more than about 20 bases in length. Typical tag closing sequences are from 10 to 16 bases in length.

Amplification or Nucleic Acid Amplification

By "amplification" or "nucleic acid amplification" is meant production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (Mullis et al., U.S. Pat. No. 4,683,195; Mullis, U.S. Pat. No. 4,683,202; and Mullis et al., U.S. Pat. No. 4,800,159), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (Gelfand et al., "Reverse Transcription with Thermostable DNA Polymerases—High Temperature Reverse Transcription," U.S. Pat. Nos. 5,322,770 and 5,310,652). Another method is strand displacement amplification (Walker, G. et al. (1992), *Proc. Natl. Acad. Sci. USA* 89, 392-396; Walker et al., "Nucleic Acid Target Generation," U.S. Pat. No. 5,270,184; Walker, "Strand Displacement Amplification," U.S. Pat. No. 5,455,166; and Walker et al. (1992) *Nucleic Acids Research* 20, 1691-1696), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (Malek et al., U.S. Pat. No. 5,130,238), commonly referred to as NASBA; one that uses an RNA replicase to amplify the probe molecule itself (Lizardi, P. et al. (1988) *BioTechnol.* 6, 1197-1202), commonly referred to as Qβ replicase; a transcription-based amplification method (Kwoh, D. et al. (1989) *Proc. Natl. Acad. Sci. USA* 86, 1173-1177); self-sustained sequence replication (Guatelli, J. et al. (1990) *Proc. Natl. Acad. Sci. USA* 87, 1874-1878; Landgren (1993) *Trends in Genetics* 9, 199-202; and Lee, H. et al., NUCLEIC ACID AMPLIFICATION TECHNOLOGIES (1997)); and, transcription-mediated amplification (Kacian et al., "Nucleic Acid Sequence Amplification Methods," U.S. Pat. No. 5,480,784; and Kacian et al., U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.). Other illustrative amplification methods suitable for use in accordance with the present invention include rolling circle amplification (RCA) (Lizardi, "Rolling Circle Replication Reporter Systems," U.S. Pat. No. 5,854,033); Helicase Dependent Amplification (HDA) (Kong et al., "Helicase Dependent Amplification Nucleic Acids," U.S. Pat. Appln. Pub. No. US 2004-0058378 A1); and Loop-Mediated Isothermal Amplification (LAMP) (Notomi et al., "Process for Synthesizing Nucleic Acid," U.S. Pat. No. 6,410,278).

Preferred transcription-based amplification systems of the present invention include TMA, which employs an RNA polymerase to produce multiple RNA transcripts of a target region (e.g., Kacian et al., U.S. Pat. Nos. 5,480,784 and 5,399,491; and Becker et al., "Single-Primer Nucleic Acid Amplification Methods," U.S. Pat. Appln. Pub. No. US 2006-0046265 A1). TMA uses a "promoter oligonucleotide" or "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA:DNA hybrid, thereby making the DNA strand available for hybridization with a primer or promoter-primer. Generally, the RNAse H activity associated with the reverse transcriptase provided for amplification is used.

In one illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNAse H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNAse H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

In another illustrative TMA method, one or more features as described in Becker et al., U.S. Pat. Appln. Pub. No. US 2006-0046265 A1 are optionally incorporated. Preferred TMA methods in this respect include the use of blocking moieties, terminating moieties, and other modifying moieties that provide improved TMA process sensitivity and accuracy. Thus, certain preferred embodiments of the present invention employ tagged oligonucleotides, as described herein, in conjunction with the methods as described in Becker et al., U.S. Pat. Appln. Pub. No. US 2006-0046265 A1.

By "detectable amplification" is meant that a detectable signal associated with an amplification product in an amplification reaction mixture rises above a predetermined background or threshold level (end-point amplification) or rises above a background or threshold level within a predetermined period of time (real-time amplification). See, e.g., Light et al., "Method for Determining the Amount of an Analyte in a Sample," U.S. Pat. Appln. Pub. No. US 2006-0276972, paragraphs 506-549. The amplification product contains a sequence having sequence identity with a target nucleic acid sequence or its complement and can be detected with, for example, an intercalating dye or a detection probe having specificity for a region of the target nucleic acid sequence or its complement.

"Selective Amplification"

"Selective amplification" as used herein, refers to the amplification of a target nucleic acid sequence according to the present invention where detectable amplification of the target sequence is limited or substantially limited to amplification of target sequence contributed by sample of interest that is being tested and is not contributed by target nucleic acid sequence contributed by some other sample source, e.g., contamination present in reagents or components used during amplification reactions or in the environment or environmental conditions in which amplification reactions are performed.

Amplification Conditions

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention hybridize under stringent hybridization conditions. While the Examples section infra provides preferred amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS ($11^{th}$ ed. 1992).)

"Stringent hybridization conditions" or "stringent conditions" refer to conditions where a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

By "nucleic acid hybrid" or "hybrid" or "duplex" is meant a nucleic acid structure containing a double-stranded, hydrogen-bonded region where each strand is complementary to the other, and where the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable, double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "preferentially hybridize" is meant that under stringent hybridization conditions, certain complementary nucleotides or nucleobase sequences hybridize to form a stable hybrid preferentially over other, less stable duplexes. By "does not stably hybridize" is meant that a stable hybrid is not formed in appreciable and/or detectable amounts under a defined set of conditions.

By "stable" or "stably hybridize" is meant that the temperature of a reaction mixture is at least 2° C. below the melting temperature of a nucleic acid duplex.

Promoter Oligonucleotide/Promoter Sequence

As is well known in the art, a "promoter" is a specific nucleic acid sequence that is recognized by a DNA-dependent RNA polymerase ("transcriptase") as a signal to bind to the nucleic acid and begin the transcription of RNA at a specific site. For binding, it was generally thought that such transcriptases required DNA which had been rendered double-stranded in the region comprising the promoter sequence via an extension reaction, however, the present inventors have determined that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

According to the present invention, a "promoter oligonucleotide" refers to an oligonucleotide comprising first and second regions, and which is preferably modified to prevent the initiation of DNA synthesis from its 3'-terminus. The "first region" of a promoter oligonucleotide of the present invention comprises a base sequence which hybridizes to a DNA template, where the hybridizing sequence is situated 3', but not necessarily adjacent to, a promoter region. The hybridizing portion of a promoter oligonucleotide of the present invention is typically at least 10 nucleotides in length, and may extend up to 15, 20, 25, 30, 35, 40, 50 or more nucleotides in length. The "second region" comprises a promoter for an RNA polymerase. A promoter oligonucleotide of the present invention is engineered so that it is incapable of being extended by an RNA- or DNA-dependent DNA polymerase, e.g., reverse transcriptase, preferably comprising a blocking moiety at its 3'-terminus as described above. Suitable and preferred promoter oligonucleotides are described herein.

Universal/Pan Oligonucleotides

"Universal" oligonucleotides or "pan" oligonucleotides include oligonucleotides that can be used in an amplification reaction to identify the presence of nucleic acid sequences of a class of organisms based upon highly conserved sequences that are unique to a class of organisms. (As used herein, the term "class" does not necessarily imply a recognized phylogenetic grouping or organisms.) For example, the highly conserved 16S ribosomal RNA-coding sequences contain regions that are found in bacteria, or groupings of bacteria (e.g., Eubacteria, Gram-positive bacteria or Gram-negative bacteria), but are not in humans and other higher organisms, and thus oligonucleotides may be designed and used in a nucleic acid amplification reaction to detect the presence of bacterial sequences in a sample of interest. See, e.g., McCabe et al. (1999) *Molecular Genetics and Metabolism* 66, 205-211; Schmidt, T. et al. (1994) *Meth. Enzymol.* 235, 205-222 (method for identifying pathogens); Kunishima, S. et al., (2000) *Transfusion* 40, 1420 (method for detecting bacteria in blood); Greisen, K. (1994) *J. Clin. Microbiol.* 32, 335-351 (method for detecting pathogenic bacteria in cerebral spinal fluid); Jordan, J. (2005) *J. Mol. Diag.* 7, 575-581 (method for diagnosing sepsis in neonates); Rothman, R. et al. (2002) *J. Infect. Dis.* 186, 1677-1681 (method for diagnosing acute bacterial endocarditis); and Cox, C. et al. (2002) *Arthritis Res. Ther.* 5, R1-R8 (detecting bacteria in synovial fluid). Similarly, universal oligonucleotides for other classes of organisms, such as fungal pathogens, have been described. See, e.g., Maaroati, Y. et al. (2003) *J. Clin. Microbiol.* 41, 3293-3298 (method for quantifying *Candida albicans* in blood); Carr, M. et al. (2005) *J. Clin. Microbiol.* 43, 3023-3026 (method for detecting *Candida dubliniensis* in blood); and White, P. et al. (2003) *J. Med. Microbiol.* 52, 229-238 (method for detecting systemic fungal infections). Essentially any universal oligonucleotides known or developed for a given class of organism may be advantageously employed in the methods described herein.

Priming Oligonucleotide

A priming oligonucleotide is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. A priming oligonucleotide is extended by the addition of covalently bonded nucleotide bases to its 3'-terminus, which bases are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

Displacer Oligonucleotide

A "displacer oligonucleotide" is a priming oligonucleotide which hybridizes to a template nucleic acid upstream from a neighboring priming oligonucleotide hybridized to the 3'-end of a target sequence (referred to herein as the "forward priming oligonucleotide"). By "upstream" is meant that a 3'-end of the displacer oligonucleotide complexes with the template nucleic acid 5' to a 3'-end of the forward priming oligonucleotide. When hybridized to the template nucleic acid, the 3'-terminal base of the displacer oligonucleotide is preferably adjacent to or spaced from the 5-terminal base of the forward priming oligonucleotide. More preferably, the 3'-terminal base of the displacer oligonucleotide is spaced from 5 to 35 bases from the 5'-terminal base of the forward priming oligonucleotide. The displacer oligonucleotide may be provided to a reaction mixture contemporaneously with the forward priming oligonucleotide or after the forward priming oligonucleotide has had sufficient time to hybridize to the template nucleic acid. Extension of the forward priming oligonucleotide can be initiated prior to or after the displacer oligonucleotide is provided to a reaction mixture. Under amplification conditions, the displacer oligonucleotide is extended in a template-dependent manner, thereby displacing a primer extension product comprising the forward priming oligonucleotide which is complexed with the template nucleic acid. Once displaced from the template nucleic acid, the primer extension product comprising the forward priming oligonucleotide is available for complexing with a promoter oligonucleotide. The forward priming oligonucleotide and the displacer oligonucleotide both preferentially hybridize to the target nucleic acid. Examples of displacer oligonucleotides and their uses are disclosed by Becker et al., "Methods and Kits for Amplifying DNA," U.S. Pat. No. 7,713,697, which enjoys common ownership herewith.

Blocking Moiety

As used herein, a "blocking moiety" is a substance used to "block" the 3'-terminus of an oligonucleotide or other nucleic acid so that it cannot be efficiently extended by a nucleic acid polymerase. A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., "Non-Nucleotide Linking Reagents for Nucleotide Probes," U.S. Pat. No. 6,031,091), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

Binding Molecule

As used herein, a "binding molecule" is a substance which hybridizes to or otherwise binds to an RNA target nucleic acid adjacent to or near the 5'-end of the desired target sequence, so as to limit a DNA primer extension product to a desired length, i.e., a primer extension product having a generally defined 3'-end. As used herein, the phrase "defined 3'-end" means that the 3'-end of a primer extension product is not wholly indeterminate, as would be the case in a primer extension reaction which occurs in the absence of a binding molecule, but rather that the 3'-end of the primer extension product is generally known to within a small range of bases. In certain embodiments, a binding molecule comprises a base region. The base region may be DNA, RNA, a DNA:RNA chimeric molecule, or an analog thereof. Binding molecules comprising a base region may be modified in one or more ways, as described herein. Exemplary base regions include terminating and digestion oligonucleotides, as described below. In other embodiments, a binding molecule may comprise, for example, a protein or drug capable of binding RNA with sufficient affinity and specificity to limit a DNA primer extension product to a pre-determined length.

Terminating Oligonucleotide

In the present invention, a "terminating oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. See, e.g., Majlessi et al. (1988) *Nucleic Acids Res.* 26, 2224-9. Other modifications as described elsewhere herein may be utilized in addition to or in place of 2'-O-ME ribonucleotides. For example, a terminating oligonucleotide may comprise PNA or an LNA. See, e.g., Petersen et al. (2000) *J. Mol. Recognit.* 13, 44-53. A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. Suitable and preferred terminating oligonucleotides are described herein. It should be noted that while a terminating oligonucleotide typically or necessarily includes a 3'-blocking moiety, "3'-blocked" oligonucleotides are not necessarily terminating oligonucleotides. Other oligonucleotides of the present invention, e.g., promoter oligonucleotides and capping oligonucleotides are typically or necessarily 3'-blocked as well.

Insertion Sequence

As used herein, an "insertion sequence" is a sequence positioned between the first region (i.e., template binding portion) and the second region of a promoter oligonucleotide. Insertion sequences are preferably 5 to 20 nucleotides in length, more preferably 6 to 18 nucleotides in length, and most preferably 6 to 12 nucleotides in length. The inclusion of insertion sequences in promoter oligonucleotides increases the rate at which RNA amplification products are formed. Exemplary insertion sequences are described herein.

Target Capture

Target capture, as used herein, includes any technique effective to remove all or substantially all unhybridized tagged oligonucleotide after hybridization of tagged oligonucleotide with a target nucleic acid sequence but prior to amplification of the target nucleic acid sequence. Generally, target capture involves capturing a target polynucleotide onto a solid support, such as magnetically attractable particles, where the solid support retains the target polynucleotide during one or more washing steps of the target polynucleotide purification procedure. In this way, a target polynucleotide is substantially purified from unhybridized tagged oligonucleotide prior to a subsequent nucleic acid amplification step. Numerous target capture methods are known and suitable for use in conjunction with the methods described herein.

For example, one illustrative approach described in U.S. Pat. Appln. Pub. No. US 2006-0068417 A1 uses at least one capture probe oligonucleotide that contains a target-complementary region and a member of a specific binding pair that joins a target nucleic acid to an immobilized probe on a capture support, thus forming a capture hybrid that is separated from other sample components of a sample. In another illustrative method, Weisburg et al., in U.S. Pat. No. 6,110,678, describe a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide.

Another illustrative target capture technique involves a hybridization sandwich technique for capturing and for detecting the presence of a target polynucleotide. See Ranki et al., "Detection of Microbial Nucleic Acids By a One-Step Sandwich Hybridization Test," U.S. Pat. No. 4,486,539. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Another illustrative target capture technique involves a method that uses a mediator polynucleotide that hybridizes to both a target polynucleotide and to a polynucleotide fixed on a solid support. See Stabinsky, "Methods and Kits for Performing Nucleic Acid Hybridization Assays," U.S. Pat. No. 4,751,177. The mediator polynucleotide joins the target polynucleotide to the solid support to produce a bound target. A labeled probe can be hybridized to the bound target and unbound labeled pro can be washed away from the solid support.

Yet another illustrative target capture technique is disclosed by Englelhardt, "Capture Sandwich Hybridization Method and Composition," U.S. Pat. No. 5,288,609, which describes a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, methods and kits for detecting nucleic acids use oligonucleotide primers labeled with specific binding partners to immobilize primers and primer extension products. See Burdick et al., "Diagnostic Kit and Method Using a Solid Phase Capture Means for Detecting Nucleic Acids," European Pat. Appln. No. 0 370 694 A2. The label specifically complexes with its receptor which is bound to a solid support.

The above capture techniques are illustrative only, and not limiting. Indeed, essentially any technique available to the skilled artisan may be used provided it is effective for removing all or substantially all unhybridized tagged oligonucleotide after hybridization of tagged oligonucleotide with a target nucleic acid sequence but prior to amplification of the target nucleic acid sequence, as described herein.

Probe

By "probe" or "detection probe" is meant a molecule comprising an oligonucleotide having a base sequence partly or completely complementary to a region of a target sequence sought to be detected, so as to hybridize thereto under stringent hybridization conditions. As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent).

The probes of this invention may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Probes may also include interacting labels which emit different signals, depending on whether the probes have hybridized to target sequences. Examples of interacting labels include enzyme/substrates, enzyme/cofactor, luminescent/quencher, luminescent/adduct, dye dimers, and Förrester energy transfer pairs. Certain probes of the present invention do not include a label. For example, non-labeled "capture" probes may be used to enrich for target sequences or replicates thereof, which may then be detected by a second "detection" probe. See, e.g., Weisburg et al., U.S. Pat. No. 6,534,273. While detection probes are typically labeled, certain detection technologies do not require that the probe be labeled. See, e.g., Nygren et al., "Devices and Methods for Optical Detection of Nucleic Acid Hybridization," U.S. Pat. No. 6,060,237.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "preferentially hybridize" is meant that under stringent hybridization conditions, probes of the present invention hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 18 to 35 bases in length.

Nucleic Acid "Identity"

In certain embodiments, a nucleic acid of the present invention comprises a contiguous base region that is at least 80%, 90%, or 100% identical to a contiguous base region of a reference nucleic acid. For short nucleic acids, e.g., certain oligonucleotides of the present invention, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA:RNA, RNA:DNA, or any combinations or analogs thereof. Equivalent RNA and DNA base sequences can be compared by converting U's (in RNA) to T's (in DNA).

Template

A "template" is a nucleic acid molecule that is being copied by a nucleic acid polymerase. A template may be single-stranded, double-stranded or partially double-stranded, depending on the polymerase. The synthesized copy is complementary to the template or to at least one strand of a double-stranded or partially double-stranded template. Both RNA and DNA are typically synthesized in the 5'-to-3' direction and the two strands of a nucleic acid duplex are aligned so that the 5'-termini of the two strands are at opposite ends of the duplex (and, by necessity, so then are the 3'-termini). While according to the present invention, a "target sequence" is always a "template," templates can also include secondary primer extension products and amplification products.

DNA-dependent DNA Polymerase

A "DNA-dependent DNA polymerase" is an enzyme that synthesizes a complementary DNA copy from a DNA template. Examples are Taq DNA polymerase, a highly thermostable DNA polymerase from the thermophilic bacterium *Therms aquaticus*, for PCR amplification reactions, DNA polymerase I from *E. coli*, bacteriophage T7 DNA polymerase, or DNA polymerases from bacteriophages T4, Phi-29, M2, or T5. DNA-dependent DNA polymerases of the present invention may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described below) typically also have DNA-dependent DNA polymerase activity. An example of such a polymerase is the MasterAmp™ Tth DNA Polymerase, which has both DNA-dependent and RNA-dependent (i.e., reverse transcriptase) DNA polymerase activities that can be used in both PCR and RT-PCR amplification reactions (Epicentre Biotechnologies, Madison, Wis.).

DNA-dependent RNA Polymerase (Transcriptase)

A "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

RNA-dependent DNA Polymerase (Reverse Transcriptase)

An "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. Preferred is reverse transcriptase derived from Maloney murine leukemia virus (MMLV-RT). A primer is required to initiate synthesis with both RNA and DNA templates.

Selective RNAses

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes other than RNAse H which possess the same or similar activity are also contemplated in the present invention. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes which selectively degrade RNA target sequences or RNA products of the present invention will be readily apparent to those of ordinary skill in the art.

Sense/Antisense Strand(s)

Discussions of nucleic acid synthesis are greatly simplified and clarified by adopting terms to name the two complementary strands of a nucleic acid duplex. Traditionally, the strand encoding the sequences used to produce proteins or structural RNAs are designated as the "sense (+)" strand and its complement the "antisense (−)" strand. It is now known that in many cases, both strands are functional, and the assignment of the designation "sense" to one and "antisense" to the other must then be arbitrary. Nevertheless, the terms are very useful for designating the sequence orientation of nucleic acids and will be employed herein for that purpose.

Specificity of the System

The term "specificity," in the context of an amplification system, is used herein to refer to the characteristic of an amplification system which describes its ability to distinguish between target and non-target sequences dependent on sequence and assay conditions. In terms of a nucleic acid amplification, specificity generally refers to the ratio of the number of specific amplicons produced to the number of side-products (i.e., the signal-to-noise ratio), described in more detail below.

Sensitivity

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, i.e., the ratio of specific amplicons to side-products.

Bioprocess

A "bioprocess," as used herein, refers generally to any process in which living cells, or components thereof, are present, either intended or unintended. For example, essentially any manufacturing or other process that employs one or more samples or sample streams, at least one of which comprises living cells, or components thereof, or may comprise such cells or components as a result of unintended contamination, is considered a bioprocess. In many such processes it is desirable to have the ability to detect, identify and/or control the presence and/or sources of living cells or components thereof within a process. Using the methods of the present invention, for example, the presence and/or sources of contaminating microorganisms or other biological material or components thereof in one or more bioprocess samples or streams may be monitored. In addition, the purification/sterilization requirements within certain samples/streams of a bioprocess may be advantageously reduced using the methods of the invention as set forth herein.

As discussed above, the present invention is directed generally to nucleic acid amplification methods that desirably reduce or eliminate false positive amplification signals resulting from contaminating biological material, such as nucleic acid material, that may be present in one or more reagents, samples or components that are used in an amplification reaction, or that may be present in the environment in which amplification reactions are performed. The invention further offers the advantage of requiring less stringent purification and/or sterility efforts conventionally needed in order to ensure that enzymes and other reagents used in amplification reactions, and the environment in which amplification reactions are performed, are free of bacterial and other nucleic acid contamination that may yield false positive results. Accordingly, the methods of the invention are particularly useful in detecting, monitoring and/or quantitating microorganisms (or contaminating nucleic acids from other sources) in clinical samples, bioprocess samples or sample streams, foodstuffs, water, industrial and environmental samples, seed stocks, and other types of material where the presence of microorganisms or other forms of contamination may need to be detected and/or monitored.

The present invention can be adapted for use in essentially any amplification procedure requiring a template-binding priming oligonucleotide capable of extension in the presence of nucleic acid polymerase. Incorporation of the tagged oligonucleotides (or heterologous tag sequences) into such primer-dependent amplification procedures can be accomplished without substantially modifying the reagents and reaction conditions of such procedures. Any needed modifications should be minor and would be well within the knowledge and capabilities of a skilled molecular biologist. Descriptions of various illustrative amplification procedures adopting tagged oligonucleotides follows.

FIG. 1 illustrates an adaptation of an isothermal, transcription-based amplification reaction known as reverse transcription-mediated amplification (rTMA), various aspects of which are disclosed in Becker et al., U.S. Pat. No. 7,374,885. The reaction of this illustrative embodiment is initiated by treating an RNA target sequence in a nucleic acid sample with both a tagged priming oligonucleotide and a terminating oligonucleotide. The tagged priming oligonucleotide includes a target hybridizing sequence that hybridizes to a 3'-end of the target sequence and a tag sequence situated 5' to the target hybridizing sequence. The terminating oligonucleotide hybridizes to a target nucleic acid containing the target sequence in the vicinity of the 5'-end of the target sequence. The terminating oligonucleotide is used to end primer extension of a nascent nucleic acid that includes the tagged priming oligonucleotide. Thus, the target nucleic acid forms a stable complex with the tagged priming oligonucleotide at the 3'-end of the target sequence and the terminating oligonucleotide located adjacent to or near the 5'-end of the target sequence prior to initiating a primer extension reaction. See FIG. 1, Step 1. Unhybridized tagged priming oligonucleotide is made unavailable for hybridization to the target sequence prior to initiating a primer extension reaction with the tagged priming oligonucleotide, preferably by inactivating and/or removing the unhybridized tagged priming oligonucleotide from the nucleic acid sample.

An extension reaction is then initiated from the 3'-end of the tagged priming oligonucleotide with a DNA polymerase, e.g., reverse transcriptase, to produce a first DNA primer extension product that includes the tag sequence and a region complementary to the target sequence. See FIG. 1, Steps 2 and 3. The first DNA primer extension product is then separated from the target sequence using an enzyme that selectively degrades the target sequence (e.g., RNAse H activity). See FIG. 1, Step 4.

Next, the first DNA primer extension product is treated with a promoter oligonucleotide having a hybridizing sequence and a promoter for an RNA polymerase situated 5' to the hybridizing sequence. The hybridizing sequence hybridizes to a region of the first DNA primer extension product that is complementary to the 3'-end of the target sequence, thereby forming a promoter oligonucleotide:first DNA primer extension product hybrid. In the illustrated reaction, the promoter oligonucleotide is modified to prevent the initiation of DNA synthesis, preferably by situating a blocking moiety at the 3'-end of the promoter oligonucleotide (e.g., nucleotide sequence having a 3'-to-5' orientation). See FIG. 1, Step 5. The 3'-end of the first DNA primer extension product is preferably extended to add a sequence complementary to the promoter, resulting in the formation of a double-stranded promoter sequence. See FIG. 1, Steps 6 and 7. Multiple copies of a first RNA product complementary to at least a portion of the first DNA primer extension product, not including the promoter portion, are then transcribed using an RNA polymerase which recognizes the double-stranded promoter and initiates transcription therefrom. See FIG. 1, Steps 8 and 9. As a result, the base sequence of the first RNA product is substantially identical to the base sequence of the target sequence and the complement of the tag sequence.

The first RNA products are treated with a priming oligonucleotide which hybridizes to the complement of the tag sequence to form a priming oligonucleotide:first RNA product hybrid, and the 3'-end of the priming oligonucleotide is extended with the DNA polymerase to produce a second DNA primer extension product complementary to the first RNA product. See FIG. 1, Steps 10-12. The second DNA primer extension product is then separated from the first RNA product using an enzyme that selectively degrades the first RNA product (e.g., RNAse H activity). See FIG. 1, Step 13.

The second DNA primer extension product is treated with the promoter oligonucleotide, which hybridizes to the 3'-end of the second DNA primer extension product to form a promoter oligonucleotide:second DNA primer extension product hybrid. See FIG. 1, Step 14. The promoter oligonucleotide:second DNA primer extension product hybrid then re-enters the amplification cycle at Step 6 of FIG. 1, where transcription is initiated from the double-stranded promoter and the cycle continues.

Figure 3A:
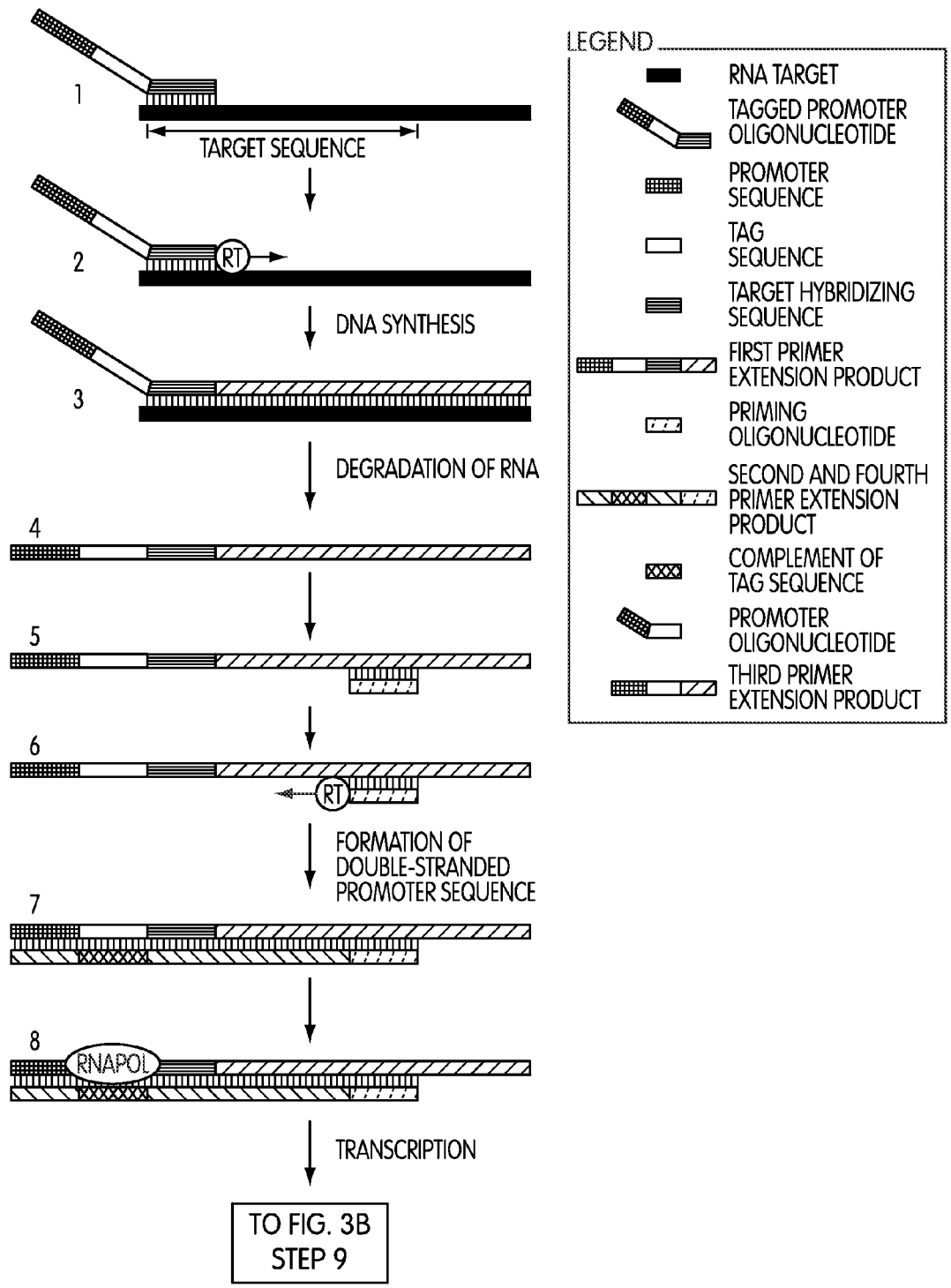
FIGS. 3A and 3B illustrate the steps of a transcription-mediated amplification reaction initiated with a tagged promoter oligonucleotide that hybridizes to a 3'-end of an RNA target sequence.
Figure 3B:
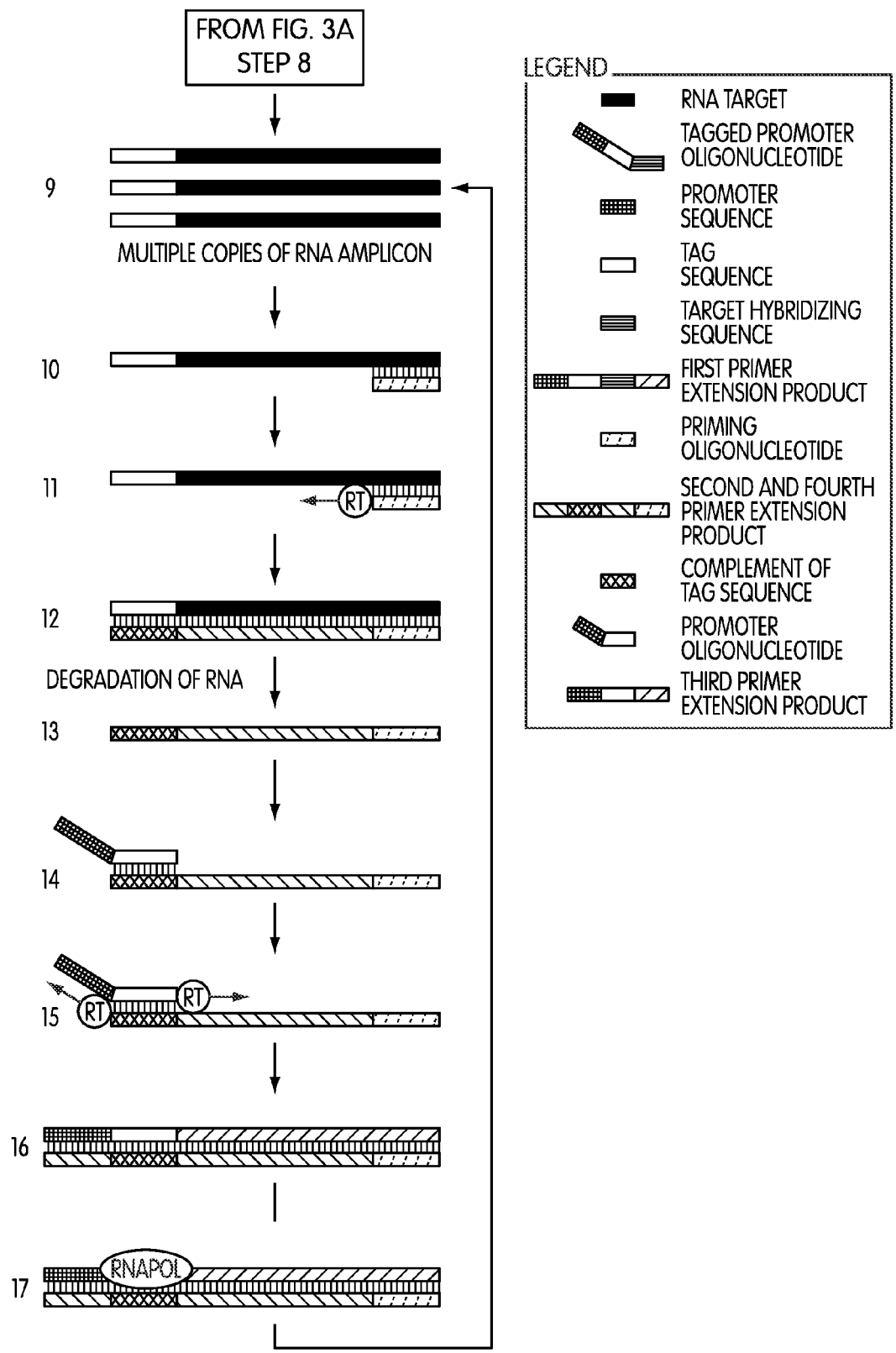
Figure 4:
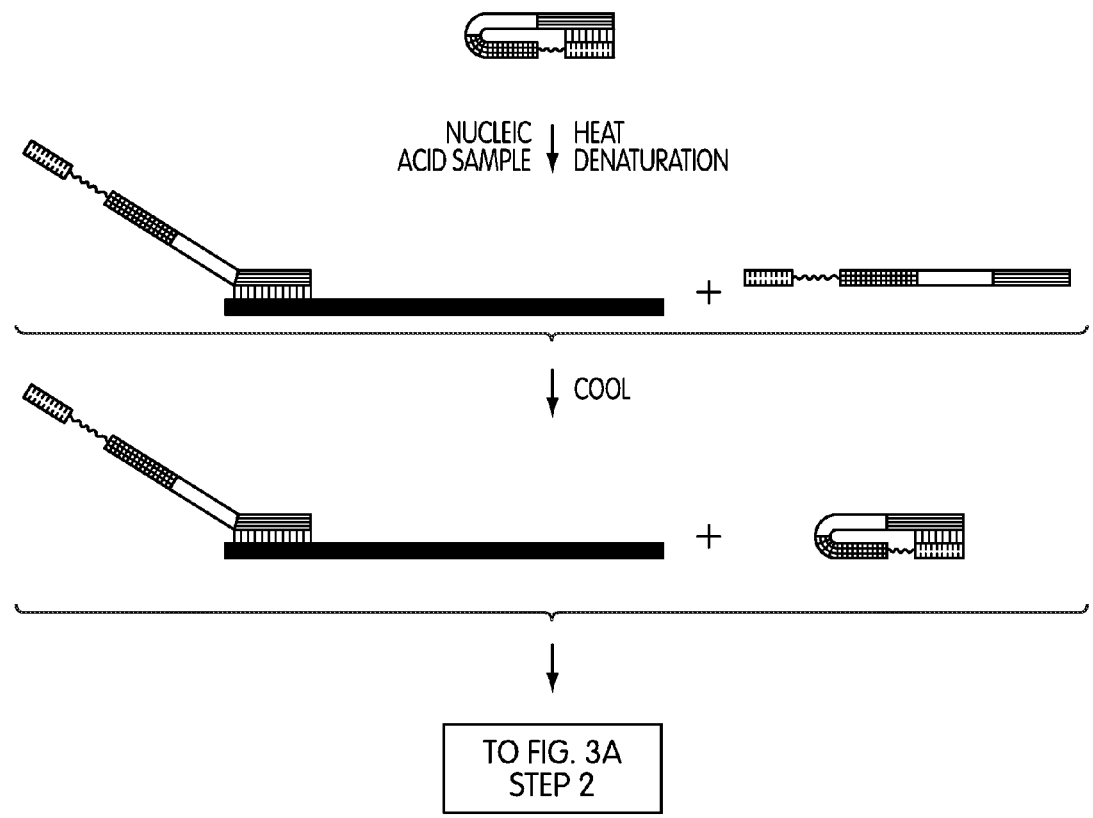
FIG. 4 illustrates the use of a hairpin tag molecule in the amplification reaction of FIGS. 3A and 3B.

FIG. 3 illustrates an adaptation of an isothermal, transcription-based amplification reaction referred to as transcription-mediated amplification (TMA), various aspects of which are disclosed in Kacian et al., U.S. Pat. Nos. 5,399,491 and 5,824,518. The reaction of this illustrative embodiment is initiated by treating an RNA target sequence in a nucleic acid sample with a tagged promoter oligonucleotide. The tagged promoter oligonucleotide includes a tag sequence, a target hybridizing sequence and a promoter sequence for an RNA polymerase, where the target hybridizing sequence hybridizes to a 3'-end of the target sequence. Thus, the target sequence forms a stable complex with the tagged promoter oligonucleotide at the 3'-end of the target sequence prior to initiating a primer extension reaction. See FIG. 3, Step 1. The promoter sequence is situated 5' to the tag sequence, and the tag sequence is situated 5' to the target hybridizing sequence. Unhybridized tagged promoter oligonucleotide is made unavailable for hybridization to the target sequence prior to initiating a primer extension reaction with the tagged priming oligonucleotide, preferably by inactivating and/or removing the unhybridized tagged priming oligonucleotide from the nucleic acid sample.

An extension reaction is then initiated from the 3'-end of the tagged promoter oligonucleotide with a DNA polymerase, e.g., reverse transcriptase, to produce a first DNA primer extension product that includes the tag and promoter sequence and a region complementary to the target sequence. See FIG. 1, Steps 2 and 3. The first DNA primer extension product is then separated from the target sequence to which it is hybridized using an enzyme that selectively degrades that portion of the target sequence which is hybridized to the first DNA primer extension product (e.g., RNAse H activity). See FIG. 3, Step 4.

Next, the first DNA primer extension product is treated with a priming oligonucleotide which hybridizes to a region of the first DNA primer extension product that is complementary to a 5'-end of the target sequence, thereby forming a priming oligonucleotide:first DNA primer extension product hybrid. See FIG. 3, Step 5. The 3'-end of the priming oligonucleotide is extended by a DNA polymerase to produce a second DNA primer extension product complementary to at least a portion of the first DNA primer extension product, and containing a double-stranded promoter sequence. See FIG. 3, Steps 6 and 7. This second DNA primer extension product is used as a template to transcribe multiple copies of a first RNA product complementary to the second DNA primer extension product, not including the promoter portion, using an RNA polymerase which recognizes the double-stranded promoter and initiates transcription therefrom. See FIG. 3, Step 8 and 9. The base sequence of the first RNA product is substantially identical to the base sequence of the tag sequence and the complement of the target sequence.

The first RNA product is treated with the priming oligonucleotide, the 3'-end of which is extended by the DNA polymerase to produce a third DNA primer extension product complementary to the first RNA product. See FIG. 3, Steps 10-12. The third DNA primer extension product is then separated from the first RNA product using an enzyme which selectively degrades the first RNA product (e.g., RNAse H activity). See FIG. 3, Step 13. The third DNA primer extension product is treated with a promoter oligonucleotide having a hybridizing sequence which hybridizes to a complement of the tag sequence at the 3'-end of the third DNA primer extension product, and further comprises a promoter for an RNA polymerase which is situated 5' to the hybridizing sequence. See FIG. 3, Step 14. The 3'-end of the third DNA primer extension product is extended to add sequence complementary to the promoter sequence. See FIG. 3, Step 15. The 3'-end of the promoter oligonucleotide is extended with the DNA polymerase to produce a fourth DNA primer extension product complementary to the third DNA primer extension product. See FIG. 3, Step 16. Multiple copies of a second RNA product complementary to the third DNA primer extension product, not including the promoter portion, are transcribed from the double-stranded promoter and re-enter the amplification cycle at Step 9 of FIG. 3. The base sequence of the second RNA product is substantially identical to the base sequence of the tag sequence and the complement of the target sequence.

Figure 5:
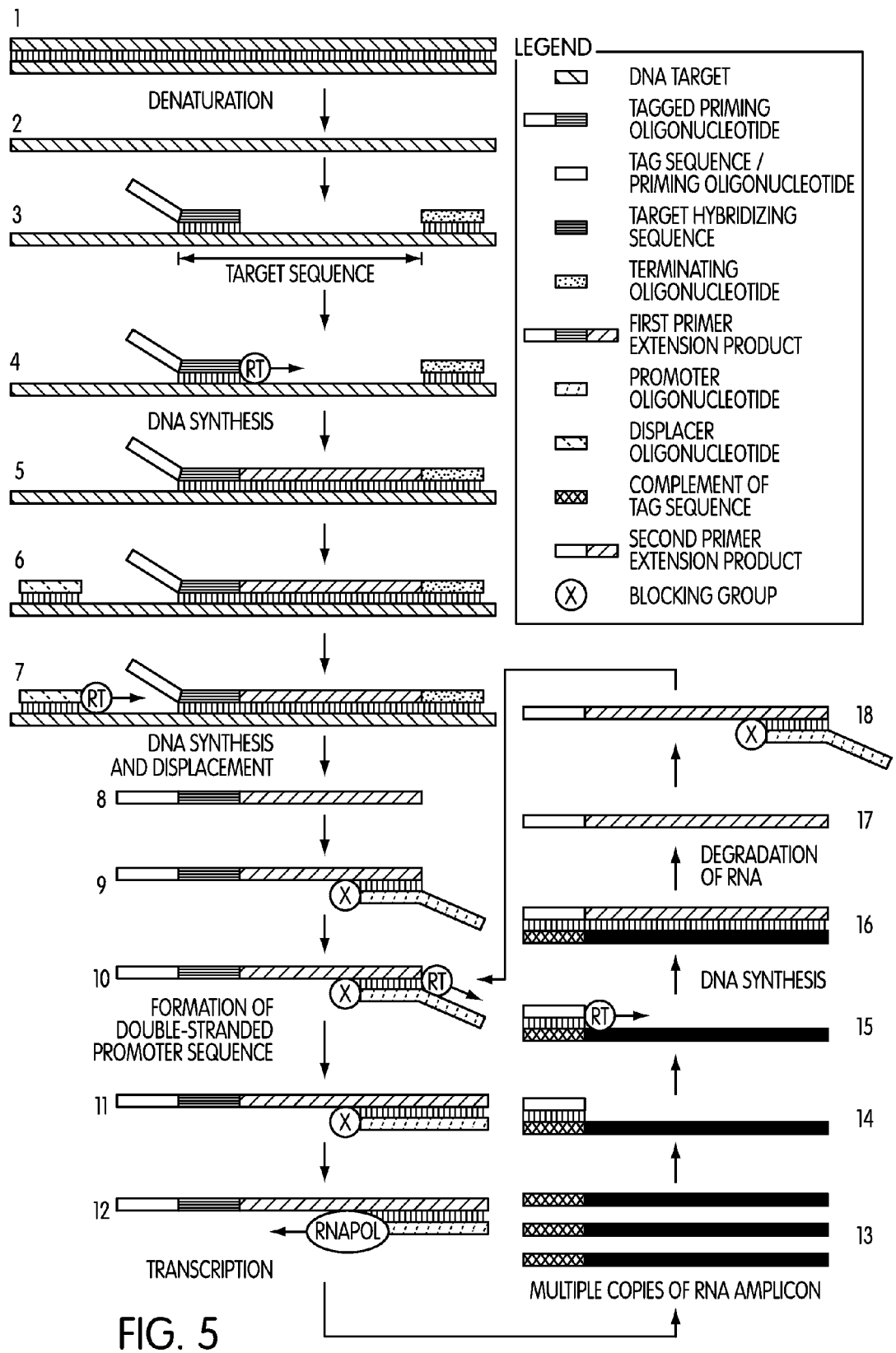
FIG. 5 illustrates the steps of a transcription-based amplification reaction initiated with a tagged priming oligonucleotide that hybridizes to a 3'-end of a single-stranded DNA target sequence. A first extension product formed with the tagged priming oligonucleotide has a 3'-end which is determined by a terminating oligonucleotide hybridized adjacent to or near the 5'-end of the DNA target sequence. A displacer oligonucleotide hybridized 5' to the tagged priming oligonucleotide is extended to form a second extension product which displaces the first extension product from the DNA target sequence. A blocked promoter oligonucleotide hybridizes to a 3'-end of the first extension product and is used to generate RNA transcripts that are cycled into the amplification reaction.
Figure 6:
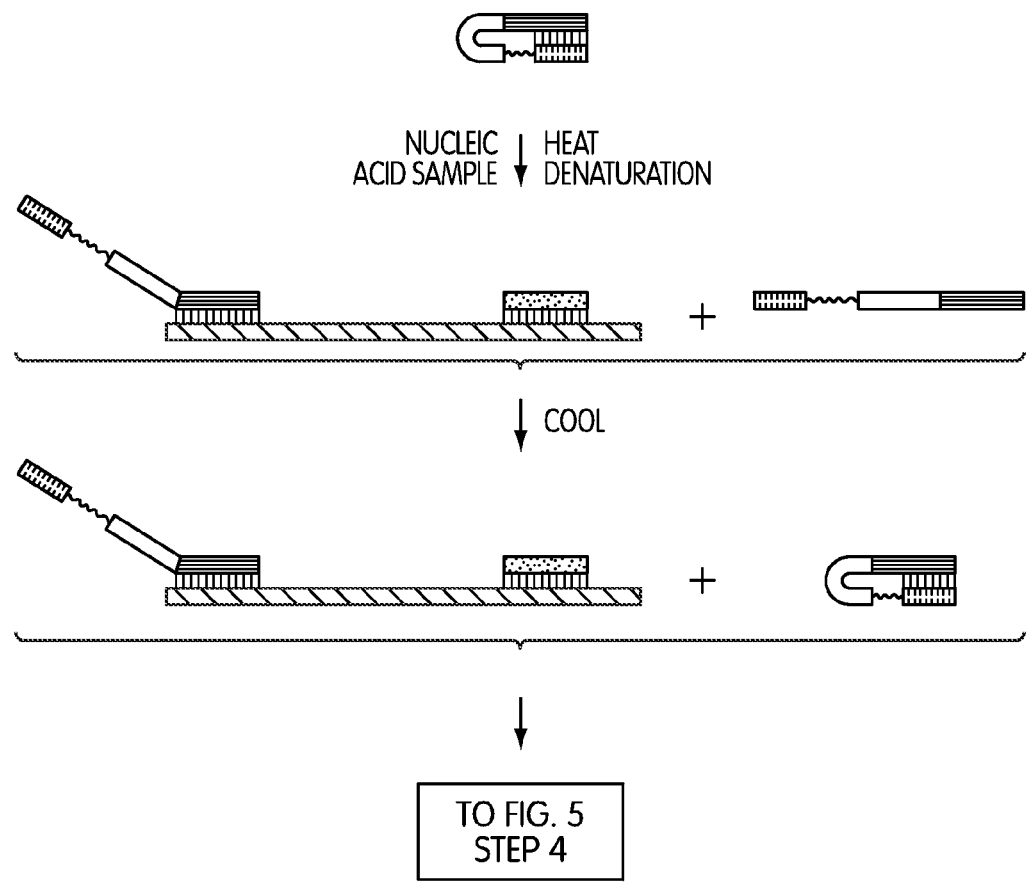
FIG. 6 illustrates the use of a hairpin tag molecule in the amplification reaction of FIG. 5.

FIG. 5 illustrates an adaptation of an rTMA amplification reaction for amplifying a DNA target sequence, various aspects of which are disclosed in Becker et al., U.S. Pat. No. 7,713,697. The reaction of this illustrative embodiment is initiated by treating a DNA target sequence in a nucleic acid sample with a tagged priming oligonucleotide and a terminating oligonucleotide. The tagged priming oligonucleotide includes a target hybridizing sequence hybridized to a 3'-end of the target sequence and a tag sequence situated 5' to the target hybridizing sequence. The target hybridizing sequence preferably hybridizes to a single-stranded form of the target sequence, although it may hybridize to a double-stranded form of the target sequence through strand invasion, which can be facilitated by, for example, DNA breathing (e.g., AT rich regions), low salt conditions, and/or the use of DMSO and/or osmolytes, such as betaine. The target sequence is preferably rendered single-stranded by heating the nucleic acid sample. The terminating oligonucleotide hybridizes to a region of a target nucleic acid containing the target sequence in the vicinity of the 5'-end of the target sequence. The terminating oligonucleotide is used to end primer extension of a nascent nucleic acid that includes the tagged priming oligonucleotide. Thus, the target nucleic acid forms a stable complex with the tagged priming oligonucleotide at the 3'-end of the target sequence and the terminating oligonucleotide located adjacent to or near the 5'-end of the target sequence. See FIG. 5, Steps 1-3. Unhybridized tagged priming oligonucleotide is made unavailable for hybridization to the target sequence prior to initiating a primer extension reaction with the tagged priming oligonucleotide, preferably by inactivating and/or removing the unhybridized tagged priming oligonucleotide from the nucleic acid sample.

An extension reaction is then initiated from the 3'-end of the tagged priming oligonucleotide with a DNA polymerase, e.g., reverse transcriptase, to produce a first DNA primer extension product that includes the tag sequence and a region complementary to the target sequence. See FIG. 5, Steps 4 and 5.

The nucleic acid sample is further treated with a displacer oligonucleotide which hybridizes to the target nucleic acid upstream from the tagged oligonucleotide such that a primer extension reaction can be initiated therefrom, so that the first DNA primer extension product is displaced when a 3'-end of the displacer oligonucleotide is extended by the DNA polymerase. See FIG. 5, Steps 6-8. The order of the illustrated steps is not meant to imply that the nucleic acid sample of this embodiment must be treated with the tagged priming oligonucleotide before it is treated with the displacer oligonucleotide to be operational. In certain embodiments, it is preferable to have these two oligonucleotides hybridize to the target nucleic acid substantially simultaneously.

Next, the first DNA primer extension product is treated with a promoter oligonucleotide having a hybridizing sequence and a promoter for an RNA polymerase situated 5' to the hybridizing sequence. The hybridizing sequence hybridizes to a region of the first DNA primer extension product that is complementary to the 3'-end of the target sequence, thereby forming a promoter oligonucleotide:first DNA primer extension product hybrid. In the illustrated reaction, the promoter oligonucleotide is modified to prevent the initiation of DNA synthesis by situating a blocking moiety at the 3'-end of the promoter oligonucleotide (e.g., nucleotide sequence having a 3'-to-5' orientation). See FIG. 5, Step 9. The 3'-end of the first DNA primer extension product is extended to add sequences complementary to the promoter, resulting in the formation of a double-stranded promoter sequence. See FIG. 5, Steps 10 and 11. Multiple copies of a first RNA product complementary to at least a portion of the first DNA primer extension product, not including the promoter, are transcribed using an RNA polymerase which recognizes the double-stranded promoter and initiates transcription therefrom. See FIG. 5, Step 12 and 13. As a result, the base sequence of the first RNA product is substantially identical to the base sequence of the target sequence and the complement of the tag sequence.

The first RNA products are contacted with a priming oligonucleotide which hybridizes to the complement of the tag sequence to form a priming oligonucleotide:first RNA product hybrid, and the 3'-end of the priming oligonucleotide is extended with the DNA polymerase to produce a second DNA primer extension product complementary to the first RNA product. See FIG. 5, Step 14-16. The second DNA primer extension product is separated from the first RNA product using and enzyme that selectively degrades the first RNA product (e.g., RNAse H activity). See FIG. 5, Step 17.

The second DNA primer extension product is treated with the promoter oligonucleotide to form a promoter oligonucleotide:second DNA primer extension product hybrid. See FIG. 5, Step 18. The promoter oligonucleotide:second primer extension product hybrid then re-enters the amplification cycle at Step 10 of FIG. 5, where transcription is initiated from the double-stranded promoter and the cycle continues.

Figure 7:
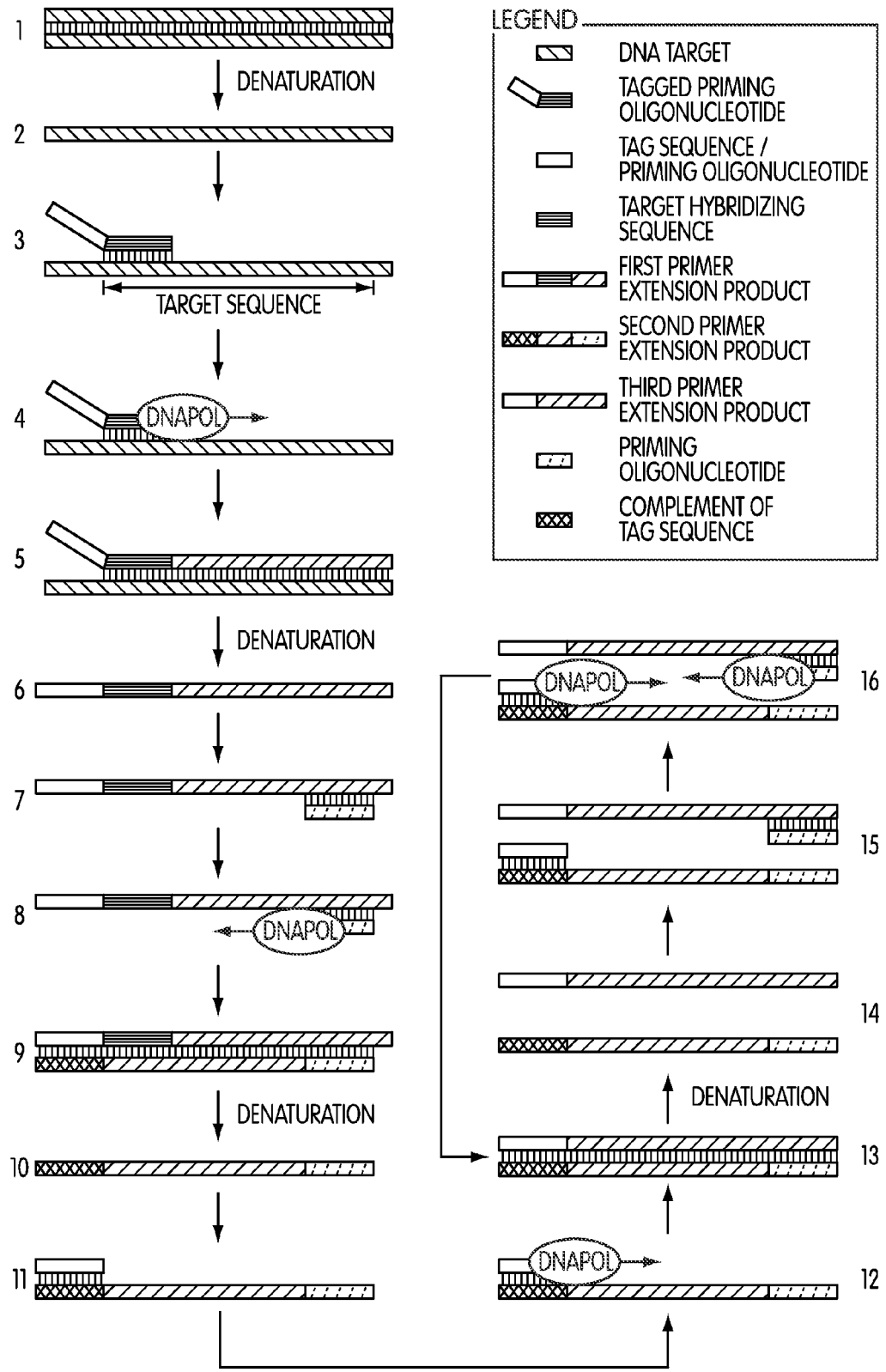
FIG. 7 illustrates the steps polymerase chain reaction that is initiated with a tagged priming oligonucleotide that hybridizes to a DNA target sequence.
Figure 8:
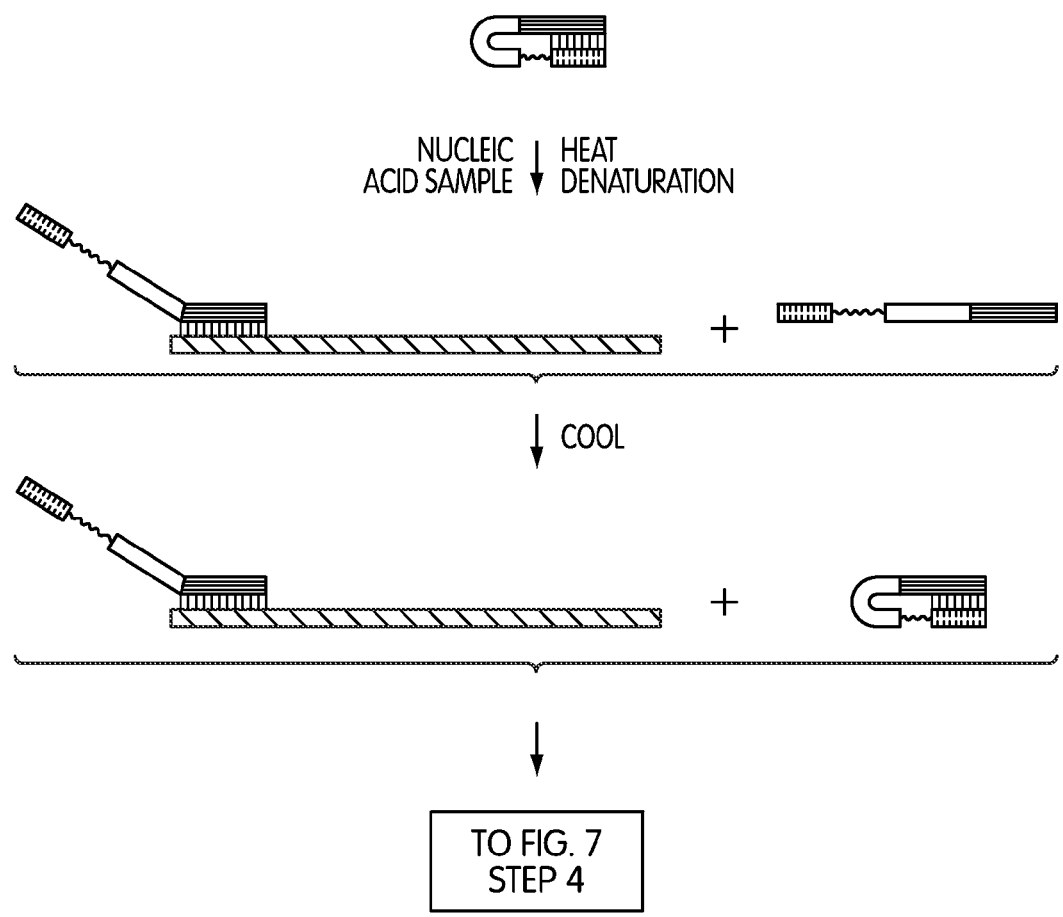
FIG. 8 illustrates the use of a hairpin tag molecule in the amplification reaction of FIG. 7.

FIG. 7 illustrates an adaptation of a polymerase chain reaction (PCR), various aspects of which are disclosed in, for example, Mullis et al., U.S. Pat. Nos. 4,683,195 and 4,800,159; Mullis, U.S. Pat. No. 4,682,202; and Gelfand et al., U.S. Pat. No. 5,804,375. The reaction of this illustrative embodiment is initiated by treating a denatured DNA target sequence in a nucleic acid sample with a tagged priming oligonucleotide. The tagged priming oligonucleotide includes a target hybridizing sequence that hybridizes to a 3'-end of the target sequence and a tag sequence situated 5' to the target hybridizing sequence. Thus, the target sequence forms a stable complex with the tagged priming oligonucleotide at the 3'-end of the target sequence prior to initiating a primer extension reaction. See FIG. 7, Steps 1-3. Unhybridized tagged priming oligonucleotide is made unavailable for hybridization to the target sequence prior to initiating a primer extension reaction with the tagged priming oligonucleotide, preferably by inactivating and/or removing the unhybridized tagged priming oligonucleotide from the nucleic acid sample.

An extension reaction is then initiated from the 3'-end of the tagged priming oligonucleotide with a DNA polymerase, e.g., Taq DNA polymerase, to produce a first DNA primer extension product that includes the tag sequence and a region complementary to the target sequence. See FIG. 7, Steps 4 and 5. Next, the double-stranded product resulting from the first primer extension reaction is denatured and the first DNA primer extension product is contacted with a first priming oligonucleotide which hybridizes to a region of the first DNA primer extension product that is complementary to the 5'-end of the target sequence. See FIG. 7, Steps 6 and 7.

In a second primer extension reaction, the 3'-end of the first priming oligonucleotide is extended with the DNA polymerase to produce a second DNA primer extension product that is complementary to a portion of the first primer extension product and includes the target sequence and the complement of the tag sequence. See FIG. 7, Steps 8 and 9. The double-stranded product resulting from the second primer extension reaction is denatured and the second DNA primer extension product is contacted with a second priming oligonucleotide that hybridizes to the complement of the tag sequence. See FIG. 7, Steps 10 and 11.

The 3'-end of the second priming oligonucleotide is then extended in a third primer extension reaction with the DNA polymerase to produce a third DNA primer extension product that is complementary to the second DNA primer extension product. FIG. 7, Steps 12 and 13. The double-stranded product resulting from the third primer extension reaction is denatured and the second and third DNA primer extension products are available for participation in the repeated cycles of a polymerase chain reaction using as primers the first and second priming oligonucleotides. See FIG. 7, Steps 14-16.

Figure 9:
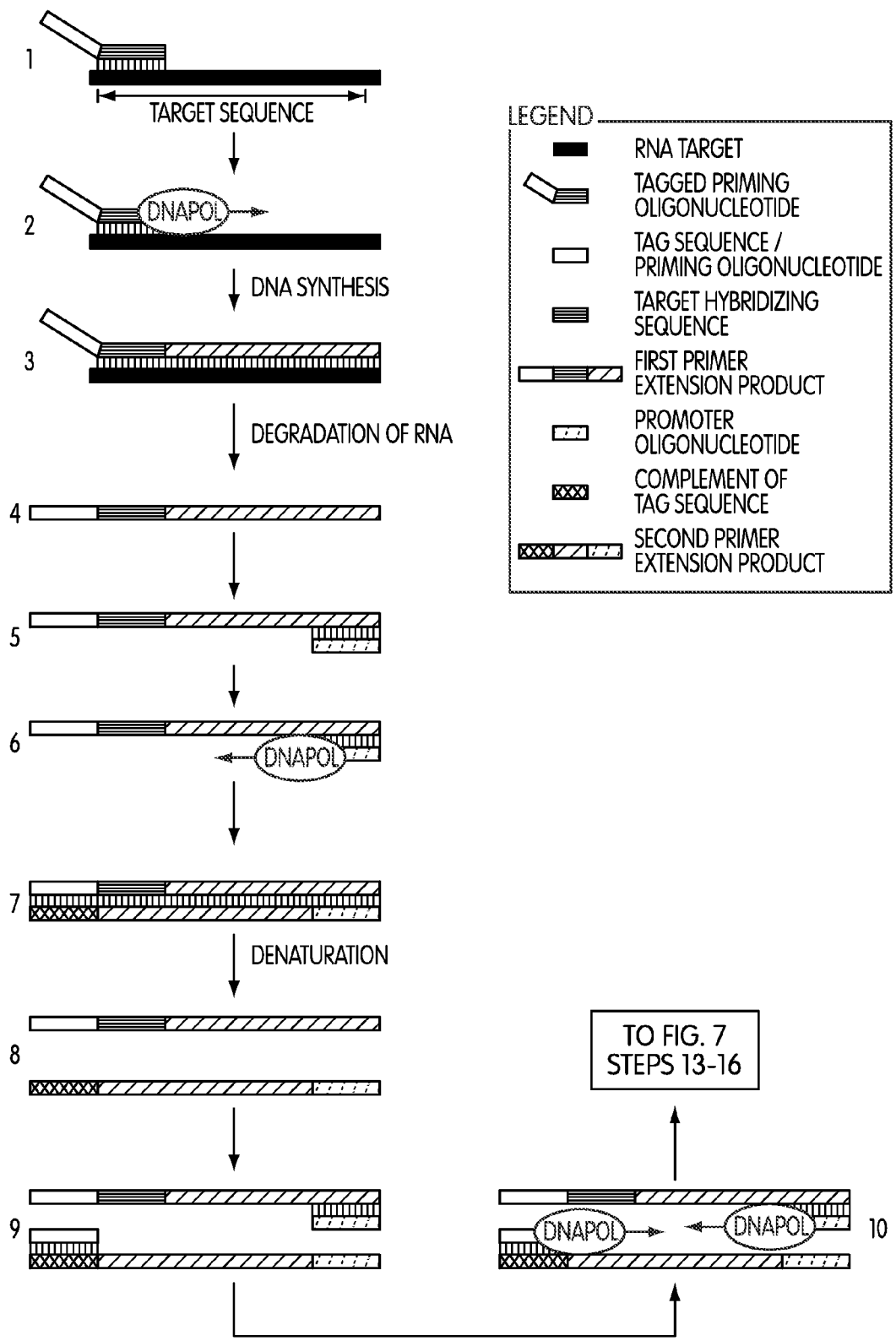
FIG. 9 illustrates the steps of a reverse transcription polymerase chain reaction initiated with a tagged priming oligonucleotide that hybridizes to an RNA target sequence.
Figure 10:
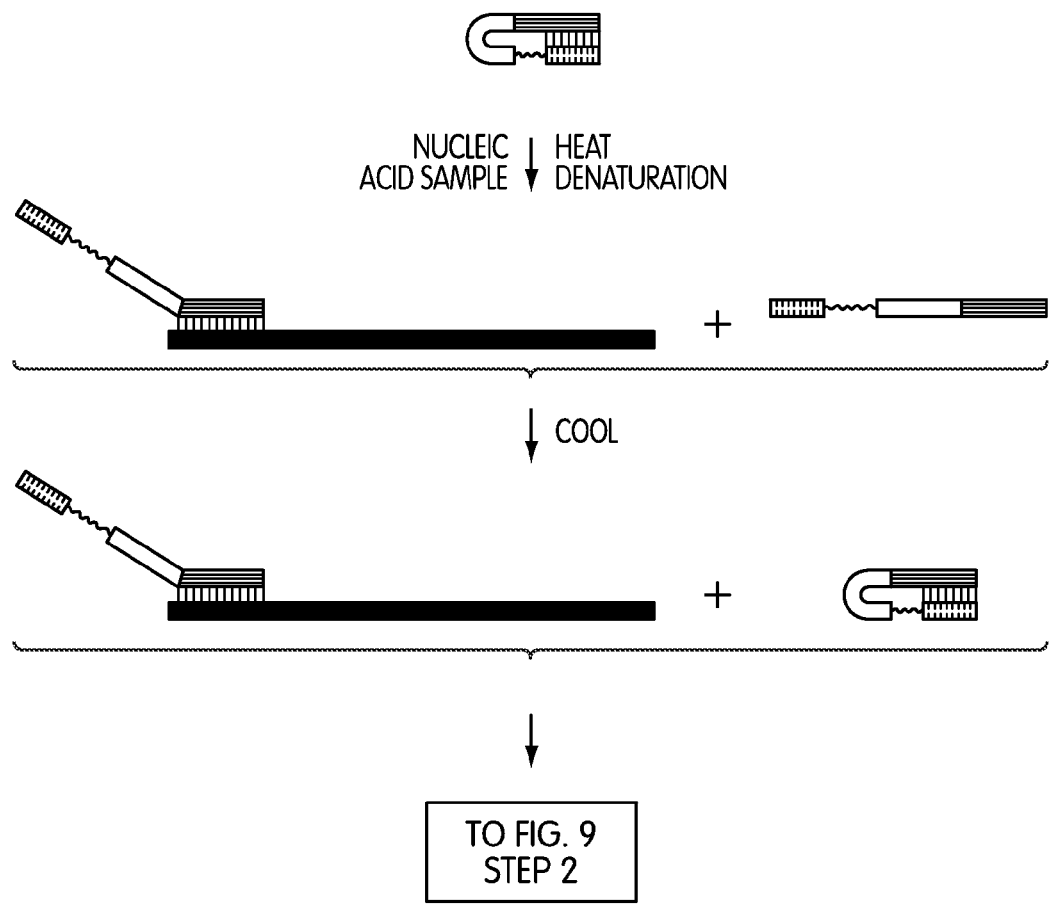
FIG. 10 illustrates the use of a hairpin tag molecule in the amplification reaction of FIG. 9.

FIG. 9 illustrates an adaptation of a reverse transcription polymerase chain reaction (RT-PCR), various aspects of which are disclosed in, for example, Gelfand et al., U.S. Pat. Nos. 5,322,770 and 5,310,652. The reaction of this illustrative embodiment is initiated by treating an RNA target sequence in a nucleic acid sample with a tagged priming oligonucleotide. The tagged priming oligonucleotide includes a target hybridizing sequence and a tag sequence situated 5' to the target hybridizing sequence. Thus, the target sequence forms a stable complex with the tagged priming oligonucleotide at the 3'-end of the target sequence prior to initiating a primer extension reaction. See FIG. 9, Step 1. Unhybridized tagged priming oligonucleotide is made unavailable for hybridization to the target sequence prior to initiating a primer extension reaction with the tagged priming oligonucleotide, preferably by inactivating and/or removing the unhybridized tagged priming oligonucleotide from the nucleic acid sample.

An extension reaction is then initiated from the 3'-end of the tagged priming oligonucleotide with a DNA polymerase, e.g., MasterAmp™ Tth DNA Polymerase, to produce a first DNA primer extension product that includes the tag sequence and a region complementary to the target sequence. See FIG. 9, Steps 2 and 3. The first DNA primer extension product is then separated from the target nucleic acid sequence to which it is hybridized using an enzyme that selectively degrades that portion of a target nucleic acid containing the target sequence that is complementary to the first DNA primer extension product (e.g., RNAse H activity). See FIG. 9, Step 4.

Next, the first DNA primer extension product is treated with a first priming oligonucleotide which hybridizes to a region of the first DNA primer extension product that is complementary to the 5'-end of the target sequence to form a first DNA primer extension product:first priming oligonucleotide hybrid. See FIG. 9, Step 5. A second primer extension reaction extends the 3'-end of the first priming oligonucleotide with the DNA polymerase to produce a DNA second primer extension product complementary to at least a portion of the first primer extension product and includes the target sequence and the complement of the tag sequence. See FIG. 9, Steps 6 and 7. The first and second DNA primer extension products are then separated from each other by denaturation. See FIG. 9, Step 8. The first and second extension products are then available to participate in the repeated cycles of a polymerase chain reaction using as primers the first priming oligonucleotide and a second priming oligonucleotide which hybridizes to the complement of the tag sequence. See FIG. 9, Steps 9 and 10; FIG. 7, Steps 13-16.

In other illustrative embodiments of the present invention, a heterologous tag sequence which has not formed part of a tagged target nucleic acid sequence is inactivated prior to exposing the tagged target nucleic acid sequence to reagents and conditions sufficient for detectable amplification of a target nucleic acid sequence. In a preferred aspect, the inactivated heterologous tag sequence is in the form of a tagged oligonucleotide which has not hybridized to the target nucleic acid sequence. Tagged oligonucleotides are described above and include first and second regions, where the first region comprises a target hybridizing sequence which hybridizes to a 3'-end of a target nucleic acid sequence under a first set of conditions, and the second region comprises a tag sequence which is located 5' to the first region of the tagged oligonucleotide. The target hybridizing sequence has a free 3' hydroxyl group that can be enzymatically extended in the presence of a DNA polymerase in a template-dependent manner. The tagged oligonucleotide has an "active" confirmation which permits the target hybridizing sequence to hybridize to the target nucleic acid sequence and an "inactive" confirmation which blocks the target hybridizing sequence from hybridizing to the target nucleic acid sequence. The inactive confirmation is generally formed under less stringent conditions than the conditions for forming the active confirmation of the tagged oligonucleotide.

The inactive confirmation of the tagged oligonucleotide can be formed by hybridizing a tag closing sequence to the target hybridizing sequence of the tagged oligonucleotide. The tag closing sequence can constitute a discrete molecule or it can be tethered to the tagged oligonucleotide by a linker which joins the 3'-end or 5'-end of the tag closing sequence to the 5'-end of a region of the tagged oligonucleotide containing a tag sequence ("tagged priming oligonucleotide") or a promoter sequence located 5' to a tag sequence ("tagged promoter oligonucleotide"), thereby forming a self-hybridized, hairpin tag molecule comprising the tagged oligonucleotide. The linker does not include nucleotide bases that can be copied by a polymerase and is preferably a non-nucleotide linker comprised of non-nucleotide constituents. Suitable non-nucleotide linkers for joining the tag closing sequence to the tagged oligonucleotide include abasic nucleotides and polyethylene glycol. Other suitable linkers include nucleotide analogs, such as LNAs and 2'-O-Me. The association kinetics are best when the tag closing sequence and the target hybridizing sequence of the tagged oligonucleotide are contained in the same molecule.

Figure 11:
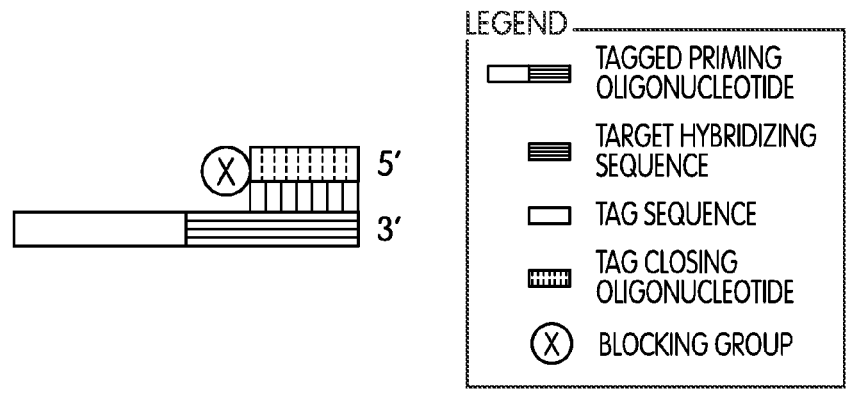
FIG. 11 illustrates a discrete, 3' blocked tag closing oligonucleotide hybridized in an antiparallel fashion to the 3'-end of a tagged priming oligonucleotide, thereby blocking hybridization of the tagged priming oligonucleotide to a target nucleic acid sequence.
Figure 12:
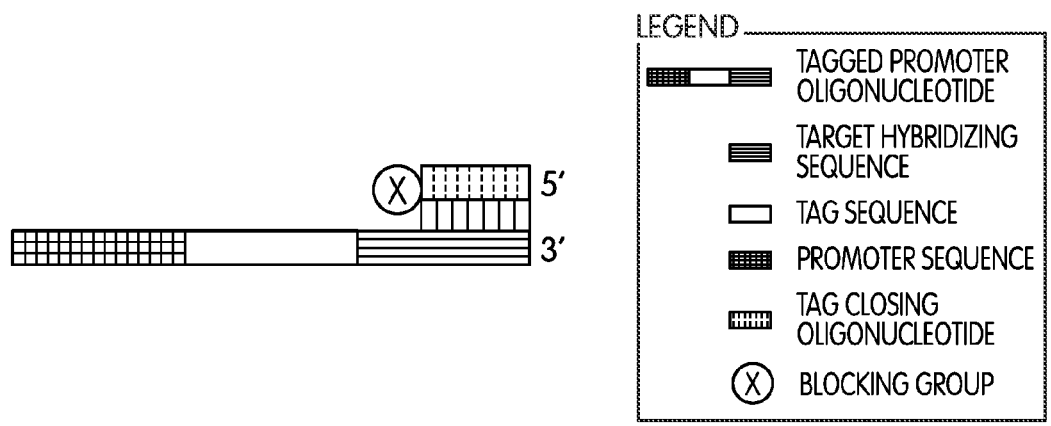
FIG. 12 illustrates a discrete, 3' blocked tag closing oligonucleotide hybridized in an antiparallel fashion to the 3'-end of a tagged promoter oligonucleotide, thereby blocking hybridization of the tagged promoter oligonucleotide to a target nucleic acid sequence.
Figure 13:
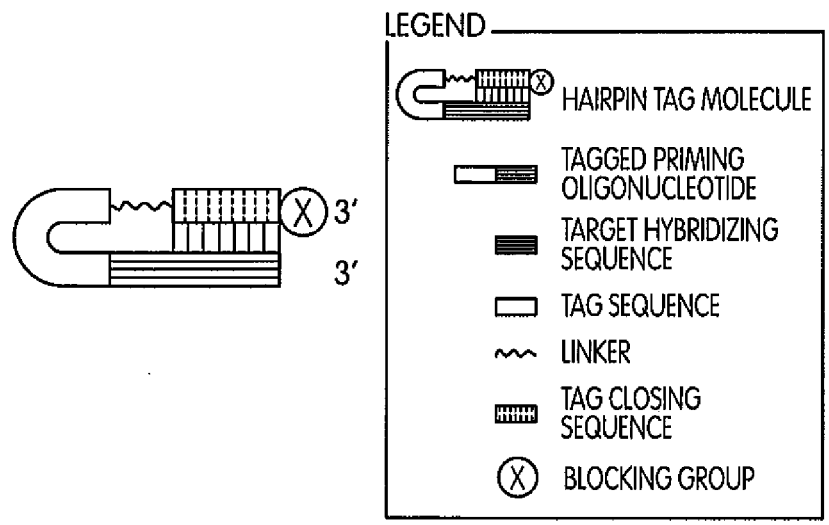
FIG. 13 illustrates a hairpin tag molecule that includes a 3' blocked tag closing sequence hybridized in a parallel fashion to the 3'-end of a tagged priming oligonucleotide, thereby blocking hybridization of the tagged priming oligonucleotide to a target nucleic acid sequence. A 5'-end of the tag closing sequence is joined to the 3'-end of a tag sequence of the tagged priming oligonucleotide by a non-nucleotide linker.
Figure 14:
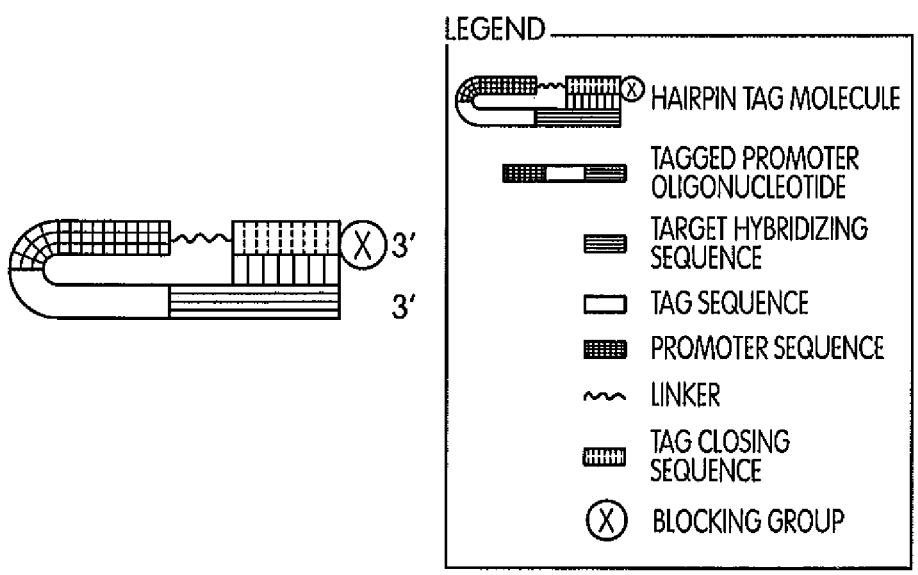
FIG. 14 illustrates a hairpin tag molecule that includes a 3' blocked tag closing sequence hybridized in a parallel fashion to the 3'-end of a tagged promoter oligonucleotide, thereby blocking hybridization of the tagged promoter oligonucleotide to a target nucleic acid sequence. A 5'-end of the tag closing sequence is joined to the 3'-end of a promoter sequence of the tagged promoter oligonucleotide by a non-nucleotide linker.
Figure 15:
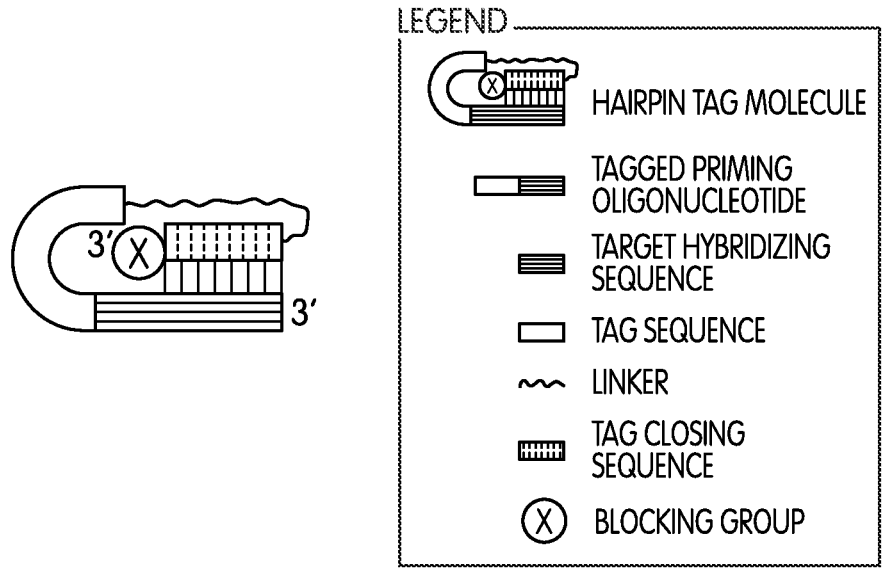
FIG. 15 illustrates a hairpin tag molecule that includes a 3' blocked tag closing sequence hybridized in an antiparallel fashion to the 3'-end of a tagged priming oligonucleotide, thereby blocking hybridization of the tagged priming oligonucleotide to a target nucleic acid sequence. A 5'-end of the tag closing sequence is joined to the 3'-end of a tag sequence of the tagged priming oligonucleotide by a non-nucleotide linker.
Figure 16:
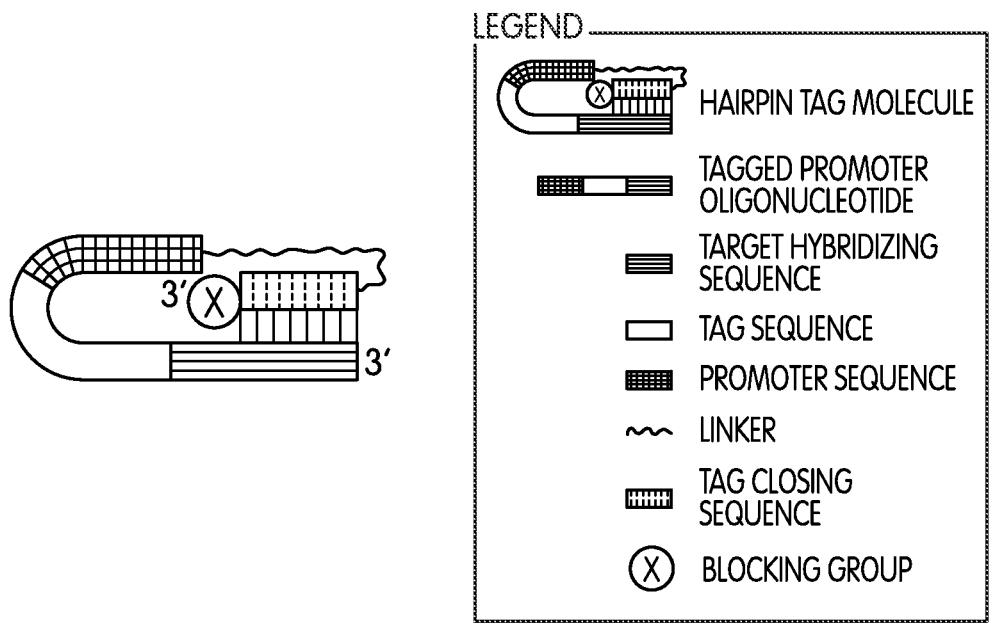
FIG. 16 illustrates a hairpin tag molecule that includes a 3' blocked tag closing sequence hybridized in an antiparallel fashion to the 3'-end of a tagged promoter oligonucleotide, thereby blocking hybridization of the tagged promoter oligonucleotide to a target nucleic acid sequence. A 5'-end of the tag closing sequence is joined to the 3'-end of a promoter sequence of the tagged promoter oligonucleotide by a non-nucleotide linker.

Under selective conditions, the tag closing sequence can hybridize to the target hybridizing sequence of the tagged oligonucleotide in an antiparallel orientation, as shown in FIGS. 2, 4, 6, 8, 10, 11, 12, 15 and 16, or in a parallel orientation, as shown in FIGS. 13 and 14. If the tag closing sequence is a discrete molecule, as illustrated in FIGS. 11 and 12, or joined to the tagged oligonucleotide by a non-nucleotide linker attached to its 5'-end, as illustrated in FIGS. 2, 4, 6, 8, 10, 15 and 16, then the tag closing sequence is preferably modified to prevent primer extension by a DNA polymerase, such as by positioning a blocking moiety at its 3'-terminus. Suitable blocking moieties are described herein. When hybridized in an antiparallel orientation, as illustrated in FIGS. 13 and 14, the 3'-terminal base of the tag closing sequence is preferably hybridized to the 3'-terminal base of the target hybridizing sequence of the tagged oligonucleotide. More preferably, the tag closing sequence is modified to prevent primer extension by a DNA polymerase.

The length and base content of the tag closing sequence are selected so that hybridization of the tagged oligonucleotide to the target nucleic acid sequence is favored under a first set of conditions and, when the tagged oligonucleotide is not hybridized to the target nucleic acid sequence, so that the tag closing sequence can form a stable hybrid with the target hybridizing sequence under a second, less stringent set of conditions. The tag closing sequence should be selected so that it is not readily displaced from the target hybridizing sequence under the amplification conditions to which it may be subjected. Typically, the tag closing sequence will hybridize to from 5 to 20 contiguous or non-contiguous bases of the target hybridizing sequence. Suitable tag closing sequences preferably range from 5 to 15 bases in length. To bias the target hybridizing sequence toward the target nucleic acid under the first set of conditions, the tag closing sequence may include, for example, one or more abasic nucleotides, base mismatches or members of wobble base pairs. Tag closing sequences are preferably selected to specifically hybridize to the target hybridizing sequence more strongly than any non-specific interactions with other nucleic acids present in an amplification reaction.

Following inactivation, inactive tagged oligonucleotides are preferably removed from a sample to limit unintended interactions with target nucleic acid sequences entering the sample from a potentially contaminating source. Removal can be accomplished by immobilizing target nucleic acids in a sample on a solid support and then removing other components of the sample, including inactivated tagged oligonucleotides. To ensure that inactive tagged oligonucleotides are removed, the number of non-specific interactions between the solid support and nucleic acids present in the sample should be limited. Any known solid support may be used for sample processing, such as matrices and particles that are free in solution. Particularly preferred supports are magnetic spheres that are monodisperse (i.e., uniform in size±5%), thereby providing consistent results, which is particularly advantageous for use in an automated procedure.

Particularly preferred amplification techniques for incorporating the tagged oligonucleotides of the present invention include isothermal amplification reactions, such as TMA and variations of TMA, like real-time TMA, which incorporates one or more feature of the methods described by Becker et al., U.S. Pat. No. 7,374,885, and Becker et al., U.S. Pat. No. 7,713,697. For example, certain preferred real-time TMA methods include the use of blocking moieties, terminating moieties, and/or other modifying moieties that provide improved TMA process sensitivity and accuracy.

Promoter oligonucleotides may be modified to prevent the synthesis of DNA therefrom. For example, a promoter oligonucleotide may comprise a blocking moiety attached at its 3'-terminus to prevent primer extension in the presence of a polymerase. In one example, at least about 80% of the oligonucleotides present in the amplification reaction which comprise a promoter further comprise a 3'-blocking moiety. In another embodiment, at least about 85%, 90%, 95%, 96%, 97%, 98%, 99% or 100% of the oligonucleotides provided to the amplification reaction which comprise a promoter are further modified to comprise a 3'-blocking moiety. In another embodiment, any oligonucleotide used in an amplification reaction of the present invention which comprises a promoter sequence further comprises a 3'-terminus blocking moiety.

Certain embodiments of the present invention relate to amplification of a target nucleic acid comprising an RNA target sequence. In some cases, the target nucleic acid has indeterminate 3'- and 5'-ends relative to the desired RNA target sequence. The target nucleic acid is treated with a priming oligonucleotide which has a base region sufficiently complementary to a 3'-end of the RNA target sequence to hybridize therewith and, as discussed above, further comprises a heterologous tag sequence in the first primer extension reaction. Priming oligonucleotides are designed to hybridize to a suitable region of any desired target sequence, according to primer design methods well known to those of ordinary skill in the art. While the presence of the tag sequence in a priming oligonucleotide may alter the binding characteristics of a target hybridizing region to a target nucleic acid sequence, the artisan skilled in the molecular arts can readily design priming oligonucleotides which contain both target hybridizing regions and tag sequences that can be used in accordance with the methods described herein. Suitable priming oligonucleotides are described in more detail herein. Additionally, the 5'-end of a priming oligonucleotide (preferably not a tagged priming oligonucleotide) may include one or modifications which improve the binding properties (e.g., hybridization or base stacking) of the priming oligonucleotide to a DNA extension product or to an RNA amplification product, as discussed more fully infra, provided the modifications do not substantially interfere with the priming function of the priming oligonucleotide or cleavage of an RNA amplification product to which the priming oligonucleotide is hybridized. The 3'-end of the priming oligonucleotide is extended by an appropriate DNA polymerase, e.g., an RNA-dependent DNA polymerase ("reverse transcriptase") in an extension reaction using the RNA target sequence or amplification product as a template to give a DNA primer extension product which is complementary to the RNA template or amplification product.

DNA primer extension products are separated (at least partially) from an RNA template using an enzyme which degrades the RNA template or amplification product. Suitable enzymes, i.e., "selective RNAses," are those which act on the RNA strand of an RNA:DNA complex, and include enzymes which comprise an RNAse H activity. Some reverse transcriptases include an RNAse H activity, including those derived from Moloney murine leukemia virus and avian myeloblastosis virus. According to preferred amplification embodiments, the selective RNAse may be provided as an RNAse H activity of a reverse transcriptase, or may be provided as a separate enzyme, e.g., as an *E. coli* RNAse H or a *T. thermophilus* RNAse H. Other enzymes which selectively degrade RNA present in an RNA:DNA duplex may also be used.

When the target sequence is DNA, a DNA primer extension product can be separated from the template by treating the target nucleic acid with a displacer oligonucleotide. The displacer oligonucleotide has a priming function and is designed to hybridize to the target nucleic acid upstream from the priming oligonucleotide (referred to as the "forward priming oligonucleotide" in this embodiment). By "upstream" is meant that a 3'-end of the displacer oligonucleotide hybridizes to the target nucleic acid upstream from a 3'-end of the forward priming oligonucleotide. Thus, the displacer oligonucleotide and the forward priming oligonucleotide may hybridize to overlapping or distinct regions of the target nucleic acid. In preferred embodiments, the 3'-terminus of the displacer oligonucleotide is adjacent to or spaced up to 5 to 35 bases from the 5'-terminus of the forward priming oligonucleotide relative to the target nucleic acid (i.e., the target nucleic acid has up to 5 to 35, contiguous unbound nucleotides situated between the 3'-terminal base of the displacer oligonucleotide and the 5'-terminal base of the priming oligonucleotide when both oligonucleotides are hybridized to the target nucleic acid). The displacer oligonucleotide is generally from 10 to 50 nucleotides in length and may include one or more modifications at the 5'-end which improve the binding properties (e.g., hybridization or base stacking) of the displacer oligonucleotide to the target nucleic acid, provided that the modifications do not substantially interfere with the priming function of the displacer oligonucleotide. The displacer oligonucleotide and the forward priming oligonucleotide are designed to hybridize to the target nucleic acid under the same conditions. The target nucleic acid is preferably treated with the displacer oligonucleotide after the forward priming oligonucleotide has had sufficient time to hybridize to the target nucleic acid. Alternatively, the target nucleic acid is treated with both the displacer oligonucleotide and the forward priming oligonucleotide before exposing the mixture to a polymerase suitable for extending the 3'-ends of the displacer oligonucleotide and the forward priming oligonucleotide. In the presence of the DNA polymerase, the 3'-end of the displacer oligonucleotide is extended in a template-dependent manner to form a second DNA primer extension product which displaces the first DNA primer extension product from the target nucleic acid, thereby making it available for hybridization to a promoter oligonucleotide. In an alternative approach, conditions could be established whereby the promoter oligonucleotide gains access the first DNA primer extension product through stand invasion facilitated by, for example, DNA breathing (e.g., AT rich regions), low salt conditions, and/or the use of DMSO and/or osmolytes, such as betaine. The promoter oligonucleotide of this embodiment is the same as that described above and, likewise, is modified to prevent the promoter oligonucleotide from functioning as a priming oligonucleotide for a DNA polymerase (e.g., the promoter oligonucleotide includes a blocking moiety at its 3'-terminus).

In certain embodiments, the methods of the present invention further comprise treating the target nucleic acid as described above to limit the length of the DNA primer extension product to a certain desired length. Such length limitation is typically carried out through use of a "binding molecule" which hybridizes to or otherwise binds to the RNA target nucleic acid adjacent to or near the 5'-end of the desired target sequence. In certain embodiments, a binding molecule comprises a base region. The base region may be DNA, RNA, a DNA:RNA chimeric molecule, or an analog thereof. Binding molecules comprising a base region may be modified in one or more ways, as described elsewhere herein. Suitable binding molecules include, but are not limited to, a binding molecule comprising a terminating oligonucleotide or a terminating protein that binds RNA and prevents primer extension past its binding region, or a binding molecule comprising a modifying molecule, for example, a modifying oligonucleotide such as a "digestion" oligonucleotide that directs hydrolysis of that portion of the RNA target hybridized to the digestion oligonucleotide, or a sequence-specific nuclease that cuts the RNA target.

Illustrative terminating oligonucleotides of the present invention have a 5'-base region sufficiently complementary to the target nucleic acid at a region adjacent to, near to, or overlapping with the 5'-end of the target sequence, to hybridize therewith. In certain embodiments, a terminating oligonucleotide is synthesized to include one or more modified nucleotides. For example, certain terminating oligonucleotides of the present invention comprise one or more 2'-O-ME ribonucleotides, or are synthesized entirely of 2'-O-ME ribonucleotides. See, e.g., Majlessi et al. (1998) *Nucleic Acids Res.*, 26, 2224-2229. A terminating oligonucleotide of the present invention typically also comprises a blocking moiety at its 3'-end to prevent the terminating oligonucleotide from functioning as a primer for a DNA polymerase. In some embodiments, the 5'-end of a terminating oligonucleotide of the present invention overlaps with and is complementary to at least about 2 nucleotides of the 5'-end of the target sequence. Typically, the 5'-end of a terminating oligonucleotide of the present invention overlaps with and is complementary to at least 3, 4, 5, 6, 7, or 8 nucleotides of the 5'-end of the target sequence, but no more than about 10 nucleotides of the 5'-end of the target sequence. (As used herein, the term "end" refers to a 5'- or 3'-region of an oligonucleotide, nucleic acid or nucleic acid region which includes, respectively, the 5'- or 3'-terminal base of the oligonucleotide, nucleic acid or nucleic acid region.) Suitable terminating oligonucleotides are described in more detail herein.

A single-stranded DNA primer extension product, or "first" DNA primer extension product, which has either a defined 3'-end or an indeterminate 3'-end, is treated with a promoter oligonucleotide which comprises a first region sufficiently complementary to a 3'-region of the DNA primer extension product to hybridize therewith, a second region comprising a promoter for an RNA polymerase, e.g., T7 polymerase, which is situated 5' to the first region, e.g., immediately 5' to or spaced from the first region, and modified to prevent the promoter oligonucleotide from functioning as a primer for a DNA polymerase (e.g., the promoter oligonucleotide includes a blocking moiety attached at its 3'-terminus). Upon identifying a desired hybridizing "first region," suitable promoter oligonucleotides can be constructed by one of ordinary skill in the art using only routine procedures. Those of ordinary skill in the art will readily understand that a promoter region has certain nucleotides which are required for recognition by a given RNA polymerase. In addition, certain nucleotide variations in a promoter sequence might improve the functioning of the promoter with a given enzyme, including the use of insertion sequences.

Insertion sequences may be positioned between the first and second regions of promoter oligonucleotides and function to increase amplification rates. (The tag sequence of a tagged promoter oligonucleotide may provide this beneficial effect.) The improved amplification rates may be attributable to several factors. First, because an insertion sequence increases the distance between the 3'-end and the promoter sequence of a promoter oligonucleotide, it is less likely that a polymerase, e.g., reverse transcriptase, bound at the 3'-end of the promoter oligonucleotide will interfere with binding of the RNA polymerase to the promoter sequence, thereby increasing the rate at which transcription can be initiated. Second, the insertion sequence selected may itself improve the transcription rate by functioning as a better template for transcription than the target sequence. Third, since the RNA polymerase will initiate transcription at the insertion sequence, the primer extension product synthesized by the priming oligonucleotide, using the RNA transcription product as a template, will contain the complement of the insertion sequence toward the 3'-end of the primer extension product. By providing a larger target binding region, i.e., one which includes the complement of the insertion sequence, the promoter oligonucleotide may bind to the primer extension product faster, thereby leading to the production of additional RNA transcription products sooner. Insertion sequences are preferably 5 to 20 nucleotides in length and should be designed to minimize intramolecular folding and intermolecular binding with other oligonucleotides present in the amplification reaction mixture. Programs which aid in minimizing secondary structure are well known in the art and include Michael Zucker's mfold software for predicting RNA and DNA secondary structure using nearest neighbor thermodynamic rules. The latest version of Michael Zucker's mfold software can be accessed on the Web at www.bioinfo.rpi.edu/applications/mfold using a hypertext transfer protocol (http) in the URL. Useful insertion sequences may be identified using in vitro selection methods well known in the art without engaging in anything more than routine experimentation.

Assaying promoter oligonucleotides with variations in the promoter sequences is easily carried out by the skilled artisan using routine methods. Furthermore, if it is desired to utilize a different RNA polymerase, the promoter sequence in the promoter oligonucleotide is easily substituted by a different promoter. Substituting different promoter sequences is well within the understanding and capabilities of those of ordinary skill in the art. For real-time TMA, promoter oligonucleotides provided to the amplification reaction mixture are modified to prevent efficient initiation of DNA synthesis from their 3'-termini, and preferably comprise a blocking moiety attached at their 3'-termini. Furthermore, terminating oligonucleotides and capping oligonucleotides, and even probes used in certain embodiments of the present invention also optionally comprise a blocking moiety attached at their 3'-termini.

Where a terminating oligonucleotide is used, the first region of the promoter oligonucleotide is designed to hybridize with a desired 3'-end of the DNA primer extension product with substantial, but not necessarily exact, precision. Subsequently, the second region of the promoter oligonucleotide may act as a template, allowing the first DNA primer extension product to be further extended to add a base region complementary to the second region of the promoter oligonucleotide, i.e., the region comprising the promoter sequence, rendering the promoter double-stranded. An RNA polymerase which recognizes the promoter binds to the promoter sequence, and initiates transcription of multiple RNA copies complementary to the DNA primer extension product, which copies are substantially identical to the target sequence. By "substantially identical" it is meant that the multiple RNA copies may have additional nucleotides either 5' or 3' relative to the target sequence, or may have fewer nucleotides either 5' or 3' relative to the target sequence, depending on, e.g., the boundaries of "the target sequence," the transcription initiation point, or whether the priming oligonucleotide comprises additional nucleotides 5' of the primer region (e.g., a linked "cap" as described herein). Where a target sequence is DNA, the sequence of the RNA copies is described herein as being "substantially identical" to the target sequence. It is to be understood, however, that an RNA sequence which has uridine residues in place of the thymidine residues of the DNA target sequence still has a "substantially identical" sequence. The RNA transcripts so produced may automatically recycle in the above system without further manipulation. Thus, this reaction is autocatalytic. In those embodiments where a binding molecule or other means for terminating a primer extension reaction is not used, the first region of the promoter oligonucleotide is designed to hybridize with a selected region of the first DNA primer extension product which is expected to be 5' to the 3'-terminus of the first DNA primer extension product, but since the 3'-terminus of the first DNA primer extension product is indeterminate, the region where the promoter oligonucleotide hybridizes probably will not be at the actual 3'-end of the first DNA primer extension product. According to this embodiment, it is generally the case that at least the 3'-terminal base of the first DNA primer extension product does not hybridize to the promoter oligonucleotide. Thus, according to this embodiment the first DNA primer extension product will likely not be further extended to form a double-stranded promoter.

The formation of a double-stranded promoter sequence through extension of a template nucleic acid is not necessary to permit initiation of transcription of RNA complementary to the first DNA primer extension product. The resulting "first" RNA products are substantially identical to the target sequence, having a 5'-end defined by the transcription initiation point, and a 3'-end defined by the 5'-end of the first DNA primer extension product. A sufficient number of first RNA products are produced to automatically recycle in the system without further manipulation. The priming oligonucleotide hybridizes to the 3'-end of the first RNA products, and is extended by a DNA polymerase to form a second DNA primer extension product. Unlike the first DNA primer extension product formed without the use of a terminating oligonucleotide or other binding molecule, the second DNA primer extension product has a defined 3'-end which is complementary to the 5'-ends of the first RNA products. The second DNA primer extension product is separated (at least partially) from the RNA template using an enzyme which selectively degrades the RNA template. The single-stranded second DNA primer extension product is then treated with a promoter oligonucleotide as described above, and the second region of the promoter oligonucleotide acts as a template, allowing the second DNA primer extension product to be further extended to add a base region complementary to the second region of the promoter oligonucleotide, i.e., the region comprising the promoter sequence, rendering the promoter double-stranded. An RNA polymerase which recognizes the promoter binds to the promoter sequence, and initiates transcription of multiple "second" RNA products complementary to the second DNA primer extension product, and substantially identical to the target sequence. The second RNA transcripts so produced automatically recycle in the above system without further manipulation. Thus, this reaction is autocatalytic.

In any of the embodiments described above, once a desired region for the target sequence is identified, that region can be analyzed to determine where selective RNAse degradation will optimally cause cuts or removal of sections of RNA from the RNA:DNA duplex. Analyses can be conducted to determine the effect of the RNAse degradation of the target sequence by RNAse H activity present in AMV reverse transcriptase or MMLV reverse transcriptase, by an exogenously added selective enzyme with an RNAse activity, e.g., E. coli RNAse H, or selective enzymes with an RNAse activity from other sources, and by combinations thereof. Following such analyses, the priming oligonucleotide can be selected for so that it will hybridize to a section of RNA which is substantially nondegraded by the selective RNAse present in the reaction mixture, because substantial degradation at the binding site for the priming oligonucleotide could inhibit initiation of DNA synthesis and prevent optimal extension of the primer. In other words, a priming oligonucleotide is typically selected to hybridize with a region of the RNA target nucleic acid or the complement of the DNA target nucleic acid, located so that when the RNA is subjected to selective RNAse degradation, there is no substantial degradation which would prevent formation of the primer extension product.

Conversely, the site for hybridization of the promoter oligonucleotide may be chosen so that sufficient degradation of the RNA strand occurs to permit efficient hybridization of the promoter oligonucleotide to the DNA strand. Typically, only portions of RNA are removed from the RNA:DNA duplex through selective RNAse degradation and, thus, some parts of the RNA strand will remain in the duplex. Selective RNAse degradation on the RNA strand of an RNA:DNA hybrid results in the dissociation of small pieces of RNA from the hybrid. Positions at which RNA is selectively degraded may be determined through standard hybridization analyses. Thus, a promoter oligonucleotide may be selected which will more efficiently bind to the DNA after selective RNAse degradation, i.e., will bind at areas where RNA fragments are selectively removed.

Promoters or promoter sequences suitable for incorporation in promoter oligonucleotides used in the methods of the present invention are nucleic acid sequences (either naturally occurring, produced synthetically or a product of a restriction digest) that are specifically recognized by an RNA polymerase that recognizes and binds to that sequence and initiates the process of transcription, whereby RNA transcripts are produced. Typical, known and useful promoters include those which are recognized by certain bacteriophage polymerases, such as those from bacteriophage T3, T7, and SP6, and a promoter from *E. coli*. The sequence may optionally include nucleotide bases extending beyond the actual recognition site for the RNA polymerase which may impart added stability or susceptibility to degradation processes or increased transcription efficiency. Promoter sequences for which there is a known and available polymerase that is capable of recognizing the initiation sequence are particularly suitable to be employed.

Suitable DNA polymerases for use in accordance with the methods of the invention include reverse transcriptases. Particularly suitable DNA polymerases include AMV reverse transcriptase and MMLV reverse transcriptase. Some of the reverse transcriptases suitable for use in the methods of the present invention, such as AMV and MMLV reverse transcriptases, have an RNAse H activity. Indeed, according to certain embodiments of the present invention, the only selective RNAse activity in the amplification reaction is provided by the reverse transcriptase—no additional selective RNAse is added. However, in some situations it may also be useful to add an exogenous selective RNAse, such as *E. coli* RNAse H. Although the addition of an exogenous selective RNAse is not required, under certain conditions, the RNAse H activity present in, e.g., AMV reverse transcriptase may be inhibited or inactivated by other components present in the reaction mixture. In such situations, addition of an exogenous selective RNAse may be desirable. For example, where relatively large amounts of heterologous DNA are present in the reaction mixture, the native RNAse H activity of the AMV reverse transcriptase may be somewhat inhibited and thus the number of copies of the target sequence produced accordingly reduced. In situations where the target nucleic acid comprises only a small portion of the nucleic acid present (e.g., where the sample contains significant amounts of heterologous DNA and/or RNA), it is particularly useful to add an exogenous selective RNAse. See, e.g., Kacian et al, U.S. Pat. No. 5,399,491.

RNA amplification products produced by the methods described above may serve as templates to produce additional amplification products related to the target sequence through the above-described mechanisms. The system is autocatalytic and amplification by the methods of the present invention occurs without the need for repeatedly modifying or changing reaction conditions such as temperature, pH, ionic strength and the like. These methods do not require an expensive thermal cycling apparatus, nor do they require several additions of enzymes or other reagents during the course of an amplification reaction.

As noted above, the methods of the present invention are useful in assays for detecting and/or quantitating specific nucleic acid target sequences in clinical, water, environmental, industrial, beverage, food, seed stocks and other samples or to produce large numbers of RNA amplification products from a specific target sequence for a variety of uses. For example, the present invention is useful to screen clinical samples (e.g., blood, urine, feces, saliva, semen, or spinal fluid), food, water, laboratory and/or industrial samples for the presence of specific nucleic acids, specific organisms (e.g., using species-specific oligonucleotides) and/or specific classes of organisms in applications such as in sterility testing (e.g., using universal oligonucleotides). The present invention can be used to detect the presence of, for example, viruses, bacteria, fungi, or parasites.

The amplification product can be detected by any conventional means. For example, amplification product can be detected by hybridization with a detectably labeled probe and measurement of the resulting hybrids. Design criteria in selecting probes for detecting particular target sequences are well known in the art and are described in, for example, Hogan et al., "Methods for Making Oligonucleotide Probes for the Detection and/or Quantitation of Non-Viral Organisms," U.S. Pat. No. 6,150,517. Hogan teaches that probes should be designed to maximize homology for the target sequence(s) and minimize homology for possible non-target sequences. To minimize stability with non-target sequences, Hogan instructs that guanine and cytosine rich regions should be avoided, that the probe should span as many destabilizing mismatches as possible, and that the length of perfect complementarity to a non-target sequence should be minimized. Contrariwise, stability of the probe with the target sequence(s) should be maximized, adenine and thymine rich regions should be avoided, probe:target hybrids are preferably terminated with guanine and cytosine base pairs, extensive self-complementarity is generally to be avoided, and the melting temperature of probe:target hybrids should be about 2-10° C. higher than the assay temperature.

In a particular embodiment, the amplification product can be assayed by the Hybridization Protection Assay ("HPA"), which involves hybridizing a chemiluminescent oligonucleotide probe to the target sequence, e.g., an acridinium ester-labeled ("AE") probe, selectively hydrolyzing the chemiluminescent label present on unhybridized probe, and measuring the chemiluminescence produced from the remaining probe in a luminometer. See, e.g., Arnold et al., "Homogenous Protection Assay," U.S. Pat. No. 5,283,174 and NORMAN C. NELSON ET AL., NONISOTOPIC PROBING, BLOTTING, AND SEQUENCING, ch. 17 (Larry J. Kricka ed., 2d ed. 1995).

In further embodiments, the present invention provides quantitative evaluation of the amplification process in real-time by methods described herein. Evaluation of an amplification process in "real-time" involves determining the amount of amplicon in the reaction mixture either continuously or periodically during the amplification reaction, and the determined values are used to calculate the amount of target sequence initially present in the sample. There are a variety of methods for determining the amount of initial target sequence present in a sample based on real-time amplification. These include those disclosed by Wittwer et al., "Method for Quantification of an Analyte," U.S. Pat. No.

6,303,305, and Yokoyama et al., "Method for Assaying Nucleic Acid," U.S. Pat. No. 6,541,205. Another method for determining the quantity of target sequence initially present in a sample, but which is not based on a real-time amplification, is disclosed by Ryder et al., "Method for Determining Pre-Amplification Levels of a Nucleic Acid Target Sequence from Post-Amplification Levels of Product," U.S. Pat. No. 5,710,029. Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of example, "molecular torches" are a type of self-hybridizing probe which includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification product under strand displacement conditions. Under strand displacement conditions, hybridization of the two complementary regions (which may be fully or partially complementary) of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed by Becker et al., "Molecular Torches," U.S. Pat. No. 6,534,274.

Another example of a detection probe having self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., "Detectably Labeled Dual Confirmation Oligonucleotide Probes, Assays and Kits," U.S. Pat. No. 5,925,517, and Tyagi et al., "Nucleic Acid Detection Probes Having Non-FRET Fluorescence Quenching and Kits and Assays Including Such Probes," U.S. Pat. No. 6,150,097.

Other self-hybridizing probes for use in the present invention are well known to those of ordinary skill in the art. By way of example, probe binding pairs having interacting labels, such as those disclosed by Morrison, "Competitive Homogenous Assay," U.S. Pat. No. 5,928,862 and Gelfand et al., U.S. Pat. No. 5,804,375 for PCR reactions, might be adapted for use in the present invention. Additional detection systems include "molecular switches," as disclosed by Arnold et al., "Oligonucleotides Comprising a Molecular Switch," U.S. Pat. Appln. Pub. No. US 2005-0042638 A1. And other probes, such as those comprising intercalating dyes and/or fluorochromes, might be useful for detection of amplification products in the present invention. See, e.g., Ishiguro et al., "Method of Detecting Specific Nucleic Acid Sequences," U.S. Pat. No. 5,814,447.

In those methods of the present invention where the initial target sequence and the RNA transcription product share the same sense, it may be desirable to initiate amplification before adding probe for real-time detection. Adding probe prior to initiating an amplification reaction may slow the rate of amplification since probe which binds to the initial target sequence has to be displaced or otherwise remove during the primer extension step to complete a primer extension product having the complement of the target sequence. The initiation of amplification is judged by the addition of amplification enzymes (e.g., a reverse transcriptase and an RNA polymerase).

In addition to the methods described herein, the present invention is drawn to kits comprising one or more of the reagents required for carrying out the methods of the present invention. Kits comprising various components used in carrying out the present invention may be configured for use in any procedure requiring amplification of nucleic acid target molecules, and such kits can be customized for various different end-users. Suitable kits may be prepared, for example, for microbiological analysis, blood screening, disease diagnosis, water testing, product release or sterility testing, environmental or industrial analysis, food or beverage testing, or for general laboratory use. Kits of the present invention provide one or more of the components necessary to carry out nucleic acid amplifications according to the invention. Kits may include reagents suitable for amplifying nucleic acids from one particular target or may include reagents suitable for amplifying multiple targets. Kits of the present invention may further provide reagents for real-time detection of one or more nucleic acid targets in a single sample, for example, one or more self-hybridizing probes as described above. Kits may comprise a carrier that may be compartmentalized to receive in close confinement one or more containers such as vials, test tubes, wells, and the like. Preferably at least one of such containers contains one or more components or a mixture of components needed to perform the amplification methods of the present invention.

A kit according to one embodiment of the present invention can include, for example, in one or more containers, a tagged oligonucleotide, alone or in combination with a tag closing oligonucleotide or joined to a tag closing sequence, a binding molecule or other means for terminating a primer extension reaction, and, optionally, an extender oligonucleotide and/or a capping oligonucleotide. If real-time detection is used, the one or more containers may include one or more reagents for real-time detection of at least one nucleic acid target sequence in a single sample, for example, one or more self-hybridizing probes as described above. Another container may contain an enzyme reagent, such as a heat stable DNA polymerase for performing a PCR or RT-PCR reaction, or a mixture of a reverse transcriptase (either with or without RNAse H activity), an RNA polymerase, and optionally an additional selective RNAse enzyme for a transcription-based amplification reaction. These enzymes may be provided in concentrated form or at working concentration, usually in a form which promotes enzyme stability. The enzyme reagent may also be provided in a lyophilized form. See Shen et al., "Stabilized Enzyme Compositions for Nucleic Acid Amplification," U.S. Pat. No. 5,834,254. Another one or more containers may contain an amplification reagent in concentrated form, e.g., 10×, 50×, or 100×, or at working concentration. An amplification reagent will contain one or more of the components necessary to run the amplification reaction, e.g., a buffer, $MgCl_2$, KCl, dNTPs, rNTPs, EDTA, stabilizing agents, etc. Certain of the components, e.g., $MgCl_2$ and rNTPs, may be provided separately from the remaining components, allowing the end user to titrate these reagents to achieve more optimized amplification reactions. Another one or more containers may include reagents for detection of amplification products, including one or more labeled oligonucleotide probes. Probes may be labeled in a number of alternative ways, e.g., with radioactive isotopes, fluorescent labels, chemiluminescent labels, nuclear tags, bioluminescent labels, intercalating dyes, or enzyme labels. In some embodiments, a kit of the present invention will also include one or more containers containing one or more positive and negative control target nucleic acids which can be utilized in amplification experiments in order to validate the test amplifications carried out by the end user. In some instances, one or more of the reagents listed above may be combined with an internal control. Of course, it is also possible to combine one or more of these reagents in a single tube or other containers. Supports suitable for use with the invention, e.g., test tubes, multi-tube units, multi-well plates, etc., may also be supplied with kits of the invention. Finally a kit of the present invention may include one or more instruction manuals.

Kits of the invention may contain virtually any combination of the components set out above or described elsewhere herein. As one skilled in the art would recognize, the components supplied with kits of the invention will vary with the intended use for the kits, and the intended end user. Thus, kits may be specifically designed to perform various functions set out in this application and the components of such kits will vary accordingly.

The present invention is further drawn to various oligonucleotides including, for example, the target specific oligonucleotides exemplified below. It is to be understood that oligonucleotides of the present invention may be DNA, RNA, DNA:RNA chimerics and analogs thereof, and, in any case, the present invention includes RNA equivalents of DNA oligonucleotides and DNA equivalents of RNA oligonucleotides.

Detection probes of the present invention may include, for example, an acridinium ester label, or labeled, self-hybridizing regions flanking the sequence which hybridizes to the target sequence. In various embodiments, these labeled oligonucleotide probes optionally or preferably are synthesized to include at least one modified nucleotide, e.g., a 2'-O-ME ribonucleotide; or these labeled oligonucleotide probes optionally or preferably are synthesized entirely of modified nucleotides, e.g., 2'-O-ME ribonucleotides.

It will be understood by one of ordinary skill in the relevant arts that other suitable modifications and adaptations to the methods, compositions, reaction mixtures and kits described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Examples are provided below illustrating certain aspects and embodiments of the invention. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

Unless otherwise indicated, oligonucleotides and modified oligonucleotides in the following examples were synthesized using standard phosphoramidite chemistry, various methods of which are well known in the art. See e.g., Carruthers et al. (1987) Meth. Enzymol. 154, 287. Unless otherwise stated herein, modified nucleotides were 2'-O-ME ribonucleotides, which were used in the synthesis as their phosphoramidite analogs.

Example 1

Selective Amplification of HCV Using Tagged Oligonucleotides in a Real-Time TMA Reaction The following series of experiments were conducted to evaluate whether the use of a tagged oligonucleotide to modify a target nucleic acid sequence in a nucleic acid sample of interest prior to a transcription-mediated amplification reaction would permit the selective amplification of target nucleic acid sequence contributed by the nucleic acid sample of interest, while not amplifying target nucleic acid sequence contributed by sources other than the nucleic acid sample of interest.

Reagents and protocol conditions used in the performed experiments, as well as a discussion of the results and conclusions of the experiments, are set forth below.

I. Oligonucleotides

Unless otherwise indicated, oligonucleotides were synthesized using an Expedite™ 8909 DNA Synthesizer (PerSeptive Biosystems, Framingham, Mass.) using standard phosphoramidite chemistry. See, e.g., Carruthers et al. (1987) Meth. Enzymol. 154, 287. Sequences are from 5'-to-3'. The blocking moiety, if present, is at the 3'-end.

1. Tagged Priming Oligonucleotide:

(SEQ ID NO: 1)
GTTTGTATGTCTGTTGCTATTATGTCTACAGGCATTGAGCGGGTTGATCC

AAGAAAGGAC; 12 pmol/rxn

2. Priming Oligonucleotide:

(SEQ ID NO: 2)
GTTTGTATGTCTGTTGCTATTAT; 12 pmol/rxn

3. Promoter Oligonucleotide:

(SEQ ID NO: 3)
ATTTAATACGACTCACTATAGGGAGACCACAACGGTTTCTAGCCATGGCG

TTAGTATGAG; 12 pmol/rxn

Blocking Moiety: A 3'-to-3' linkage prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01)

4. Terminating Oligonucleotide:

(SEQ ID NO: 4)
AmUmGmGmCmUmAmGmAmCmGmCmUmUmUmCmUmGmCmGmUmGmAmAmGm

Am; 0.8 pmol/rxn

Blocking Moiety: Same as promoter oligonucleotide

5. Extender Oligonucleotide:

(SEQ ID NO: 5)
TGTCGTGCAGCCTCCAGGACCCCCCCTCCCG GGAGAGCCATA; 12 pmol/rxn

Blocking Moiety: Same as promoter oligonucleotide

6. First Capture Probe:

(SEQ ID NO: 6)
GmGmGmCmAmCmUmCmGmCmAmAmGmCmAmmmCmCmCmUmTTTAAAAAAAA

AAAAAAA AAAAAAAAAAAAAAA; 3 pmol/rxn

7. Second Capture Probe:

(SEQ ID NO: 7)
CmAmUmGmGmUmGmCmAmCmGmGmUmCmUmAmCmGmTTTAAAAAAAAAAA

AAAAAAA AAAAAAAAAAA; 3 pmol/rxn

8. Detection Probe:

(SEQ ID NO: 8)
CmGmUmUmCmCmGmCmAmGmAmCmCmAmCmUmAmUm(Linker)GmAmAm

CmGm; 4 pmol/rxn

Probe Type: Molecular Torch

Linker: 9-O-Dimethoxytrityl-triethylene glycol, 1-[(2-cyanoethyl)-(N,N-diisopropyl)]-phosphoramidite (Glen Research Corporation, Sterling, Va.; Cat. No. 10-1909-90)

5' Label: 6-Carboxyfluorescein (FAM) (BioGenex, San Ramon, Calif.; Cat. No. BGX-3008-01)

3' Label: 4-(4'-dimethylaminophenylazo) benzoic acid (DABCYL) (Prime Synthesis, Inc., Aston, Pa.)

II. Reagents and Other Protocol Information

1. Amplification Reagent. The "Amplification Reagent" or "AMP Reagent" comprised 11.6 mM Trizma® base buffer, 15 mM Trizma® hydrochloride buffer, 25 mM MgCl$_2$, 23.3 mM KCl$_2$, 3.33% (v/v) glycerol, 0.05 mM zinc acetate, 0.76 mM dATP, 0.76 mM dCTP, 0.76 mM dGTP, 0.76 mM dTTP, 0.02% (v/v) ProClin 300 Preservative (Supelco, Bellefonte, Pa.; Cat. No. 48126), 6.0 mM ATP, 6.0 mM CTP, 6.0 mM GTP, and 6.0 mM UTP, pH 7.81 to 8.0 at 22° C.

2. Enzyme Reagent. The "Enzyme Reagent" comprised 70 mM N-acetyl-L-cysteine, 10% (v/v) TRITON® X-102 detergent, 16 mM HEPES, 3 mM EDTA, 0.05% (w/v) sodium azide, 20 mM Trizma® base buffer, 50 mM KCl$_2$, 20% (v/v) glycerol, 165.6 mM trehalose, pH 7, and containing 224 RTU/µL Moloney murine leukemia virus ("MMLV") reverse transcriptase and 140 U/µL T7 RNA polymerase, where one unit (i.e., RTU or U) of activity is defined as the synthesis and release of 5.75 fmol cDNA in 15 minutes at 37° C. for MMLV reverse transcriptase, and the production of 5.0 fmol RNA transcript in 20 minutes at 37° C. for T7 RNA polymerase.

3. Wash Solution. The "Wash Solution" comprised 10 mM HEPES, 6.5 mM NaOH, 1 mM EDTA, 0.3% (v/v) ethyl alcohol, 0.02% (w/v) methyl paraben, 0.01% (w/v) propyl paraben, 150 mM NaCl, and 0.1% (w/v) sodium dodecyl sulfate, pH 7.5.

4. Transport Medium. The "Transport Medium" comprised 150 mM HEPES, 8% (w/v) lithium lauryl sulfate, and 100 mM ammonium sulfate, pH 7.5.

5. Target Capture Reagent. The "Target Capture Reagent" or "TCR" comprised the components listed below. Additional information about the formulation of this mixture is described below under Target Capture Reagent Procedure (IIIA). The concentrations listed represent the final concentrations of the components after having been combined with the magnetic particle solution. The magnetic particles were Sera-Mag™ MG-CM Carboxylate Modified (Seradyn, Inc., Indianapolis, Ind.; Cat. No. 24152105-050250), 1 micron, super-paramagnetic particles covalently bound 5'-amino modified oligo(dT)$_{14}$. The HEPES, lithium hydroxide, lithium chloride, EDTA, lithium lauryl sulfate and ammonium sulfate components were introduced with the TCR diluent and Transport Medium.

First Capture Probe; 15.0 nM
Second Capture Probe; 15.0 nM
Tagged Priming Oligonucleotide; 60.0 nM
Terminating Oligonucleotide; 4.0 nM
HEPES, Free Acid, Dihydrate; 118.7 mM
Lithium Hydroxide, Monohydrate; 98.9 mM
Lithium Chloride, High Purity; 470.6 mM
EDTA, Free Acid; 25.0 mM
Lithium Lauryl Sulfate; 110.2 mM
Ammonium Sulfate; 37.5 mM
Seradyn Poly dT14 Magnetic Particles; 0.075 ug/uL 6. Transcript Buffer. The "Transcript Buffer" comprised 0.2% lithium lauryl sulfate.

7. Transcript Used. HCV Transcript

8. Product Numbers of Certain Materials or Equipment Used.

KingFisher™ Plate (Thermo Labsystems, Franklin, Mass.; Cat. No. 97002540)

MJ Research microtiter plate (Bio-Rad Laboratories, Inc., Hercules, Calif.; Cat. No. HSP-9665)

Solo HT Incubator (Thermo Labsystems, Franklin, Mass.; Cat. No. 5161580)

KingFisher™ Comb (Thermo Labsystems, Franklin, Mass.; Cat. No. 97002510)

Eppendorf® Thermomixer R (Eppendorf North America; Westbury, N.Y.; Cat. No. 022670107 or 022670158)

DNA Engine Opticon® 2 Real-Time PCR Detection System (Bio-Rad Laboratories, Inc., Hercules, Calif.; Cat. No. CFB-3220)

9. Additional Protocol Information.

For the described experiments, 3.3 µL of target-containing transcript buffer was added to each 2.0 ml microtube in step B6 below. The tagged priming oligonucleotide and the terminating oligonucleotide were in water before being added to the 2.0 mL microtubes. Samples were vortexed for about 5 seconds. Incubating for 10 minutes at 60° C. was found to be generally sufficient to capture the transcript. The plates were kept at room temperature for 5 minutes following the 10 minute incubation to allow the plates to cool before the target capture steps. This is also where the plates were transferred from the Solo HT Incubator to the KingFisher System. The speed of the thermomixer was 1400 rpm.

III. Target Capture Protocol

A. Target Capture Reagent (TCR) Procedure.

Magnetic beads were slowly mixed at room temperature (RT) for 45 minutes and 150 µL magnetic beads were added to 5 mL TCR diluent (15 ug beads/rxn when 50 µL used per sample). The solution was slowly mixed at room temperature for 35 minutes, at which time capture probe was added to 5 mL of the TCR diluent (to a final concentration of 0.12 pmol/µL (6-pmol/50 µL rxn).

B. Sample Preparation.

AMP Reagent was prepared containing the promoter oligonucleotide, extender oligonucleotide and priming oligonucleotide (volume=1,600 µL). The solution was vortexed and placed at 2-8° C. until needed. Detection probe was prepared in Enzyme Reagent and placed at 2-8° C. until needed. Target dilutions were prepared in 0.2% LLS. 50 µL TCR was transferred into 200 µL microplate wells. Each target copy level, tagged priming oligonucleotide and terminating oligonucleotide were added to 1.2 mL 50% Transport Medium, 50% $H_2O$ in 2.0 mL microtubes. Target samples were vortexed and 150 µL transferred into 200 µL microplate (Plate 1) well containing 50 µL TCR (each well contained zero or 1 million copies HCV transcript plus appropriate amounts of tagged priming and terminating oligonucleotides).

C. Target Capture Protocol.

The 200 µL microplate (Plate 1) was incubated at 60° C. for 10 minutes using Labsystems Solo HT Incubator (Plate 1), and the microplate was then placed at RT for 5 minutes (Plate 1). 200 µL microplates (Plates 2 & 3) were prepared with 200 uL Wash Reagent. Amplification plate (Plate 4-MJ research 96 well microtiter plate) was prepared with 30 µL AMP Reagent per well. The 96 well comb was placed into Plate 1. All four plates were loaded into the KingFisher 96 unit and the target capture protocol was initiated, as follows.

Plate 1 was mixed for 5 minutes at very slow speed and beads were collected for 12 counts and then released into Plate 2 for 10 seconds using slow speed. Plate 1 was then mixed for 1 second using very slow speed, beads collected for 12 counts, and the beads were released into Plate 2 for 10 seconds using slow speed.

Plate 2 was mixed for 30 seconds at medium speed and beads were collected for 12 counts and then released into Plate 3 for 10 seconds using very slow speed. Plate 2 was then mixed for 1 second at very slow speed and beads were collected for 12 counts and released into Plate 3 for 10 seconds using very slow speed.

Plate 3 was mixed for 30 seconds at medium speed, beads were collected for 12 counts, and the beads were released into Plate 4 for 10 seconds using medium speed. Plate 3 was then mixed for 1 second at very slow speed, beads collected for 12 counts and released into plate 4 for 10 seconds using medium speed.

The 96 well microtiter plate (Plate 4) was removed and transferred to the bench, covered with a sealing card, and placed in the DNA Engine Opticon® 2 Real-Time PCR Detection System (Bio-Rad Laboratories; Hercules, Calif.) ("real-time instrument").

D. Real Time TMA.

Real-time TMA was performed as follows. The plate was incubated for 5 minutes at 42° C. and then removed and placed on a 42° C. thermomixer. Each reaction well received a 10 µL aliquot of the Enzyme Reagent. The microtiter plate was covered with an adhesive tape seal, shaken gently for 30 seconds on the thermomixer, and then placed into the real-time instrument at 42° C., where real-time assay monitoring was commenced. TTime values, which served as indicators of the amount of amplicon synthesized, were determined from the monitored fluorescence signals. See Light et al., U.S. Pat. Appln. Pub. No. US 2006-0276972, paragraphs 506-549.

IV. Results and Conclusion

Experiments were performed according to the procedures described above for detecting an HCV transcript (8 replicates). The TCR in each test contained the same tagged priming oligonucleotide. A target capture step was performed for binding HCV transcript and removing unhybridized tagged priming oligonucleotide and terminating oligonucleotide. After the target capture step, an AMP Reagent was contacted with the beads of the TCR, with the AMP Reagent containing a priming oligonucleotide specific for the complement of the tag sequence. No tagged priming oligonucleotide was included in this step.

Eight replicates were run for each condition. The detection probe was added via the Enzyme Reagent at 4 pmol per reaction. The HCV AMP Reagent contained 12 pmol promoter oligonucleotide, 12 pmol extender oligonucleotide and 12 pmol priming oligonucleotide per reaction.

Figure 17:
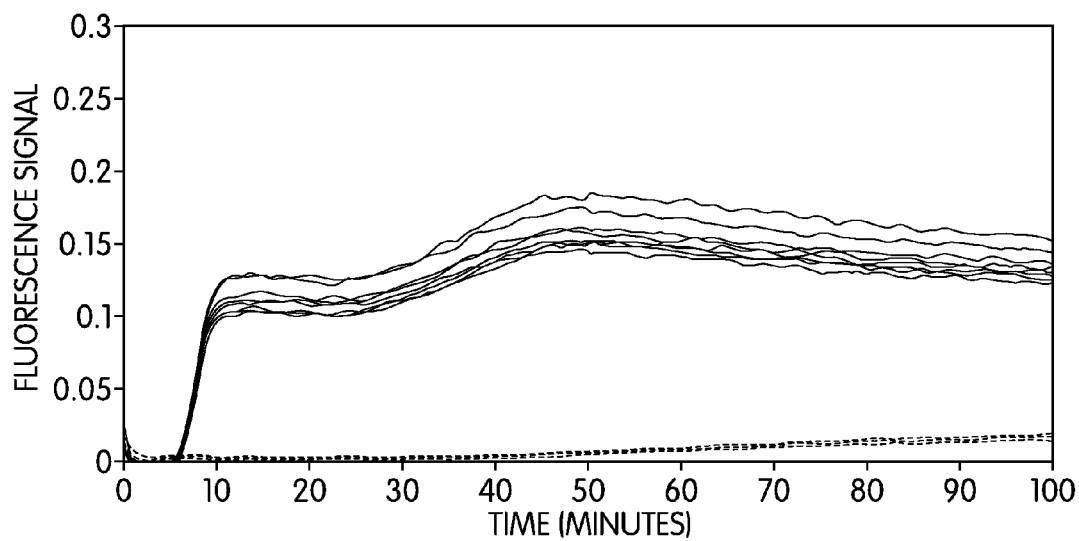
FIG. 17 shows the raw curves for HCV amplifications in which no target was spiked into the amplification reagent. There was no detectable amplification when the HCV transcript was not spiked into the target capture or amplification reagents, while the average TTime for reactions containing $1 \times 10^6$ copies of the HCV transcript in the target capture reagent was 6.3 minutes.

The first set of experiments compared the results of reactions in which no copies of the HCV transcript were spiked into the TCR or AMP Reagent with the results of reactions in which $1 \times 10^6$ copies of the HCV transcript were spiked into the TCR. FIG. 17 shows the raw curves for HCV amplifications in which no target was spiked into the AMP Reagent. There was no detectable amplification when the HCV transcript was not spiked into the TCR or AMP Reagent, while the average TTime for reactions containing $1 \times 10^6$ copies of the HCV transcript in the TCR was 6.3 minutes. The "TTime" values relate to time of emergence (time at which signal rises above background), and a summary of these values for the experiments performed is set forth in Table 1 below.

Figure 18:
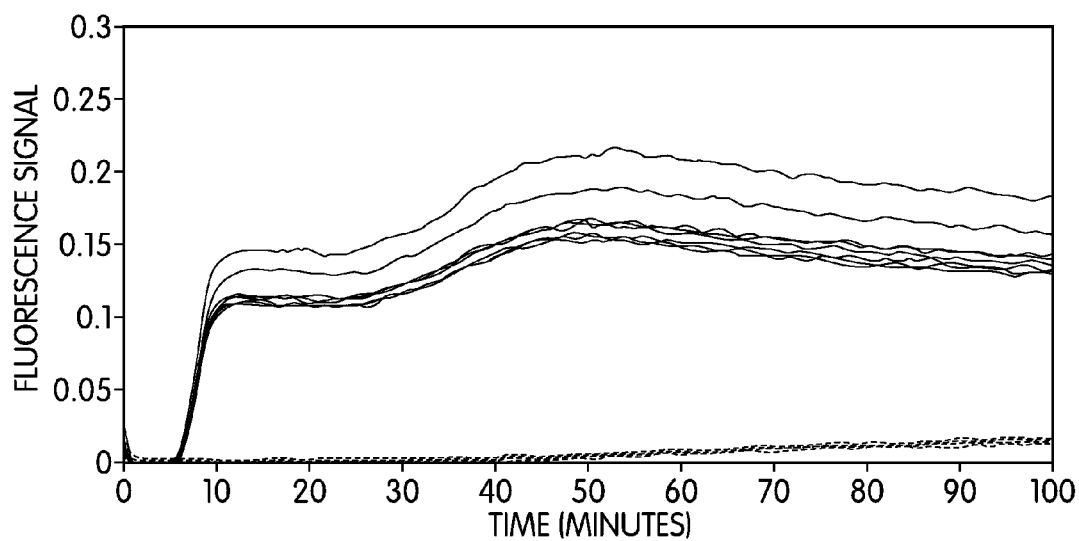
FIG. 18 shows the raw curves for HCV amplifications in which target was spiked into the amplification reagent. There was no detectable amplification when the HCV transcript was spiked into the amplification reagent, while the average TTime for reactions containing $1 \times 10^6$ copies of the HCV transcript in the target capture reagent was 6.3 minutes. The zero samples in target capture did not amplify, even with 1 million copies HCV 1a spiked into the amplification reagent.

A second set of experiments compared the results of reactions in which $1 \times 10^6$ copies of the HCV transcript were spiked into the AMP Reagent only with reactions in which $1 \times 10^6$ copies of the HCV transcript were spiked into the TCR only. FIG. 18 shows the raw curves for HCV amplifications in which target was spiked into the AMP Reagent. There was no detectable amplification when the HCV transcript was spiked into the AMP Reagent, while the average TTime for reactions containing $1 \times 10^6$ copies of the HCV transcript in the TCR was 6.3 minutes (Table 1). The zero target in TC samples did not amplify, even with 1 million copies HCV transcript spiked into the AMP Reagent.

Figure 19:
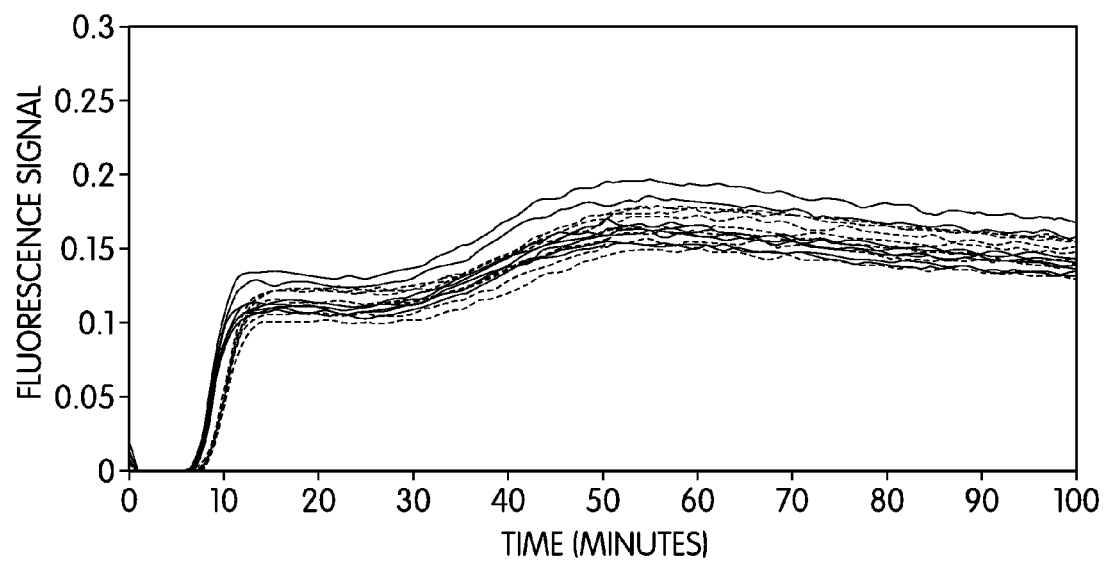
FIG. 19 shows the raw curves for HCV amplifications in which target and tagged nonT7 primer were spiked into the amplification reagent. The AvgTTime for 1 million copies HCV 1a target present only in the target capture step with tagged nonT7 primer & terminating oligonucleotide spiked into the amplification reagent was 7.2 minutes. The zero samples in target capture with target, terminating oligonucleotide & tagged nonT7 primer spiked into the amplification reagent also produced robust amplification with an AvgTTime=8.6 minutes.

A third set of experiments compared the results of reactions in which $1 \times 10^6$ copies of the HCV transcript and the tagged priming oligonucleotide were provided in the AMP Reagent (no copies of the HCV transcript in TCR) with the results of reactions in which $1 \times 10^6$ copies of the HCV transcript were provided in the TCR and the tagged priming oligonucleotide was provided in the AMP Reagent. FIG. 19 shows that the AvgTTime for 1 million copies HCV transcript present only in the target capture step with tagged priming and terminating oligonucleotides spiked into the AMP Reagent was 7.2 minutes. The zero samples with target, terminating oligonucleotide and tagged priming oligonucleotide spiked into the AMP Reagent also produced robust amplification with an AvgTTime=8.6 minutes (Table 1).

TABLE 1

| | | TTime Summary (AvgTTimes & SDTTimes) | | | | | |
|---|---|---|---|---|---|---|---|
| Sample ID | Target Name | Target Amt | Total | RN1 | TN1 | Avg. T Time | SDT Time |
| 1 million target in TC-x6.0 | HCV | 1E6 | 8 | 7 | 8 | 6.3 | 0.11 |
| 1 million target in TC, tagged non-T7 primer & terminating oligonucleotide in amp-x6.0 | HCV | 1E6 | 8 | 8 | 8 | 7.2 | 0.20 |
| 1 million target in TC-x6.0 | HCV | 1E6 | 8 | 8 | 7 | 6.3 | 0.05 |
| Zero target in TC, 1 million target in amp-x0.0 | HCV | 0.00 | 8 | 8 | 0 | N/A | N/A |
| Zero target in TC, 1 million target, tagged non-T7 primer & terminating oligonucleotide in amp-x0.0 | HCV | 0.00 | 8 | 8 | 8 | 8.6 | 0.21 |
| Zero target in TC-x0.0 | HCV | 0.00 | 8 | 8 | 0 | N/A | N/A |

The results of these experiments demonstrate that only when the tagged priming oligonucleotide was present in the AMP Reagent along with the priming oligonucleotide did zero TCR samples amplify when 1 million copies of HCV transcript were spiked into the AMP Reagent. Thus, HCV transcript entering the system through the AMP Reagent is not amplified unless the tagged priming oligonucleotide is also provided with the AMP Reagent.

The preceding Example demonstrated how a tagged priming oligonucleotide that hybridized to an HCV template could be used for selectively detecting HCV nucleic acids in a sample of interest without interference from contaminating nucleic acid introduced subsequent to a target capture step. The following Example illustrates how a similar approach was used for detecting bacterial nucleic acids in a sample of interest despite the presence of contaminating templates in reagents used for performing the amplification reaction. Advantageously, non-complexed tagged priming oligonucleotide was substantially absent from the reaction mixture at the time a complex comprising the tagged priming oligonucleotide and the template contacted the DNA polymerase used in the amplification reaction.

Example 2 below describes two procedures for amplifying E. coli rRNA nucleic acids, where the procedures differed by the use of both a tagged priming oligonucleotide and target capture. The first procedure employed an E. coli specific non-tagged priming oligonucleotide in combination with a terminating oligonucleotide, a promoter oligonucleotide and a detection probe. The second procedure employed a tagged priming oligonucleotide having a target-complementary sequence identical to that contained in the E. coli specific non-tagged priming oligonucleotide of the first procedure, a tag-specific priming oligonucleotide, as well as a terminating oligonucleotide, a promoter oligonucleotide and a detection probe. The tag-specific priming oligonucleotide, which had a nucleotide sequence corresponding to a segment of HIV-1, hybridized to the complement of the tag sequence contained in the tagged priming oligonucleotide, but did not hybridize to the E. coli rRNA template nucleic acid or the complement thereof. In the case of the second procedure, the terminating oligonucleotide, the promoter oligonucleotide and the detection probe were identical to those used in the first procedure. As demonstrated below, amplification reactions that omitted the tagged priming oligonucleotide failed to discriminate between samples containing 0 and $10^6$ copies of a synthetic E. coli rRNA target. Conversely, the approach that included use of a tagged priming oligonucleotide and target capture clearly distinguished samples containing 0 and $10^3$ copies of the synthetic E. coli rRNA target.

Example 2

Use of a Tagged Priming Oligonucleotide Allows Discrimination Between Sample-Derived Templates and Exogenous Templates A. Amplification Using a Non-Tagged Priming Oligonucleotide without Target Capture In a first procedure, amplification reactions employing a synthetic E. coli rRNA template were performed using a non-tagged priming oligonucleotide that hybridized to the template, a promoter oligonucleotide, a terminating oligonucleotide and a molecular torch detection probe. Reactions were primed using the synthetic template added directly into the reaction mixtures (i.e., without undergoing target capture purification) at 0 or $10^6$ copies/reaction. A molecular torch detection probe was used to monitor amplicon production as a function of time. In the nucleotide sequences presented below, 2'-O-methyl ribose (2'-O-Me) modifications of the polynucleotide backbone are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). Oligonucleotides, reagents and essential methods used in the procedure were as follows.

I. Oligonucleotides

1. Non-Tagged Priming Oligonucleotide:

CmUmGmCmTGGCACGGAGTTAGCCGGTGCTTC  (SEQ ID NO: 9)

2. Promoter Oligonucleotide:

(SEQ ID NO: 10)
ATTTAATACGACTCACTATAGGGAGAGAAGGCCTTCGGGTTGTAAAG - block

3. Terminating Oligonucleotide:

(SEQ ID NO: 11)
GmCmCmUmUmCmUmUmCmAmUmAmCmAmCmGmCmGm - block

4. Detection Probe:

(SEQ ID NO: 12)
¹CmUmGmCmGmGmGmUmAmAmCmGmUmCmAmAmUmGmAmGmCmAmAmAm² CGCAG³
¹fluorescein
²C9 linker
³DABCYL 5. Synthetic *E. coli* rRNA template:

(SEQ ID NO: 13)
AAATTGAAGAGTTTGATCATGGCTCAGATTGAACGCTGGCGGCAGGCCTA
ACACATGCAAGTCGAACGGTAACAGGAAGAAGCTTGCTTCTTTGCTGACG
AGTGGCGGACGGGTGAGTAATGTCTGGGAAACTGCCTGATGGAGGGGGAT
AACTACTGGAAACGGTAGCTAATACCGCATAACGTCGCAAGACCAAAGAG
GGGGACCTTCGGGCCTCTTGCCATCGGATGTGCCCAGATGGGATTAGCTA
GTAGGTGGGGTAACGGCTCACCTAGGCGACGATCCCTAGCTGGTCTGAGA
GGATGACCAGCCACACTGGAACTGAGACACGGTCCAGACTCCTACGGGAG
GCAGCAGTGGGGAATATTGCACAATGGGCGCAAGCCTGATGCAGCCATGC
CGCGTGTATGAAGAAGGCCTTCGGGTTGTAAAGTACTTTCAGCGGGGAGG
AAGGGAGTAAAGTTAATACCTTTGCTCATTGACGTTACCCGCAGAAGAAG
CACCGGCTAACTCCGTGCCAGCAGCCGCGGTAATACGGAGGGTGCAAGCG
TTAATCGGAATTACTGGGCGTAAAGCGCACGCAGGCGGTTTGTTAAGTCA
GATGTGAAATCCCCGGGCTCAACCTGGGAACTGCATCTGATACTGGCAAG
CTTGAGTCTCGTAGAGGGGGTAGAATTCCAGGTGTAGCGGTGAAATGCG
TAGAGATCTGGAGGAATACCGGTGGCGAAGGCGGCCCCCTGGACGAAGAC
TGACGCTCAGGTGCGAAAGCGTGGGGAGCAAACAGGATTAGATACCCTGG
TAGTCCACGCCGTAAACGATGTCGACTTGGAGGTTGTGCCCTTGAGGCGT
GGCTTCCGGAGCTAACGCGTTAAGTCGACCGCCTGGGGAGTACGGCCGCA
AGGTTAAAACTCAAATGAATTGACGGGGGCCCGCACAAGCGGTGGAGCAT
GTGGTTTAATTCGATGCAACGCGAAGAACCTTACCTGGTCTTGACATCCA
CGGAAGTTTTCAGAGATGAGAATGTGCCTTCGGGAACCGTGAGACAGGTG
CTGCATGGCTGTCGTCAGCTCGTGTTGTGAAATGTTGGGTTAAGTCCCGC
AACGAGCGCAACCCTTATCCTTTGTTGCCAGCGGTCCGGCCGGGAACTCA
AAGGAGACTGCCAGTGATAAACTGGAGGAAGGTGGGGATGACGTCAAGTC
ATCATGGCCCTTACGACCAGGGCTACACACGTGCTACAATGGCGCATACA
AAGAGAAGCGACCTCGCGAGAGCAAGCGGACCTCATAAAGTGCGTCGTAG
TCCGGATTGGAGTCTGCAACTCGACTCCATGAAGTCGGAATCGCTAGTAA
TCGTGGATCAGAATGCCACGGTGAATACGTTCCCGGGCCTTGTACACACC
GCCCGTCACACCATGGGAGTGGGTTGCAAAAGAAGTAGGTAGCTTAACCT
TCGGGAGGGCGCTTACCACTTTGTGATTCATGACTGGGGTGAAGTCGTAA
CAAGGTAACCGTAGGGGAACCTGCGGTTGGATCACCTCCTTA

II. Reagents and Other Protocol Information

Amplification and enzyme reagents were essentially as described under Example 1. Procedures using the non-tagged priming oligonucleotide that hybridized to the *E. coli* template did not employ target capture oligonucleotides or reagents, did not employ transport medium or wash solution, and did not employ an extender oligonucleotide.

A. Real-Time Amplification Protocol.

Sample solutions were prepared using primerless amplification reagent, non-tagged priming oligonucleotide, promoter oligonucleotide, terminating oligonucleotide, detection probe and synthetic template nucleic acid. Each well of a 96-well microtiter plate received a 30 μL aliquot of the prepared sample solution. The microtiter plate was covered with an adhesive tape seal, incubated first for 10 minutes at 60° C. in the DNA ENGINE OPTICON® 2 (Bio-Rad Laboratories; Hercules, Calif.) temperature-controlled real-time instrument, and then temperature-adjusted to 42° C. for 5 minutes. Thereafter, the plate was removed from the real-time instrument and placed onto a 42° C. thermomixer. Each reaction well received a 10 μL aliquot of the enzyme reagent. The microtiter plate was covered with an adhesive tape seal, shaken gently for 30 seconds on the thermomixer, and then placed into the real-time instrument at 42° C. where real-time assay monitoring was commenced. TTime values, which served as indicators of the amount of amplicon synthesized, were determined from the monitored fluorescence signals.

III. Results and Conclusion

Figure 20:
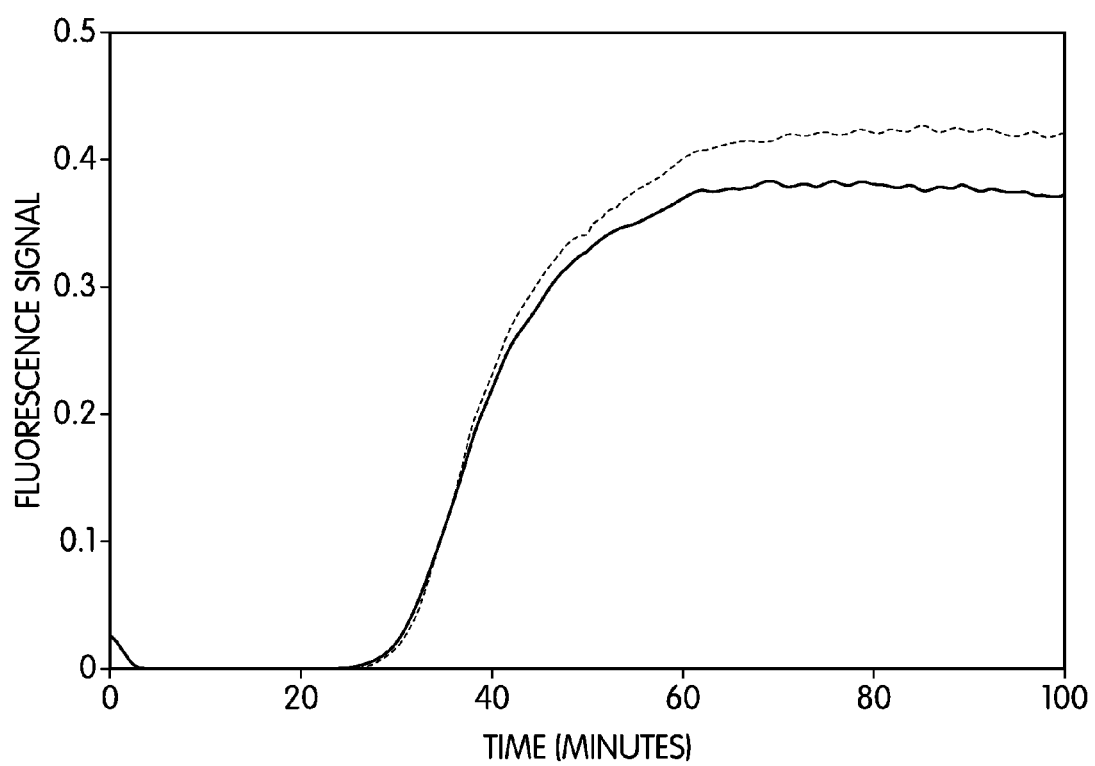
FIG. 20 is graph showing results from time-dependent monitoring of nucleic acid amplification reactions that included either 0 or $10^6$ copies of a synthetic E. coli rRNA template. The thin broken line shows results for the reaction conducted using 0 copies of template, and the heavy solid line shows results for the reaction conducted using $10^6$ copies of template.

As indicated in FIG. 20, substantially identical results were observed in reactions that included either 0 or $10^6$ copies of the template nucleic acid, and so the assay showed no discrimination between these two conditions. More specifically, fluorescent signals indicating formation of *E. coli* nucleic acid amplification products emerged from background levels at substantially similar times (i.e., TTime=31.74 minutes at the 0 copy level, and 31.19 minutes at the $10^6$ copy level) in both reactions. Thus, a real-time amplification profile characteristic of high levels of the nucleic acid template was obtained even in the absence of added *E. coli* rRNA template. This was consistent with the presence of contaminating bacterial nucleic acid templates in one or more of the reagents used for carrying out the amplification reactions following the target capture procedure.

B. Amplification Using a Tagged Priming Oligonucleotide and Target Capture

In a second procedure, a tagged priming oligonucleotide and target capture step were employed for performing amplification reactions using test samples containing either 0, $10^3$ or $10^5$ copies of the synthetic *E. coli* transcript. Oligonucleotides used in the procedure are indicated below. The molecular torch detection probe was added as a component of the enzyme reagent. Following target capture, tagged priming oligonucleotide that was not hybridized to template nucleic acid was removed from the system by standard target capture and wash steps. The complex that included the rRNA template and the tagged priming oligonucleotide remained captured on super-paramagnetic particles. Amplification reactions were carried out using reagents essentially as described above, except for substitution of a non-specific target capture probe for the sequence-specific capture probes employed in Example 1. Amplification reactions were carried out in replicates of six and monitored using a molecular torch detection probe essentially as described in Example 1, except that an extender oligonucleotide was omitted. As above, 2'-O-methyl ribose (2'-O-Me) modifications of the polynucleotide backbone in the sequences presented below are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat.

No. 20-0102-01). Oligonucleotides, reagents and essential methods used in the procedure were as follows.

I. Oligonucleotides:

1. Tagged Priming Oligonucleotide:

(SEQ ID NO: 14)
GTTTGTATGTCTGTTGCTATTATGTCTACCTGCTGGCACGGAGTTAGCCG

GTGCTTC

2. Tag-Specific Priming Oligonucleotide:

GTTTGTATGTCTGTTGCTATTAT    (SEQ ID NO: 15)

3. Promoter Oligonucleotide:

(SEQ ID NO: 10)
ATTTAATACGACTCACTATAGGGAGAGAAGGCCTTCGGGTTGTAAAG - block

4. Terminating Oligonucleotide:

(SEQ ID NO: 11)
GmCmCmUmUmCmUmUmCmAmUmAmCmAmCmGmCmGm - block

5. Non-Specific Capture Probe:

(SEQ ID NO: 16)
KmKmKmKmKmKmKmKmKmKmKmKmKmKmKmKmKmKmKmTTTAAAAAAAAAA

AAAAAAAAAAAAAAAAAAAA

6. Detection Probe:

(SEQ ID NO: 12)
¹CmUmGmCmGmGmGmUmAmAmCmGmUmCmAmAmUmGmAmGmCmAmAmAm²

CGCAG³
¹fluorescein
²C9 linker
³DABCYL

7. Synthetic *E. coli* rRNA template
(See above)

II. Reagents and Other Protocol Information

Reagents and experimental protocols were essentially as described under Example 1, with the substitution of a non-specific target capture oligonucleotide for the first and second capture oligonucleotides, the substitution of the above-presented *E. coli*-specific oligonucleotides for HCV-specific oligonucleotides, and the omission of an extender oligonucleotide.

III. Non-Specific Target Capture Protocol

A. Target Capture Reagent (TCR) Preparation.

A stock suspension of magnetic beads was mixed at room temperature for 30 minutes. An aliquot of about 150 µL of the magnetic bead suspension was added to 5 mL of TCR diluent (15 µg beads/reaction when using 50 µL/sample), and then slowly mixed at room temperature for 30 minutes. Next, the non-specific capture oligonucleotide was added to 5 mL of the TCR mixture to yield a final concentration of 0.12 pmol/µL. The prepared TCR was mixed gently at room temperature until needed.

B. Sample Preparation.

Amplification solution was prepared using primerless amplification reagent, promoter oligonucleotide and tag-specific priming oligonucleotide. The prepared amplification solution was mixed by vortexing and then maintained at 2-8° C. until needed. Enzyme reagent containing the molecular torch detection probe was next prepared and maintained at 2-8° C. until needed. Dilutions of the template rRNA were prepared in 0.2% LLS (lithium lauryl sulfate). Aliquots (50 µL) of the magnetic bead target capture solution were transferred into the wells of a microtiter plate for a KINGFISHER 96 (Thermo Fisher Scientific, Inc.; Waltham, Mass.) magnetic particle processor. Samples of diluted template, tagged priming oligonucleotide and terminating oligonucleotide were then added to 1.5 mL of 50% transport medium diluted with water. The target-containing sample mixture was vortexed, and 150 µL aliquots transferred into the microtiter plate (Plate 1) wells containing 50 µL target capture solution (each well contained 0, $10^3$ or $10^5$ copies of the *E. coli* transcript and the appropriate amount of tagged priming oligonucleotide and terminating oligonucleotide).

C. Target Capture Protocol.

First there was prepared a microtiter plate containing 200 µL of wash reagent (Plate 2). Another microtiter plate (Plate 3) for conducting amplification reactions was prepared, with each well to be used for a reaction containing 30 µL of amplification reagent. All three plates (Plates 1-3) were loaded into the magnetic particle processor unit. Magnetic beads harboring nucleic acid complexes were isolated from Plate 1, washed in Plate 2, and then transferred into Plate 3 using standard procedures familiar to those having an ordinary level of skill in the art. Plate 3 was removed from the magnetic particle processor unit, covered with an adhesive tape seal, and then placed into the temperature-controlled real-time instrument.

D. Real-Time Amplification Protocol.

Plate 3 was incubated at 42° C. for 5 minutes in the real-time instrument. The microtiter plate was removed from the real-time instrument and placed onto a 42° C. thermomixer. Each reaction well received a 10 µL aliquot of enzyme reagent containing detection probe, and was then covered with an adhesive tape seal. The plate was shaken gently for 60 seconds on the thermomixer, and then placed back into the real-time instrument at 42° C. where real time assay monitoring was commenced. TTime values, which served as indicators of the amount of amplicon synthesized, were determined from the monitored fluorescence signals.

IV. Results and Conclusion

Figure 21:
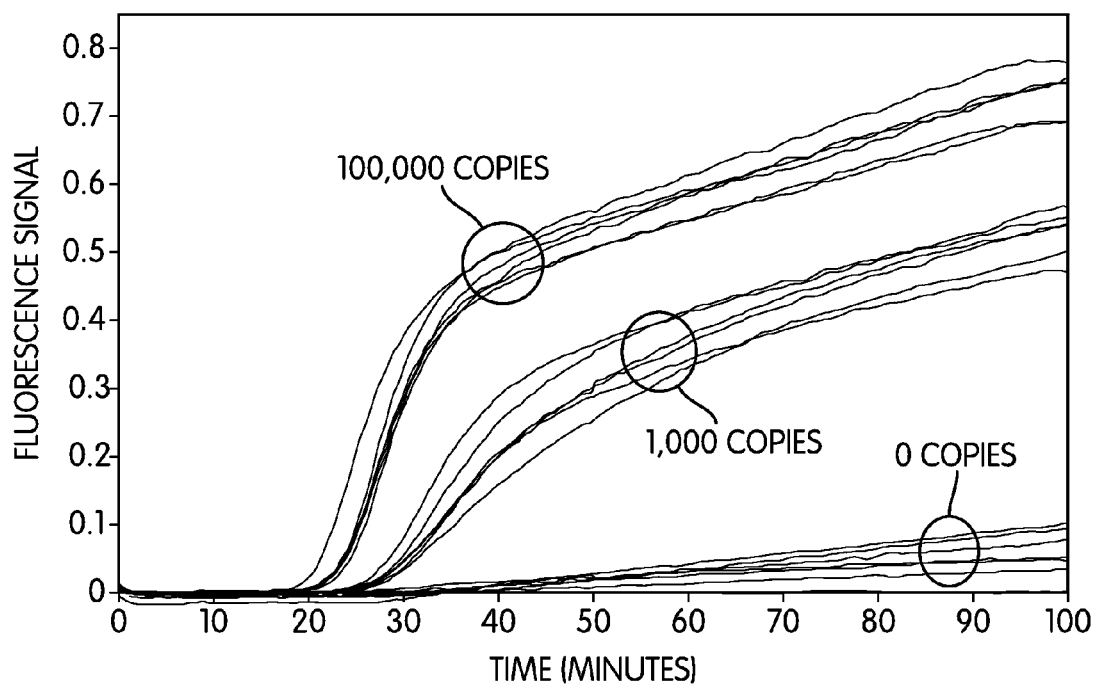
FIG. 21 is graph showing results from time-dependent monitoring of nucleic acid amplification reactions that included either 0, $10^3$ or $10^5$ copies of a synthetic E. coli rRNA template.

FIG. 21 graphically illustrates the benefits of the disclosed approach to nucleic acid amplification. Procedures that employed a tagged priming oligonucleotide complementary to a target of interest, a target capture step, and a tag-specific priming oligonucleotide that was not complementary to the target of interest (i.e., the *E. coli* rRNA) yielded dramatically reduced background amplification levels, and so easily permitted discrimination between 0 and $10^3$ copies of the bacterial template nucleic acid. More specifically, the average TTime values determined for reactions carried out using $10^5$ copies, $10^3$ copies, and 0 copies of the *E. coli* template were 24.7 minutes, 30.6 minutes and 37.5 minutes, respectively. Taken together with the results presented in FIG. 4, these findings were consistent with the presence of bacteria-derived nucleic acids in common reagents used for conducting in vitro nucleic acid amplification reactions. Despite this fact, the procedure employing a tagged priming oligonucleotide was useful for detecting *E. coli* nucleic acids contained in a test sample without interference from exogenous template nucleic acids contributed by the amplification reagents. For example, a qualitative assay for detecting *E. coli* nucleic acids at a level of $10^3$ copies or greater in a test sample could depend on achieving a threshold fluorescence signal or TTime value after a predetermined reaction time (e.g., 35 minutes).

The following Example presents comparative results showing how two different detection probes influenced the profiles of real-time amplification run curves. The results further showed how the tagged priming oligonucleotide approach could be used for discriminating 0 and $10^3$ copies of the synthetic E. coli template nucleic acid—a level approximating the number of copies of 16S rRNA present in a single bacterium.

Example 3 describes detection of E. coli rRNA templates in real-time amplification reactions using three different detection probes.

Example 3

Alternative Torch Designs can Improve Assay Results

Amplification reactions were conducted and monitored in a real-time format using one of three different detection probes. The synthetic template nucleic acid, non-specific capture oligonucleotide, tagged priming oligonucleotide, termination oligonucleotide, promoter oligonucleotide and tag-specific priming oligonucleotide used for performing the reactions were identical to those used in the second procedure of the preceding Example. The E. coli target hybridizing portion of the tagged priming oligonucleotide corresponded to nucleotide positions 24-57 of SEQ ID NO:14 (i.e., the target hybridizing sequence corresponding to SEQ ID NO:19). The E. coli target hybridizing portion of the promoter oligonucleotide corresponded to nucleotide positions 27-47 of SEQ ID NO:10 (i.e., the target hybridizing sequence corresponding to SEQ ID NO:20). Four replicates were run for each condition. As before, detection probe was added with the enzyme reagent. Reagents and protocols for non-specific target capture, sample preparation, and real-time amplification also were essentially as described in the second procedure of the preceding Example. Notably, reactions were conducted using 0, $10^3$ or $10^5$ copies of the synthetic E. coli template. As above, 2'-O-methyl ribose (OMe) modifications of the polynucleotide backbone in the sequences presented below are indicated by lower case "m." Blocking moieties at the 3' termini of the promoter oligonucleotide and terminating oligonucleotide comprised a 3'-to-3' linkage that was prepared using 3'-dimethyltrityl-N-benzoyl-2'-deoxycytidine, 5'-succinoyl-long chain alkylamino-CPG (Glen Research Corporation, Sterling, Va.; Cat. No. 20-0102-01). Oligonucleotides, reagents and essential methods used in the procedure were as follows.

I. Oligonucleotides:

1. Tagged Priming Oligonucleotide:

```
                                     (SEQ ID NO: 14)
GTTTGTATGTCTGTTGCTATTATGTCTACCTGCTGGCACGGAGTTAGCCG

GTGCTTC
```

2. Tag-Specific Priming Oligonucleotide:

```
    GTTTGTATGTCTGTTGCTATTAT     (SEQ ID NO: 15)
```

3. Promoter Oligonucleotide:

```
                                     (SEQ ID NO: 10)
ATTTAATACGACTCACTATAGGGAGAGAAGGCCTTCGGGTTGTAAAG - block
```

4. Terminating Oligonucleotide:

```
                                     (SEQ ID NO: 11)
    GmCmCmUmUmCmUmUmCmAmUmAmCmAmCmGmCmGm - block
```

5. Non-Specific Capture Probe:

```
                                     (SEQ ID NO: 16)
KmKmKmKmKmKmKmKmKmKmKmKmKmKmKmKmKmKmTTTAAAAAAAAAAA

AAAAAAAAAAAAAAAAAAA
```

6. Detection Probe:

```
                                     (SEQ ID NO: 17)
¹CmGmAmGmCmAmAmAmGmGmUmAmUmUmAmAmCm²GmCmUmCmGm³

(SEQ ID NO: 18)
¹CmGmAmGmCmAmAmAmGmGmUmAmUmUmAmAmCmUmUmUmAmCmUmCm²

GmCmUmCmGm³
¹fluorescein
²C9 linker
³DABCYL
```

7. Synthetic E. coli rRNA template
(See above)

II. Reagents and Other Protocol Information

Reagents and experimental protocols were essentially as described under Example 2, with a slight change to the conditions used for target capture.

III. Non-Specific Target Capture Protocol:

A. Target Capture Reagent (TCR) Preparation.

A stock suspension of magnetic beads was mixed at room temperature for 25 minutes. A 150 µL aliquot of the magnetic bead suspension was added to 5 mL of TCR diluent (15 µg beads/reaction when using 50.micro.L/sample), and then slowly mixed at room temperature for 25 minutes. Next, the non-specific capture oligonucleotide was added to 5 mL of the TCR mixture to yield a final concentration of 0.12 pmol/µL. The prepared TCR was mixed gently at room temperature until needed.

B. Sample Preparation.

Amplification solutions were prepared using primerless AMP Reagent, promoter oligonucleotide and tag-specific priming oligonucleotide. The prepared amplification solutions were mixed by vortexing and then maintained at 2-8° C. until needed. Enzyme Reagents containing the molecular torch detection probes were next prepared and maintained at 2-8° C. until needed. Dilutions of the template rRNA were prepared in 0.2% LLS, as described above. Aliquots (50 µL) of the magnetic bead target capture solution were transferred into the wells of a microtiter plate for a KINGFISHER 96 (Thermo Fisher Scientific, Inc.; Waltham, Mass.) magnetic particle processor. Samples of diluted template, tagged priming oligonucleotide and terminating oligonucleotide were then added to 1.5 mL of 50% Transport Medium diluted with water. The target-containing sample mixture was vortexed, and 150 µL aliquots transferred into the microtiter plate (Plate 1) wells containing 50 µL target capture solution (each well contained 0, $10^3$ or $10^5$ copies of the E. coli transcript and the appropriate amount of tagged priming oligonucleotide and terminating oligonucleotide).

C. Target Capture Protocol.

The microtiter plate (Plate 1) was incubated at 60° C. for 15 minutes using a SOLO HT incubator (Thermo Labsystems; Franklin, Mass.). The microtiter plate was then placed on the bench at room temperature and allowed to equilibrate for 5 minutes (Plate 1). Next, there was prepared a second microtiter plate containing 200 µL of Wash Reagent (Plate 2). A third microtiter plate (Plate 3) for conducting amplification reactions was prepared, with each well to be used for a reaction containing 30 µL of amplification reagent. All three plates were loaded into the magnetic particle processor unit. Magnetic beads harboring nucleic acid complexes were isolated from Plate 1, washed in Plate 2, and then transferred into Plate 3 using standard procedures familiar to those having an ordinary level of skill in the art. Plate 3 was removed from the magnetic particle processor unit, covered with an adhesive tape seal, and then placed into the temperature-controlled real-time instrument.

D. Real-Time Amplification Protocol.

Plate 3 was incubated in the real-time instrument at 42° C. for 5 minutes. The microtiter plate was removed from the real-time instrument and placed onto the 42° C. thermomixer. Each reaction well received a 10 µL aliquot of Enzyme Reagent containing detection probe, and was then covered with an adhesive tape seal. The plate was shaken gently for 60 seconds on the thermomixer, and then placed back into the real-time instrument at 42° C. where real-time assay monitoring was commenced. TTime values, which served as indicators of the amount of amplicon synthesized, were determined from the monitored fluorescence signals.

IV. Results and Conclusion

The results presented in Table 2 summarize the average TTime values (column 3), and the standard deviations of the average TTime values (column 4) for reactions conducted using the different detection probes. The tabular summary confirmed that all of the tested detection probes yielded very good results in the real-time assays. Each probe advantageously gave a very low signal at the 0 copy level of input target. More specifically, amplicon detected in reactions carried out using 0 copies of input synthetic template was essentially undetectable when the reactions included the detection probes of SEQ ID NO:17 and SEQ ID NO:18. Thus, reactions that included one of the detection probes identified by SEQ ID NO:17 and SEQ ID NO:18 gave outstanding results that easily permitted detection of template nucleic acids corresponding roughly to the amount contained in a single bacterium.

TABLE 2

Use of Alternative Detection Probes for Improved Assay Discrimination

| Template Amount (copies) | Detection Probe | AvgTTime (minutes) | SDTTime (minutes) |
|---|---|---|---|
| 0 | SEQ ID NO: 17 | N/A | N/A |
| $10^3$ | | 38.2 | 2.81 |
| $10^5$ | | 26.4 | 0.32 |
| 0 | SEQ ID NO: 18 | N/A | N/A |
| $10^3$ | | 35.9 | 2.33 |
| $10^5$ | | 28.8 | 0.45 |

Taken in view of the results presented Examples 2 and 3, each of SEQ ID Nos:12, and 17-18 represent preferred molecular torches for detecting E. coli using the methods described herein. Highly preferred probes useful for detecting E. coli nucleic acids will have target-complementary sequences corresponding to nucleotide positions 2-24 contained within the probe of SEQ ID NO:12 (i.e., the target hybridizing sequence corresponding to SEQ ID NO:21), or nucleotide positions 2-17 contained within the probe of SEQ ID NO:17 (i.e., the target hybridizing sequence corresponding to SEQ ID NO:22), or nucleotide positions 2-24 contained within the probe of SEQ ID NO:18 (i.e., the target hybridizing sequence corresponding to SEQ ID NO:23). Generally speaking, probes useful for detecting E. coli nucleic acids will have target hybridizing sequences of at least 16 contiguous nucleotides contained within the sequence of TGCGGG-TAACGTCAATGAGCAAAGGTATTAACTTTACTC (SEQ ID NO:24). Overall preferred lengths of desirable probes will be up to 39 nucleotides, more preferably up to 29 nucleotides, more preferably up to 23 nucleotides, or still more preferably up to 16 nucleotides. Of course, useful probes may include RNA and DNA equivalent bases, and include the complements of the foregoing described probes.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A method for the selective amplification of at least one target nucleic acid sequence from a nucleic acid sample, said method comprising the steps of:
   (a) treating a nucleic acid sample comprising a target nucleic acid sequence with a tagged oligonucleotide comprising first and second regions, said first region comprising a target hybridizing sequence which hybridizes to a 3'-end of said target nucleic acid sequence and said second region comprising a tag sequence situated 5' to said target hybridizing sequence, wherein said second region does not stably hybridize to a target nucleic acid containing said target nucleic acid sequence, and wherein said target nucleic acid sequence is contained in each of a plurality of ribosomal nucleic acids from multiple species of microorganisms;
   (b) prior to initiating a primer extension reaction, reducing in said nucleic acid sample the effective concentration of unhybridized tagged oligonucleotide having an active form in which a target hybridizing sequence of said unhybridized tagged oligonucleotide is available for hybridization to said target nucleic acid sequence; and
   (c) after step (b), initiating an extension reaction from the 3'-end of the tagged oligonucleotide with a DNA polymerase to produce a primer extension product comprising a region complementary to the target nucleic acid sequence;
   (d) separating the primer extension product from the target nucleic acid; and
   (e) producing amplification products in a nucleic acid amplification reaction using first and second oligonucleotides, wherein said first oligonucleotide comprises a hybridizing sequence which hybridizes to a 3'-end of the complement of said target nucleic acid sequence and said second oligonucleotide comprises a hybridizing sequence which hybridizes to the complement of said tag sequence, wherein said second oligonucleotide does stably hybridize to said target nucleic acid, and wherein each of said amplification products comprises a base sequence which is substantially identical or complementary to the base sequence of said target nucleic acid sequence and further comprises a base sequence which is substantially identical or complementary to all or a portion of said tag sequence.

2. The method of claim 1, wherein step (b) comprises removing unhybridized tagged oligonucleotide from said nucleic acid sample.

3. The method of claim 2, wherein said target nucleic acid sequence is immobilized on a solid support during step (b).

4. The method of claim 1, wherein step (b) comprises inactivating unhybridized tagged oligonucleotide so that said unhybridized tagged oligonucleotide does not stably hybridize to said target nucleic acid sequence during step (c).

5. The method of claim 4 further comprising removing unhybridized tagged oligonucleotide from said nucleic acid sample during step (b).

6. The method of claim 4, wherein said tagged oligonucleotide has an active form during step (a) which permits said target hybridizing sequence to hybridize to said target nucleic acid sequence, and wherein unhybridized tagged oligonucleotide is converted to an inactive form in step (b) which blocks or prevents said tagged oligonucleotide from hybridizing to said target nucleic acid sequence during step (c).

7. The method of claim 6, wherein the conditions of steps (b)-(e) are less stringent than the conditions of step (a).

8. The method of claim 7, wherein the temperature of said nucleic acid sample is lowered between steps (a) and (b).

9. The method of claim 6, wherein unhybridized tagged oligonucleotide from step (a) is converted from a single-stranded form to a duplexed form in step (b).

10. The method of claim 9, wherein the duplexed form is hairpin tag molecule comprising a tag closing sequence joined to a 5'-end of said tagged oligonucleotide, wherein said tag closing sequence hybridizes to said target hybridizing sequence under the conditions of step (b), thereby blocking hybridization of unhybridized tagged oligonucleotide from step (a) to said target nucleic acid sequence in steps (b)-(e).

11. The method of claim 10, wherein said tag closing sequence is joined to said tagged oligonucleotide by a non-nucleotide linker.

12. The method of claim 10, wherein a 3'-end of said tag closing sequence is joined to a 5'-end of said tagged oligonucleotide.

13. The method of claim 4, wherein said target hybridizing sequence is hybridized to a tag closing oligonucleotide in step (b), said tagged oligonucleotide and said tag closing oligonucleotide being distinct molecules.

14. The method of claim 13, wherein said tag closing oligonucleotide is modified to prevent the initiation of DNA synthesis therefrom.

15. The method of claim 14, wherein a 3'-terminal base of said target hybridizing sequence is hybridized to a 5'-terminal base of said tag closing oligonucleotide.

16. The method of claim 14, wherein said tagged oligonucleotide and said tag closing oligonucleotide are both present in said nucleic acid sample during step (a), and wherein said target hybridizing sequence favors hybridization to said target nucleic acid sequence over said tag closing oligonucleotide in step (a).

17. The method of claim 1, wherein the conditions of said nucleic acid amplification reaction are isothermal.

18. The method of claim 17, wherein said nucleic acid amplification reaction is a transcription-based amplification reaction.

19. A kit for use in the selective amplification of at least one target nucleic acid sequence from a nucleic acid sample, said kit comprising:

(a) a tagged oligonucleotide comprising:
  (i) a first region comprising a target hybridizing sequence which hybridizes to a 3'-end of a target nucleic acid sequence under a first set of conditions so that said first region can be extended in a template-dependent manner in the presence of a DNA polymerase; and
  (ii) a second region comprising a tag sequence situated 5' to said first region, wherein said second region does not stably hybridize to a target nucleic acid containing said target nucleic acid sequence under said first set of conditions;
  wherein said target nucleic acid sequence is contained in each of a plurality of ribosomal nucleic acids from multiple species of microorganisms;
(b) a tag closing sequence which hybridizes to said target hybridizing sequence under a second set of conditions, thereby blocking hybridization of said tagged oligonucleotide to said target nucleic acid sequence, wherein said tag closing sequence does not stably hybridize to said target hybridizing sequence under said first set of conditions; and
(c) a first priming oligonucleotide which hybridizes to the complement of said tag sequence under said second set of conditions so that said first priming oligonucleotide can be extended in a template-dependent manner in the presence of a DNA polymerase.

20. A pre-amplification reaction mixture for selective amplification of one or more target nucleic acid sequences, said reaction mixture comprising:
a tagged oligonucleotide comprising first and second regions, said first region comprising a target hybridizing sequence hybridized to a target region contained at a 3'-end of a target nucleic acid sequence present in said reaction mixture and said second region comprising a tag sequence situated 5' to said target hybridizing sequence, wherein said target nucleic acid sequence is contained in each of a plurality of ribosomal nucleic acids from multiple species of microorganisms;
a first oligonucleotide comprising a hybridizing sequence which hybridizes to a 3'-end of the complement of said target nucleic acid sequence; and
a second oligonucleotide comprising a hybridizing sequence which hybridizes to the complement of said tag sequence,
wherein said reaction mixture is substantially free of an active form of said tagged oligonucleotide which is not hybridized to said target region contained in said target nucleic acid sequence present in said reaction mixture,
wherein said active form of said tagged oligonucleotide has an available target hybridizing sequence for hybridization to said target region present in a non-target nucleic acid added to said reaction mixture, and
wherein said reaction mixture does not comprise a nucleic acid polymerase capable of extending any of said oligonucleotides in a template-dependent manner.

* * * * *

SEQUENCE LISTING

<160> NUMBER OF SEQ ID NOS: 24

<210> SEQ ID NO 1
<211> LENGTH: 60
<212> TYPE: DNA
<213> ORGANISM: Artificial
<220> FEATURE:
<223> OTHER INFORMATION: HCV-specific tagged priming oligonucleotide

<400> SEQUENCE: 1
gtttgtatgt ctgttgctat tatgtctaca ggcattgagc gggttgatcc aagaaaggac        60

<210> SEQ ID NO 2
<211> LENGTH: 23
<212> TYPE: DNA
<213> ORGANISM: Artificial
<220> FEATURE:

<223> OTHER INFORMATION: Tag-specific priming oligonucleotide

<400> SEQUENCE: 2
gtttgtatgt ctgttgctat tat                                          23

<210> SEQ ID NO 3
<211> LENGTH: 60
<212> TYPE: DNA
<213> ORGANISM: Artificial
<220> FEATURE:
<223> OTHER INFORMATION: HCV-specific promoter oligonucleotide

<400> SEQUENCE: 3
atttaatacg actcactata gggagaccac aacggtttct agccatggcg ttagtatgag    60

<210> SEQ ID NO 4
<211> LENGTH: 26
<212> TYPE: RNA
<213> ORGANISM: Hepatitis C virus
<220> FEATURE:
<221> NAME/KEY: misc_feature
<222> LOCATION: (1)..(26)
<223> OTHER INFORMATION: 2' methoxy analogs

<400> SEQUENCE: 4
auggcuagac gcuuucugcg ugaaga                                       26

<210> SEQ ID NO 5
<211> LENGTH: 42
<212> TYPE: DNA
<213> ORGANISM: Artificial
<220> FEATURE:
<223> OTHER INFORMATION: Extender oligonucleotide

<400> SEQUENCE: 5
tgtcgtgcag cctccaggac ccccctccc gggagagcca ta                      42

<210> SEQ ID NO 6
<211> LENGTH: 52
<212> TYPE: DNA
<213> ORGANISM: Artificial
<220> FEATURE:
<223> OTHER INFORMATION: HCV-specific capture probe

<400> SEQUENCE: 6
gggcacucgc aagcacccut ttaaaaaaaa aaaaaaaaa aaaaaaaaa aa             52

<210> SEQ ID NO 7
<211> LENGTH: 51
<212> TYPE: DNA
<213> ORGANISM: Artificial
<220> FEATURE:
<223> OTHER INFORMATION: HCV-specific capture probe

<400> SEQUENCE: 7
cauggugcac ggucuacgtt taaaaaaaa aaaaaaaaa aaaaaaaaa a               51

<210> SEQ ID NO 8
<211> LENGTH: 23
<212> TYPE: RNA
<213> ORGANISM: Artificial
<220> FEATURE:
<223> OTHER INFORMATION: HCV-specific molecular torch hybridization
      probe
<220> FEATURE:
<221> NAME/KEY: misc_feature
<222> LOCATION: (1)..(23)

```
<223> OTHER INFORMATION: 2' methoxy analogs
<220> FEATURE:
<221> NAME/KEY: misc_feature
<222> LOCATION: (18)..(19)
<223> OTHER INFORMATION: non-nucleotide linker

<400> SEQUENCE: 8
cguuccgcag accacuauga acg                                            23

<210> SEQ ID NO 9
<211> LENGTH: 28
<212> TYPE: DNA
<213> ORGANISM: Escherichia coli
<220> FEATURE:
<221> NAME/KEY: misc_feature
<222> LOCATION: (1)..(4)
<223> OTHER INFORMATION: 2' methoxy analogs

<400> SEQUENCE: 9
cugctggcac ggagttagcc ggtgcttc                                       28

<210> SEQ ID NO 10
<211> LENGTH: 47
<212> TYPE: DNA
<213> ORGANISM: Artificial
<220> FEATURE:
<223> OTHER INFORMATION: E. coli-specific promoter oligonucleotide

<400> SEQUENCE: 10
atttaatacg actcactata gggagagaag gccttcgggt tgtaaag                  47

<210> SEQ ID NO 11
<211> LENGTH: 18
<212> TYPE: RNA
<213> ORGANISM: Escherichia coli
<220> FEATURE:
<221> NAME/KEY: misc_feature
<222> LOCATION: (1)..(18)
<223> OTHER INFORMATION: 2' methoxy analogs

<400> SEQUENCE: 11
gccuucuuca uacacgcg                                                  18

<210> SEQ ID NO 12
<211> LENGTH: 29
<212> TYPE: DNA
<213> ORGANISM: Artificial
<220> FEATURE:
<223> OTHER INFORMATION: E. coli-specific molecular torch hybridization
      probe
<220> FEATURE:
<221> NAME/KEY: misc_feature
<222> LOCATION: (1)..(24)
<223> OTHER INFORMATION: 2' methoxy analogs
<220> FEATURE:
<221> NAME/KEY: misc_feature
<222> LOCATION: (24)..(25)
<223> OTHER INFORMATION: non-nucleotide linker
<220> FEATURE:
<221> NAME/KEY: misc_feature
<222> LOCATION: (25)..(29)
<223> OTHER INFORMATION: DNA

<400> SEQUENCE: 12
cugcggguaa cgucaaugag caaacgcag                                      29

<210> SEQ ID NO 13
<211> LENGTH: 1542
<212> TYPE: DNA
```

<213> ORGANISM: Artificial
<220> FEATURE:
<223> OTHER INFORMATION: Synthetic E. coli rRNA template

<400> SEQUENCE: 13

```
aaattgaaga gtttgatcat ggctcagatt gaacgctggc ggcaggccta acacatgcaa     60
gtcgaacggt aacaggaaga agcttgcttc tttgctgacg agtggcggac gggtgagtaa    120
tgtctgggaa actgcctgat ggagggggat aactactgga aacggtagct aataccgcat    180
aacgtcgcaa gaccaaagag ggggaccttc gggcctcttg ccatcggatg tgcccagatg    240
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctggaa ctgcatctga tactggcaag cttgagtctc     660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca    780
aacaggatta taccctgg tagtccacgc cgtaaacgat gtcgacttgg aggttgtgcc     840
cttgaggcgt ggcttccgga gctaacgcgt taagtcgacc gcctggggag tacggccgca    900
aggttaaaac tcaaatgaat tgacgggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca agagaagcg    1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcacctcct ta                      1542
```

<210> SEQ ID NO 14
<211> LENGTH: 57
<212> TYPE: DNA
<213> ORGANISM: Artificial
<220> FEATURE:
<223> OTHER INFORMATION: E. coli-specific tagged priming oligonucleotide

<400> SEQUENCE: 14

```
gtttgtatgt ctgttgctat tatgtctacc tgctggcacg gagttagccg gtgcttc        57
```

<210> SEQ ID NO 15
<211> LENGTH: 23
<212> TYPE: DNA
<213> ORGANISM: Artificial
<220> FEATURE:
<223> OTHER INFORMATION: Tag-specific priming oligonucleotide

<400> SEQUENCE: 15
gtttgtatgt ctgttgctat tat                                    23

<210> SEQ ID NO 16
<211> LENGTH: 51
<212> TYPE: DNA
<213> ORGANISM: Artificial
<220> FEATURE:
<223> OTHER INFORMATION: non-specific capture probe
<220> FEATURE:
<221> NAME/KEY: misc_feature
<222> LOCATION: (1)..(18)
<223> OTHER INFORMATION: 2' methoxy analogs
<220> FEATURE:
<221> NAME/KEY: misc_feature
<222> LOCATION: (19)..(51)
<223> OTHER INFORMATION: DNA

<400> SEQUENCE: 16
kkkkkkkkkk kkkkkkkktt taaaaaaaaa aaaaaaaaaa aaaaaaaaaa a       51

<210> SEQ ID NO 17
<211> LENGTH: 22
<212> TYPE: RNA
<213> ORGANISM: Artificial
<220> FEATURE:
<223> OTHER INFORMATION: E. coli-specific molecular torch hybridization
      probe
<220> FEATURE:
<221> NAME/KEY: misc_feature
<222> LOCATION: (1)..(22)
<223> OTHER INFORMATION: 2' methoxy analogs
<220> FEATURE:
<221> NAME/KEY: misc_feature
<222> LOCATION: (17)..(18)
<223> OTHER INFORMATION: non-nucleotide linker

<400> SEQUENCE: 17
cgagcaaagg uauuaacgcu cg                                     22

<210> SEQ ID NO 18
<211> LENGTH: 29
<212> TYPE: RNA
<213> ORGANISM: Artificial
<220> FEATURE:
<223> OTHER INFORMATION: E. coli-specific molecular torch hybridization
      probe
<220> FEATURE:
<221> NAME/KEY: misc_feature
<222> LOCATION: (1)..(29)
<223> OTHER INFORMATION: 2' methoxy analogs
<220> FEATURE:
<221> NAME/KEY: misc_feature
<222> LOCATION: (24)..(25)
<223> OTHER INFORMATION: non-nucleotide linker

<400> SEQUENCE: 18
cgagcaaagg uauuaacuuu acucgcucg                              29

<210> SEQ ID NO 19
<211> LENGTH: 34
<212> TYPE: DNA
<213> ORGANISM: Escherichia coli

<400> SEQUENCE: 19
gtctacctgc tggcacggag ttagccggtg cttc                        34

<210> SEQ ID NO 20
<211> LENGTH: 21
<212> TYPE: DNA

```
<213> ORGANISM: Escherichia coli

<400> SEQUENCE: 20
gaaggccttc gggttgtaaa g                                              21

<210> SEQ ID NO 21
<211> LENGTH: 23
<212> TYPE: RNA
<213> ORGANISM: Escherichia coli

<400> SEQUENCE: 21
ugcggguaac gucaaugagc aaa                                            23

<210> SEQ ID NO 22
<211> LENGTH: 16
<212> TYPE: RNA
<213> ORGANISM: Escherichia coli

<400> SEQUENCE: 22
gagcaaaggu auuaac                                                    16

<210> SEQ ID NO 23
<211> LENGTH: 23
<212> TYPE: RNA
<213> ORGANISM: Escherichia coli

<400> SEQUENCE: 23
gagcaaaggu auuaacuuua cuc                                            23

<210> SEQ ID NO 24
<211> LENGTH: 39
<212> TYPE: DNA
<213> ORGANISM: Escherichia coli

<400> SEQUENCE: 24
tgcgggtaac gtcaatgagc aaaggtatta actttactc                           39
```